United States Patent [19]
Ladouceur et al.

[11] Patent Number: 6,051,586
[45] Date of Patent: Apr. 18, 2000

[54] SULFONAMIDE SUBSTITUTED CHROMAN DERIVATIVES USEFUL AS BETA 3 ADRENORECEPTOR AGONISTS

[75] Inventors: Gaetan H. Ladouceur, Branford; Richard D. Connell, Trumbull; Jeremy Baryza, New Haven; Ann-Marie Campbell, Monroe; Timothy G. Lease, Guilford; James H. Cook, East Hampton, all of Conn.

[73] Assignee: Bayer Corporation, Pittsburgh, Pa.

[21] Appl. No.: 09/199,014

[22] Filed: Nov. 23, 1998

Related U.S. Application Data

[60] Provisional application No. 60/122,061, Dec. 19, 1997.

[51] Int. Cl.[7] ............... C07D 311/58; C07D 405/12; C07D 407/12; A61K 31/353

[52] U.S. Cl. ............... 514/337; 514/340; 514/343; 514/382; 514/456; 546/268.4; 546/283.1; 546/276.4; 548/251; 549/399; 549/404

[58] Field of Search ............... 514/337, 340, 514/343, 382, 456; 546/268.4, 276.4, 283.1; 548/251; 549/399, 404

[56] References Cited

U.S. PATENT DOCUMENTS

| | | | |
|---|---|---|---|
| 3,706,764 | 12/1972 | Nakanishi et al. | 260/327 |
| 3,803,176 | 4/1974 | Christensen et al. | 260/345.2 |
| 4,647,579 | 3/1987 | Kabbe et al. | 514/456 |
| 4,650,812 | 3/1987 | Cohen et al. | 514/456 |
| 4,654,362 | 3/1987 | Van Lommen et al. | 514/452 |
| 5,393,775 | 2/1995 | Le Baut et al. | 514/456 |
| 5,451,677 | 9/1995 | Fisher et al. | 546/138 |
| 5,516,917 | 5/1996 | Djuric et al. | 548/525 |
| 5,541,197 | 7/1996 | Fisher et al. | 514/311 |
| 5,561,142 | 10/1996 | Fisher et al. | 514/312 |
| 5,663,194 | 9/1997 | Mewshaw | 514/456 |

FOREIGN PATENT DOCUMENTS

| | | | |
|---|---|---|---|
| 0079637 | 5/1983 | European Pat. Off. | C07D 311/24 |
| 0091749 | 10/1983 | European Pat. Off. | C07C 143/78 |
| 0328251 | 8/1989 | European Pat. Off. | C07C 103/178 |
| 0611003 | 8/1994 | European Pat. Off. | C07C 311/21 |
| 0801060 | 10/1997 | European Pat. Off. | C07D 209/42 |
| 2746395 | 9/1997 | France | C07D 409/12 |
| 2511647 | 9/1975 | Germany | C07D 311/22 |
| 08198866 | 8/1996 | Japan . | |
| 9429290 | 12/1994 | WIPO | C07D 307/85 |
| 9525104 | 9/1995 | WIPO | C07D 405/12 |
| 9529159 | 11/1995 | WIPO | C07D 213/30 |
| 9735835 | 10/1997 | WIPO | C07C 217/74 |

OTHER PUBLICATIONS

Silverman, Structure modifications to increase potency and Therapeutic Index, The Organic Chemistry of Drug Design and Drug Action, pp. 15–22, 1992.

*Primary Examiner*—Mukund J. Shah
*Assistant Examiner*—Deepak R. Rao
*Attorney, Agent, or Firm*—Alice A. Brewer

[57] ABSTRACT

This invention related to novel sulfonamide substituted chroman derivatives which are useful in the treatment of beta-3 receptor mediated conditions.

11 Claims, No Drawings

SULFONAMIDE SUBSTITUTED CHROMAN DERIVATIVES USEFUL AS BETA 3 ADRENORECEPTOR AGONISTS

This application claims the benefit of U.S. Provisional Application Ser. No. 60/122,061 filed Dec. 19, 1997.

FIELD OF THE INVENTION

This invention relates to novel chroman compounds, intermediates useful for their preparation, pharmaceutical compositions containing such compounds, and methods of selectively treating beta 3 adrenoreceptor mediated conditions with such compositions.

BACKGROUND OF THE INVENTION

Adrenoreceptors, or adrenergic receptors, are sites on effector organs that are innervated by postganglionic adrenergic fibers of the sympathetic nervous system and are classified as alpha-adrenergic and beta-adrenergic receptors. Alpha-adrenergic receptors respond to norepinephrine and to such blocking agents as phenoxybenzamine and phentolamine, whereas beta-adrenergic receptors respond to epinephrine and to such blocking agents as propranolol.

Beta-adrenergic receptors are subclassified as beta-1, beta-2 and beta-3 adrenoreceptors. Beta-1 stimulation causes cardiostimulation, whereas beta-2 stimulation causes bronchodilation and vasodilation.

Beta-3 receptors are found on the cell surface of both white and brown adipocytes where their stimulation promotes both lipolysis and energy expenditure. Agonists selective for beta-3 adrenoreceptors are known to be useful in the treatment of hyperglycemia (diabetes) and obesity in mammals, as well as in the treatment of gastrointestinal disorders and neurogenetic inflammation (U.S. Pat. No. 5,561,142). Additionally, they are known to lower triglyceride and cholesterol levels and to raise high density lipoprotein levels in mammals (U.S. Pat. No. 5,451,677). Accordingly, they are useful in the treatment of conditions such as hyper-triglyceridaemia, hypercholesterolaemia and in lowering high density lipoprotein levels as well as in the treatment of atherosclerotic and cardiovascular diseases and related conditions.

Treatment of such chronic diseases with agonists that are selective for beta-3 adrenoreceptors decreases the potential for undesirable side effects caused by beta-1 or beta-2 receptor stimulation such as increased heart rate (beta-1) and muscle tremor (beta-2). It has now been found that certain novel chroman derivatives are effective as selective beta-3 agonists and useful in the treatment of beta-3 mediated conditions.

DESCRIPTION OF THE INVENTION

This invention specifically relates to chroman compounds of formula I:

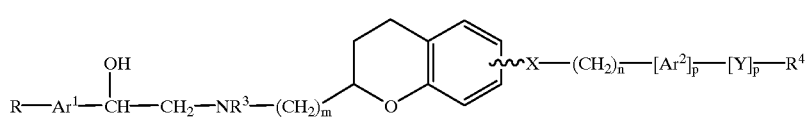

wherein:
R is hydrogen, hydroxy, oxo, halo, $C_1$–$C_{10}$haloalkyl, $C_1$–$C_{10}$ alkyl, cyano, nitro, $NR^1R^1$, $SR^1$, $OR^1$, $SO_2R^2$, $OCOR^2$, $NR^1COR^2$, $COR^2$, $NR^1SO_2R^2$, $NR^1CO_2R^1$, pyrrole, or $Ar^2$, optionally substituted with hydroxy, halogen, cyano, $NR^1R^1$, $SR^1$, trifluoromethyl, $OR^1$, $C_3$–$C_8$ cycloaklyl, phenyl, $NR^1COR^2$, $COR^2$, $SO_2R^2$, $OCOR^2$, $NR^1SO_2R^2$, or $NR^1CO_2R^1$;

$R^1$ is hydrogen, $C_1$–$C_{10}$ alkyl optionally substituted with 1 to 4 substituents selected from hydroxy, halogen, $CO_2H$, $CO_2C_1$–$C_{10}$ alkyl, $SO_2C_1$–$C_{10}$alkyl, $C_1$–$C_{10}$ alkoxy; or $C_3$–$C_8$ cycloalkyl, phenyl or naphthyl, each optionally substituted with 1 to 4 substituents selected from halogen, nitro, oxo, $C_1$–$C_{10}$ alkyl, $C_1$–$C_{10}$ alkoxy, and $C_1$–$C_{10}$ alkylthio; p1 $R^2$ is $R^1$ or $NR^1R^1$;

$R^3$ is hydrogen, $C_1$–$C_{10}$ alkyl or

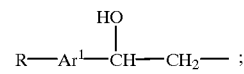

$Ar^1$ is $Ar^1$—O—$CH_2$, phenyl, or a 5 or 6 membered heterocyclic ring with from 1 to 4 heteroatoms selected from O, S and N, each moiety being optionally fused to a 5 membered heterocyclic ring containing from 1 to 4 hetero atoms selected from O, S, and N, the fused heterocyclic ring being optionally fused to a phenyl ring or substituted with oxo;

m is 1,2 or 3;

$(CH_2)_m$ may be optionally replaced with C—O—$(CH_2)_m$;

X is $SO_2$-piperizinyl, $NR^3$—$SO_2$, or $SO_2$—$NR^3$;

n is 0, 1, 2, 3, or 4;

$Ar^2$ is phenyl, or a 5 or 6 membered heterocyclic ring with from 1 to 4 heteroatoms selected from O, S and N, each moiety being optionally substituted with halogen, $C_1$–$C_{10}$ alkyl, $C_1$–$C_{10}$ alkoxy, and OR, or being fused to a 5 membered heterocyclic ring containing from 1 to 4 hetero atoms selected from O, S, and N, the fused heterocyclic ring being optionally fused to a phenyl ring or optionally substituted with oxo;

Y is O—Y, $NR^1$, $NR^1CO$, $C_3$–$C_8$ cycloalkyl or a 5 or 6 membered heterocyclic ring with from 1 to 4 heteroatoms selected from O, S and N, each of which is optionally substituted with oxo;

p is 0 or 1;

$R^4$ is hydrogen, $R^1$, $R^2$, oxo, $C_1$–$C_{10}$ heteroalkyl, $C_1$–$C_{10}$ alkyl, $C_1$–$C_{10}$ haloalkyl, each being optionally substituted with $C_3$–$C_8$ cycloalkyl, phenyl, naphthyl, benzofuran, carbazole, dibenzothiofuran, or a 5 or 6 membered heterocyclic ring with from 1 to 4 heteroatoms selected from O, S, and N, each ring structure being optionally substituted with halo and $C_1$–$C_{10}$ alkyl, and pharmaceutically acceptable salts and esters thereof.

The terms identified above have the following meaning throughout:

$C_1$–$C_{10}$ alkyl means straight or branched chain alkyl groups having from one to about ten carbon atoms, and includes such groups as methyl, ethyl, n-propyl, isopropyl, n-butyl, isobutyl, sec-butyl, tert-butyl, as well as vinyl, allyl, propynyl, butenyl, butadienyl, isopropenyl, and the like.

$C_1$–$C_{10}$ haloalkyl means straight or branched chain alkyl groups having from about one to about ten carbon atoms, the alkyl groups being substituted with one or more halogen atoms, and includes such groups as trifluoromethyl, trichloromethyl, pentafluoroethyl, fluoromethyl, 6-chlorohexyl, and the like.

The term $C_1$–$C_{10}$ alkoxy means straight or branched chain alkoxy groups having from one to about ten carbon atoms, and includes such groups as methoxy, ethoxy, n-propoxy, isopropoxy, n-butoxy, isobutoxy, sec-butoxy, tert-butoxy, and the like.

$C_3$–$C_8$ cycloalkyl means saturated mono cyclic alkyl groups of from 3 to about 8 carbon atoms, and includes such groups as cyclopropyl, cyclopentyl, cyclohexyl, and the like.

$C_1$–$C_{10}$ alkylthio means straight or branched chain thioalkyl groups having from one to about ten atoms selected from C and S and containing one or more S atoms, and includes such groups as thiomethyl, thioethyl, 2-thiopropyl, 2,4-dithiohexyl, 8-methyl-2,4-dithiaethane, and the like.

Halogen includes fluorine, chlorine, bromine and iodine.

Phenyl or a five or six membered heterocyclic ring with from 1 to 4 heteroatoms selected from O, S and N optionally fused to a 5 membered heterocyclic ring containing from 1 to 4 hetero atoms, optionally fused to a phenyl of $Ar^1$, $Ar^2$, Y and $R^4$ includes pyridyl, quinolinyl, pyrimidinyl, pyrrolyl, thienyl, imidazolyl, thiazolyl, benzimidazolyl, thiadiazolyl, benzothiadiazolyl, indolyl, indolinyl, benzodioxolyl, benzodioxanyl, benzothiophenyl, benzoxazinyl, benzisoxazolyl, benzothiazolyl, tetrahydronaphthyl, dihydrobenzofurmayl, tetrahydroquinolinly, fluropyridine, thienopyridine, 2-tetrazolo-[1, 5a] pyridin-6-yl, benzofuranyl, carbazolyl, dibenzothiofuranyl, and the like.

$C_1$–$C_{10}$ heteroalkyl means straight or branched chain heteroalkyl groups having from one to about ten atoms selected from C, N, O, and S and containing at least one hetero atom, and includes such groups as ethers, amines, sulfides and the like.

When any moiety is described as being substituted, it can have one or more of the indicated substituents that can be located at any available position on the moiety. When there are two or more substituents on any moiety, each term shall be defined independently of any other in each occurrence. For example, $NR^1R^1$ may represent $NH_2$, $NHCH_3$, $N(CH_3)CH_2CH_2CH_3$, and the like.

The side chain that begins with the X moiety may be attached to the chroman moiety at any available position on the phenyl portion of the chroman moiety.

Illustrative examples of the compounds of this invention include the following compounds of Formula I:

2-[(2-Hydroxy-2-pyridin-3-yl-ethylamino)-methyl]-chroman-6-sulfonic acid {4-[4-(2-cyclobutyl-ethyl)-5-oxo-4,5-dihydro-tetrazol-1-yl]-phenyl}-amide 2-[(2-Hydroxy-2-pyridin-3-yl-ethylamino)-methyl]-chroman-6-sulfonic acid {4-[4-(2-cyclopentyl-ethyl)-5-oxo-4,5-dihydro-tetrazol-1-yl]-phenyl}-amide 2-[(2-Hydroxy-2-pyridin-3-yl-ethylamino)-methyl]-chroman-6-sulfonic acid {4-[4-(2-cyclohexyl-ethyl)-5-oxo-4,5-dihydro-tetrazol-1-yl]-phenyl}-amide 2-[(2-Hydroxy-2-pyridin-3-yl-ethylamino)-methyl]-chroman-6-sulfonic acid {4-[4-(3-cyclobutyl-propyl)-5-oxo-4,5-dihydro-tetrazol-1-yl]-phenyl}-amide 2-[(2-Hydroxy-2-pyridin-3-yl-ethylamino)-methyl]-chroman-6-sulfonic acid {4-[4-(3-cyclopentyl-propyl)-5-oxo-4,5-dihydro-tetrazol-1-yl]-phenyl}-amide 2-[(2-Hydroxy-2-pyridin-3-yl-ethylamino)-methyl]-chroman-6-sulfonic acid {4-[4-(3-cyclohexyl-propyl)-5-oxo-4,5-dihydro-tetrazol-1-yl]-phenyl}-amide 2-[(2-Hydroxy-2-pyridin-3-yl-ethylamino)-methyl]-chroman-6-sulfonic acid {4-[4-(4-cyclobutyl-butyl)-5-oxo-4,5-dihydro-tetrazol-1-yl]-phenyl}-amide 2-[(2-Hydroxy-2-pyridin-3-yl-ethylamino)-methyl]-chroman-6-sulfonic acid {4-[4-(4-cyclopentyl-butyl)-5-oxo-4,5-dihydro-tetrazol-1-yl]-phenyl}-amide 2-[(2-Hydroxy-2-pyridin-3-yl-ethylamino)-methyl]-chroman-6-sulfonic acid {4-[4-(4-cyclohexyl-butyl)-5-oxo-4,5-dihydro-tetrazol-1-yl]-phenyl}-amide N-{2-[(2-Hydroxy-2-pyridin-3-yl-ethylamino)-methyl]-chroman-6-yl}-4-[4-(2-cyclobutyl-ethyl)-5-oxo-4,5-dihydro-tetrazol-1-yl]-benzenesulfonamide N-{2-[(2-Hydroxy-2-pyridin-3-yl-ethylamino)-methyl]-chroman-6-yl}-4-[4-(2-cyclopentyl-ethyl)-5-oxo-4,5-dihydro-tetrazol-1-yl]-benzenesulfonamide N-{2-[(2-Hydroxy-2-pyridin-3-yl-ethylamino)-methyl]-chroman-6-yl}-4-[4-(2-cyclohexyl-ethyl)-5-oxo-4,5-dihydro-tetrazol-1-yl]-benzenesulfonamide N-{2-[(2-Hydroxy-2-pyridin-3-yl-ethylamino)-methyl]-chroman-6-yl}-4-[4-(3-cyclobutyl-propyl)-5-oxo-4,5-dihydro-tetrazol-1-yl]-benzenesulfonamide N-{2-[(2-Hydroxy-2-pyridin-3-yl-ethylamino)-methyl]-chroman-6-yl}-4-[4-(3-cyclopentyl-propyl)-5-oxo-4,5-dihydro-tetrazol-1-yl]-benzenesulfonamide N-{2-[(2-Hydroxy-2-pyridin-3-yl-ethylamino)-methyl]-chroman-6-yl}-4-[4-(3-cyclohexyl-propyl)-5-oxo-4,5-dihydro-tetrazol-1-yl]-benzenesulfonamide N-{2-[(2-Hydroxy-2-pyridin-3-yl-ethylamino)-methyl]-chroman-6-yl}-4-[4-(4-cyclobutyl-butyl)-5-oxo-4,5-dihydro-tetrazol-1-yl]-benzenesulfonamide N-{2-[(2-Hydroxy-2-pyridin-3-yl-ethylamino)-methyl]-chroman-6-yl}-4-[4-(4-cyclopentyl-butyl)-5-oxo-4,5-dihydro-tetrazol-1-yl]-benzenesulfonamide N-{2-[(2-Hydroxy-2-pyridin-3-yl-ethylamino)-methyl]-chroman-6-yl}-4-[4-(4-cyclohexyl-butyl)-5-oxo-4,5-dihydro-tetrazol-1-yl]-benzenesulfonamide 2-{[2-(6-Amino-pyridin-3-yl)-2-hydroxy-ethylamino]-methyl}-chroman-6-sulfonic acid {4-[4-(2-cyclobutyl-ethyl)-5-oxo-4,5-dihydro-tetrazol-1-yl]-phenyl}-amide 2-{[2-(6-Amino-pyridin-3-yl)-2-hydroxy-ethylamino]-methyl}-chroman-6-sulfonic acid{4-[4-(2-cyclopentyl-ethyl)-5-oxo-4,5-dihydro-tetrazol-1-yl]-phenyl}-amide 2-{[2-(6-Amino-pyridin-3-yl)-2-hydroxy-ethylamino]-methyl}-chroman-6-sulfonic acid {4-[4-(2-cyclohexyl-ethyl)-5-oxo-4,5-dihydro-tetrazol-1-yl]-phenyl}-amide 2-{[2-(6-Amino-pyridin-3-yl)-2-hydroxy-ethylamino]-methyl}-chroman-6-sulfonic acid{4-[4-(3-cyclobutyl-propyl)-5-oxo-4,5-dihydro-tetrazol-1-yl]-phenyl}-amide 2-{[2-(6-Amino-pyridin-3-yl)-2-hydroxy-ethylamino]-methyl}-chroman-6-sulfonic acid{4-[4-(3-cyclopentyl-propyl)-5-oxo-4,5-dihydro-tetrazol-1-yl]-phenyl}-amide 2-{[2-(6-Amino-pyridin-3-yl)-2-hydroxy-ethylamino]-methyl}-chroman-6-sulfonic acid {4-[4-(3-cyclohexyl-propyl)-5-oxo-4,5-dihydro-tetrazol-1-yl]-phenyl}-amide 2-{[2-(6-Amino-pyridin-3-yl)-2-hydroxy-ethylamino]-methyl}-chroman-6-sulfonic acid {4-[4-(4-cyclobutyl-butyl)-5-oxo-4,5-dihydro-tetrazol-1-yl]-phenyl}-amide 2-{[2-(6-Amino-pyridin-3-yl)-2-hydroxy-ethylamino]-methyl}-chroman-6-sulfonic acid {4-[4-(4- cyclopentyl-butyl)-5-oxo-4,5-dihydro-tetrazol-1-yl]-phenyl}-amide

2-{[2-(6-Amino-pyridin-3-yl)-2-hydroxy-ethylamino]-methyl}-chroman-6-sulfonic acid {4-[4-(4-cyclohexyl-butyl)-5-oxo-4,5-dihydro-tetrazol-1-yl]-phenyl}-amide N-(2-{[2-(6-Amino-pyridin-3-yl)-2-hydroxy-ethylamino]-methyl}-chroman-6-yl)-4-[4-(2-cyclobutyl-ethyl)-5-oxo-4,5-dihydro-tetrazol-1-yl]-benzenesulfonamide N-(2-{[2-(6-Amino-pyridin-3-yl)-2-hydroxy-ethylamino]-methyl}-chroman-6-yl)-4-[4-(2-cyclopentyl-ethyl)-5-oxo-4,5-dihydro-tetrazol-1-yl]-benzenesulfonamide N-(2-{[2-(6-Amino-pyridin-3-yl)-2-hydroxy-ethylamino]-methyl}-chroman-6-yl)-4-[4-(2-cyclohexyl-ethyl)-5-oxo-4,5-dihydro-tetrazol-1-yl]-benzenesulfonamide N-(2-{[2-(6-Amino-pyridin-3-yl)-2-hydroxy-ethylamino]-methyl}-chroman-6-yl)-4-(4-(3-cyclobutyl-propyl)-5-oxo-4,5-dihydro-tetrazol-1-yl]-benzenesulfonamide N-(2-{[2-(6-Amino-pyridin-3-yl)-2-hydroxy-ethylamino]-methyl}-chroman-6-yl)-4-[4-(3-cyclopentyl-propyl)-5-oxo-4,5-dihydro-tetrazol-1-yl]-benzenesulfonamide N-(2-{[2-(6-Amino-pyridin-3-yl)-2-hydroxy-ethylamino]-methyl}-chroman-6-yl)-4-[4-(3-cyclohexyl-propyl)-5-oxo-4,5-dihydro-tetrazol-1-yl]-benzenesulfonamide N-(2-{[2-(6-Amino-pyridin-3-yl)-2-hydroxy-ethylamino]-methyl}-chroman-6-yl)-4-[4-(4-cyclobutyl-butyl)-5-oxo-4,5-dihydro-tetrazol-1-yl]-benzenesulfonamide N-(2-{[2-(6-Amino-pyridin-3-yl)-2-hydroxy-ethylamino]-methyl}-chroman-6-yl)-4-[4-(4-cyclopentyl-butyl)-5-oxo-4,5-dihydro-tetrazol-1-yl]-benzenesulfonamide N-(2-{[2-(6-Amino-pyridin-3-yl)-2-hydroxy-ethylamino]-methyl}-chroman-6-yl)-4-[4-(4-cyclohexyl-butyl)-5-oxo-4,5-dihydro-tetrazol-1-yl]-benzenesulfonamide 2-[(2-Hydroxy-2-pyridin-3-yl-ethylamino)-methyl]-chroman-6-sulfonic acid {4-[4-(2-cyclobutyl-ethyl)-2-oxo-2,3-dihydro-imidazol-1-yl]-phenyl}-amide 2-[(2-Hydroxy-2-pyridin-3-yl-ethylamino)-methyl]-chroman-6-sulfonic acid {4-[4-(2-cyclopentyl-ethyl)-2-oxo-2,3-dihydro-imidazol-1-yl]-phenyl}-amide 2-[(2-Hydroxy-2-pyridin-3-yl-ethylamino)-methyl]-chroman-6-sulfonic acid {4-[4-(2-cyclohexyl-ethyl)-2-oxo-2,3-dihydro-imidazol-1-yl]-phenyl}-amide 2-[(2-Hydroxy-2-pyridin-3-yl-ethylamino)-methyl]-chroman-6-sulfonic acid {4-[4-(3-cyclobutyl-propyl)-2-oxo-2,3-dihydro-imidazol-1-yl]-phenyl}-amide 2-[(2-Hydroxy-2-pyridin-3-yl-ethylamino)-methyl]-chroman-6-sulfonic acid {4-[4-(3-cyclopentyl-propyl)-2-oxo-2,3-dihydro-imidazol-1-yl]-phenyl}-amide 2-[(2-Hydroxy-2-pyridin-3-yl-ethylamino)-methyl]-chroman-6-sulfonic acid {4-[4-(3-cyclohexyl-propyl)-2-oxo-2,3-dihydro-imidazol-1-yl]-phenyl}-amide 2-[(2-Hydroxy-2-pyridin-3-yl-ethylamino)-methyl]-chroman-6-sulfonic acid {4-[4-(4-cyclobutyl-butyl)-2-oxo-2,3-dihydro-imidazol-1-yl]-phenyl}-amide 2-[(2-Hydroxy-2-pyridin-3-yl-ethylamino)-methyl]-chroman-6-sulfonic acid {4-[4-(4-cyclopentyl-butyl)-2-oxo-2,3-dihydro-imidazol-1-yl]-phenyl}-amide 2-[(2-Hydroxy-2-pyridin-3-yl-ethylamino)-methyl]-chroman-6-sulfonic acid {4-[4-(4-cyclohexyl-butyl)-2-oxo-2,3-dihydro-imidazol-1-yl]-phenyl}-amide N-{2-[((2-Hydroxy-2-pyridin-3-yl-ethylamino)-methyl]-chroman-6-yl}-4-[4-(2-cyclobutyl-ethyl)-2-oxo-2,3-dihydro-imidazol-1-yl]-benzenesulfonamide N-{2-[((2-Hydroxy-2-pyridin-3-yl-ethylamino)-methyl]-chroman-6-yl}-4-[4-(2-cyclopentyl-ethyl)-2-oxo-2,3-dihydro-imidazol-1-yl]-benzenesulfonamide N-{2-[((2-Hydroxy-2-pyridin-3-yl-ethylamino)-methyl]-chroman-6-yl}-4-[4-(2-cyclohexyl-ethyl)-2-oxo-2,3-dihydro-imidazol-1-yl]-benzenesulfonamide N-{2-[((2-Hydroxy-2-pyridin-3-yl-ethylamino)-methyl]-chroman-6-yl}-4-[4-(3-cyclobutyl-propyl)-2-oxo-2,3-dihydro-imidazol-1-yl]-benzenesulfonamide N-{2-[((2-Hydroxy-2-pyridin-3-yl-ethylamino)-methyl]-chroman-6-yl}-4-[4-(3-cyclopentyl-propyl)-2-oxo-2,3-dihydro-imidazol-1-yl]-benzenesulfonamide N-{2-[((2-Hydroxy-2-pyridin-3-yl-ethylamino)-methyl]-chroman-6-yl}-4-[4-(3-cyclohexyl-propyl)-2-oxo-2,3-dihydro-imidazol-1-yl]-benzenesulfonamide N-{2-[((2-Hydroxy-2-pyridin-3-yl-ethylamino)-methyl]-chroman-6-yl}-4-[4-(4-cyclobutyl-butyl)-2-oxo-2,3-dihydro-imidazol-1-yl]-benzenesulfonamide N-{2-[((2-Hydroxy-2-pyridin-3-yl-ethylamino)-methyl]-chroman-6-yl}-4-[4-(4-cyclopentyl-butyl)-2-oxo-2,3-dihydro-imidazol-1-yl]-benzenesulfonamide N-{2-[((2-Hydroxy-2-pyridin-3-yl-ethylamino)-methyl]-chroman-6-yl}-4-[4-(4-cyclohexyl-butyl)-2-oxo-2,3-dihydro-imidazol-1-yl]-benzenesulfonamide 2-{[2-(6-Amino-pyridin-3-yl)-2-hydroxy-ethylamino]-methyl}-chroman-6-sulfonic acid {4-[4-(2-cyclobutyl-ethyl)-2-oxo-2,3-dihydro-imidazol-1-yl]-phenyl}-amide 2-{[2-(6-Amino-pyridin-3-yl)-2-hydroxy-ethylamino]-methyl}-chroman-6-sulfonic acid{4-[4-(2-cyclopentyl-ethyl)-2-oxo-2,3-dihydro-imidazol-1-yl]-phenyl}-amide 2-{[2-(6-Amino-pyridin-3-yl)-2-hydroxy-ethylamino]-methyl}-chroman-6-sulfonic acid{4-[4-(2-cyclohexyl-ethyl)-2-oxo-2,3-dihydro-imidazol-1-yl]-phenyl}-amide 2-{[2-(6-Amino-pyridin-3-yl)-2-hydroxy-ethylamino]-methyl}-chroman-6-sulfonic acid {4-[4-(3-cyclobutyl-propyl)-2-oxo-2,3-dihydro-imidazol-1-yl]-phenyl}-amide 2-{[2-(6-Amino-pyridin-3-yl)-2-hydroxy-ethylamino]-methyl}-chroman-6-sulfonic acid {4-[4-(3-cyclopentyl-propyl)-2-oxo-2,3-dihydro-imidazol-1-yl]-phenyl}-amide 2-{[2-(6-Amino-pyridin-3-yl)-2-hydroxy-ethylamino]-methyl}-chroman-6-sulfonic acid {4-[4-(3-cyclohexyl-propyl)-2-oxo-2,3-dihydro-imidazol-1-yl]-phenyl}-amide 2-{[2-(6-Amino-pyridin-3-yl)-2-hydroxy-ethylamino]-methyl}-chroman-6-sulfonic acid {4-[4-(4-cyclobutyl-butyl)-2-oxo-2,3-dihydro-imidazol-1-yl]-phenyl}-amide 2-{[2-(6-Amino-pyridin-3-yl)-2-hydroxy-ethylamino]-methyl}-chroman-6-sulfonic acid {4-[4-(4-cyclopentyl-butyl)-2-oxo-2,3-dihydro-imidazol-1-yl]-phenyl}-amide 2-{[2-(6-Amino-pyridin-3-yl)-2-hydroxy-ethylamino]-methyl}-chroman-6-sulfonic acid {4-[4-(4-cyclohexyl-butyl)-2-oxo-2,3-dihydro-imidazol-1-yl]-phenyl}-amide N-(2-{[2-(6-Amino-pyridin-3-yl)-2-hydroxy-ethylamino]-methyl}-chroman-6-yl)-4-[4-(2-cyclobutyl-ethyl)-2-oxo-2,3-dihydro-imidazol-1-yl]-benzenesulfonamide N-(2-{[2-(6-Amino-pyridin-3-yl)-2-hydroxy-ethylamino]-methyl}-chroman-6-yl)-4-[4-(2-cyclopentyl-ethyl)-2-oxo-2,3-dihydro-imidazol-1-yl]-benzenesulfonamide N-(2-{[2-(6-Amino-pyridin-3-yl)-2-hydroxy-ethylamino]-methyl}-chroman-6-yl)-4-[4-(2-cyclohexyl-ethyl)-2-oxo-2,3-dihydro-imidazol-1-yl]-benzenesulfonamide N-(2-{[2-(6-Amino-pyridin-3-yl)-2-hydroxy-ethylamino]-methyl}-chroman-6-yl)-4-[4-(3-cyclobutyl-propyl)-2-oxo-2,3-dihydro-imidazol-1-yl]-benzenesulfonamide N-(2-{[2-(6-Amino-pyridin-3-yl)-2-hydroxy-ethylamino]-methyl}-chroman-6-yl)-4-[4-(3-cyclopentyl-propyl)-2-oxo-2,3-dihydro-imidazol-1-yl]-benzenesulfonamide N-(2-{[2-(6-Amino-pyridin-3-yl)-2-hydroxy-ethylamino]-methyl}-chroman-6-yl)-4-[4-(3-cyclohexyl-propyl)-2-oxo-2,3-dihydro-imidazol-1-yl]-benzenesulfonamide N-(2-{[2-(6-Amino-pyridin-3-yl)-2-hydroxy-ethylamino]-methyl}-chroman-6-yl)-4-[4-(4-cyclobutyl-butyl)-2-oxo-2,3-dihydro-imidazol-1-yl]-benzenesulfonamide N-(2-{[2-(6-Amino-pyridin-3-yl)-2-hydroxy-ethylamino]-methyl}-chroman-6-yl)-4-[4-(4-cyclopentyl-butyl)-2-oxo-2,3-dihydro-imidazol-1-yl]-benzenesulfonamide N-(2-{[2-(6-Amino-pyridin-3-yl)-2-hydroxy-ethylamino]-methyl}-chroman-6-yl)-4-[4-(4-cyclohexyl-butyl)-2-oxo-2,3-dihydro-imidazol-1-yl]-benzenesulfonamide

[(2-{[(2-hydroxy-2-(3-pyridyl)ethyl)amino]methyl}chroman-6-yl)sulfonyl]indan-2-ylamine {[2-({[2-(4-aminophenyl)-2-hydroxyethyl]amino}methyl)chroman-6-yl]sulfonyl}[4-(5-phenyl(1,4,5,6-tetrahydropyrimidinyl))phenyl]amine {[2-({[2-(6-amino(3-pyridyl))-2-hydroxyethyl]amino}methyl)chroman-6-yl]sulfonyl}benzo[c]1,2,5-thiadiazol-4-ylamine {[2-({[2-hydroxy-2-(4-methylphenyl)ethyl]amino}methyl)chroman-6-yl]sulfonyl}[6-(phenylamino)benzothiazol-2-yl]amine {[2-({[2-(4-aminophenyl)-2-hydroxyethyl]amino}methyl)chroman-6-yl]sulfonyl}(4-pyrrolo[2,3-b]pyridinylphenyl)amine

[(2-{[(2-hydroxy-2-(3-pyridyl)ethyl)amino]methyl}chroman-6-yl)sulfonyl][4-(5-methyl(7a-hydro-1,2,4-triazolo[1,5-a]pyrimidin-7-yloxy))phenyl]amine {[2-({[2-(3-chlorophenyl)-2-hydroxyethyl]amino}methyl)chroman-6-yl]sulfonyl}(4-purin-9-ylphenyl)amine {[2-({[2-hydroxy-2-(2-methylphenyl)ethyl]amino}methyl)chroman-6-yl]sulfonyl}[4-(2-(3-pyridyl)piperidyl)phenyl]amine {[2-({[2-(4-aminophenyl)-2-hydroxyethyl]amino}methyl)chroman-6-yl]sulfonyl}pyrimidin-2-ylamine

[(2-{[(2-hydroxy-2-(3-pyridyl)ethyl)amino]methyl}chroman-6-yl)sulfonyl]{4-[(1-methyl-2-phenoxyethyl)amino]phenyl}amine {[2-({[2-(6-amino(3-pyridyl))-2-hydroxyethyl]amino}methyl)chroman-6-yl]sulfonyl}dimethylamine

[(2-{[[(2-hydroxy-2-phenylethyl)amino]methyl}chroman-6-yl)sulfonyl][4-(phenylamino)phenyl]amine {[2-({[2-(4-aminophenyl)-2-hydroxyethyl]amino}methyl)chroman-6-yl]sulfonyl}naphthylamine

[(2-{[(2-hydroxy-2-(3-pyridyl)ethyl)amino]methyl}chroman-6-yl)sulfonyl](2-methylbenzothiazol-5-yl)amine {[2-({[2-(3-chlorophenyl)-2-hydroxyethyl]amino}methyl)chroman-6-yl]sulfonyl}(4-(4-pyridylthio)phenyl)amine {[2-({[2-hydroxy-2-(4-methylphenyl)ethyl]amino}methyl)chroman-6-yl]sulfonyl}(4-morpholin-4-ylphenyl)amine (2-{[(2-hydroxy-2-(3-pyridyl)ethyl)amino]methyl}chroman-6-yl)(naphthylsulfonyl)amine {[2-({[2-(4-aminophenyl)-2-hydroxyethyl]amino}methyl)chroman-6-yl]sulfonyl}butylamine

[(2-{[[(2-hydroxy-2-phenylethyl)amino]methyl}chroman-6-yl)sulfonyl]-3-quinolylamine 1-(3-{[(2-{[(2-hydroxy-2-phenylethyl)amino]methyl}chroman-6-yl)sulfonyl]amino}phenyl)-4-propyl-1,2,3,4-tetraazolin-5-one {[2-({[2-(6-amino(3-pyridyl))-2-hydroxyethyl]amino}methyl)chroman-6-yl]sulfonyl}(4-cyclohexylphenyl)amine (4-butoxyphenyl)[(2-{[[(2-hydroxy-2-(3-pyridyl)ethyl)amino]methyl}chroman-6-yl)sulfonyl]amine {[2-({[2-(4-aminophenyl)-2-hydroxyethyl]amino}methyl)chroman-6-yl]sulfonyl}(phenylethyl)amine 2-{[[(2-hydroxy-2-(3-pyridyl)ethyl)amino]methyl}-6-{[4-benzylpiperidyl]sulfonyl}chromane

[(2-{[(2-hydroxy-2-(3-pyridyl)ethyl)amino]methyl}chroman-6-yl)sulfonyl](1-methylpyrrol-2-yl)amine

[(2-{[(2-hydroxy-2-(3-pyridyl)ethyl)amino]methyl}chroman-6-yl)sulfonyl](4-[(5-nitro(1,3-thiazol-2-yl))amino]phenyl}amine

[(2-{[[(2-hydroxy-2-phenylethyl)amino]methyl}chroman-6-yl)sulfonyl](4-methyl(1,3-thiazol-2-yl))amine {[2-({[2-(4-aminophenyl)-2-hydroxyethyl]amino}methyl)chroman-6-yl]sulfonyl}(3-methylisoxazol-5-yl)amine {[2-({[2-(4-ethylphenyl)-2-hydroxyethyl]amino}methyl)chroman-6-yl]sulfonyl}[4-(1-methyl(1,2,3,4-tetraazol-5-ylthio))phenyl]amine

[(2-{[(2-hydroxy-2-(3-pyridyl)ethyl)amino]methyl}chroman-6-yl)sulfonyl][4-(5-phenyl(1,2,3,4-tetraazolyl))phenyl]amine {[2-({[2-(6-amino(3-pyridyl))-2-hydroxyethyl]amino}methyl)chroman-6-yl]sulfonyl}[4-(1,3,4-thiadiazol-2-ylamino)phenyl]amine

[(2-{[(2-hydroxy-2-(3-pyridyl)ethyl)amino]methyl}chroman-6-yl)sulfonyl]{4-[(5-nitro(1,3-thiazol-2-yl))amino]phenyl}amine

[(2-{[[(2-hydroxy-2-phenylethyl)amino]methyl}chroman-6-yl)sulfonyl](4-methyl(1,3-thiazol-2-yl))amine {[2-({[2-(4-aminophenyl)-2-hydroxyethyl]amino}methyl)chroman-6-yl]sulfonyl}(3-methylisoxazol-5-yl)amine {[2-({[2-(4-ethylphenyl)-2-hydroxyethyl]amino}methyl)chroman-6-yl]sulfonyl][4-(1-methyl(1,2,3,4-tetraazol-5-ylthio))phenyl]amine

[(2-{[(2-hydroxy-2-(3-pyridyl)ethyl)amino]
methyl}chroman-6-yl)sulfonyl][4-(5-phenyl(1,2,3,4-tetraazolyl))phenyl]amine {[2-({[2-(6-amino(3-pyridyl))-2-hydroxyethyl]
amino}methyl)chroman-6-yl]sulfonyl}[4-(1,3,4-thiadiazol-2-ylamino)phenyl]amine {[2-({[2-(6-amino(3-pyridyl))-2-hydroxyethyl]
amino}methyl)chroman-6-yl]sulfonyl}[6-(propylamino)benzothiazol-2-yl]amine As is true of most classes of therapeutically effective compounds, certain subclasses and certain species which are especially effective are preferred over others. In this instance, those compounds of Formula I which are preferred include those compounds where $Ar^1$ is pyridine and R is hydrogen or amine; X is either $NHSO_2$ or $SO_2NH$; $Ar^2$ is phenyl; Y is a 5 membered nitrogen containing heterocyclic ring; and $R^4$ is $C_2$–$C_4$ alkyl substituted with $C_3$–$C_8$ cycloalkyl, most preferably, with cyclopentyl.

Representative salts of the compounds of Formula I include the conventional non-toxic salts and the quaternary ammonium salts which are formed, for example, from inorganic or organic acids or bases. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconoate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine salts and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, luaryl, myristyl and strearyl chlorides, bromides and iodides, aralkyl halides like benzyl and phenethyl bromides and others.

The esters in the present invention are non-toxic, pharmaceutically acceptable esters such as alkyl esters such as methyl, ethyl, propyl, isopropyl, butyl, isobutyl or pentyl esters. Additional esters such as phenyl-$C_1$–$C_5$ alkyl may be used. The compound of Formula I may be esterified by a variety of conventional procedures including reacting the appropriate anhydride, carboxylic acid or acid chloride with the alcohol group of the Formula I compound. The appropriate anhydride is reacted with the alcohol in the presence of an acylation catalyst such as 1,8-bis[dimethylamino]napthalene or N,N-dimethylaminopyridine. An appropriate carboxylic acid can be reacted with the alcohol in the presence of a dehydrating agent such as dicyclohexylcarbodiimide, 1-[3-dimethylaminopropyl]-3-ethylcarbodiimide or other water soluble dehydrating agents which are used to drive the reaction by the removal of water, and, optionally, an acylation catalyst. Esterification can also be reached using the appropriate carboxylic acid in the presence of trifluoroacetic anhydride and, optionally, pyridine, or in the presence of N,N-carbonyldiimidazole with pyridine. Reaction of an acid chloride with the alcohol is carried out with an acylation catalyst such as 4-DMAP or pyridine.

Sensitive or reactive groups on the compound of Formula I may need to be protected during any of the above methods for forming esters, and protecting groups may be added and removed by conventional methods well known in the art.

One skilled in the art would readily know how to successfully carry out these as well as other methods of esterification of alcohols.

The compounds of this invention may, either by nature of asymmetric centers or by restricted rotation, be present in the form of isomers. All isomers, whether separated, pure, partially pure or in racemic mixture, of the compounds of this invention are encompassed within the scope of this invention. The compounds of Formula I wherein the hydroxy component on the $Ar^1$ side chain is in the R configuration (above the plane as drawn) is preferred. The purification of said isomers and the separation of said isomeric mixtures can be accomplished by standard techniques known in the art.

The particular process to be utilized in the preparation of the compounds of this invention depends upon the specific compound desired. Such factors as the selection of the specific Ar, X, Y and $R^4$ moieties, and the specific substituents on the various moieties, all play a role in the path to be followed in the preparation of the specific compounds of this invention. Those factors are readily recognized by one of ordinary skill in the art.

The compounds of Formula I of the present invention can be prepared as indicated in the following Reaction Schemes.

In general, the compounds of this invention may be prepared by standard techniques known in the art and by known processes analogous thereto. The compounds of Formula I can generally be synthesized according to Reaction Scheme 1 wherein the appropriate epoxide 1 is coupled with the appropriate amine 2. This reaction is typically carried out in an aprotic solvent such as dimethyl sulfoxide, dimethyl formamide, acetonitrile, or in an alcohol such as ethanol, isopropanol or propanol at temperature from about −10° C. to reflux.

REACTION SCHEME 1

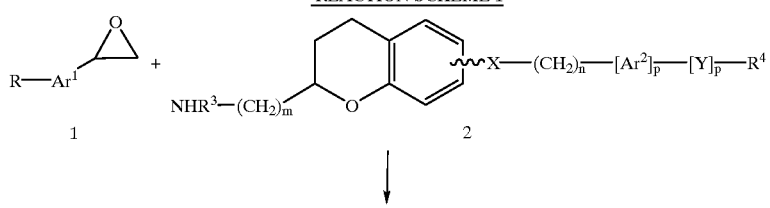

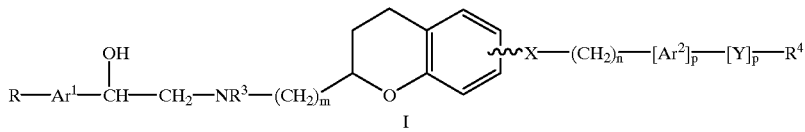

One skilled in the art will recognize that the use of protecting groups may be required for the synthesis of compounds containing certain substituents. A description of suitable protecting groups and appropriate methods of removing such groups may be found in: *Protective Groups in Organic Synthesis*, Second Edition, T. W. Greene, John Wiley and Sons, New York, 1991. For example, after preparation of a compound according to Reaction Scheme 1, in order to enable purification of the end product by, for instance, flash chromatography, compounds of Formula I wherein $R^3$ is, for example, H can be selectively protected as, for example, a carbamate derivative obtained by, for example, treatment with a reagent such as di-tert-butyl dicarbonate or other means known in the art. After purification, the carbamate group can easily be removed by treatment with an acid such as hydrochloric acid or trifluoroacetic acid by means known in the art.

The epoxide 1 of Reaction Scheme 1 is commercially available or may be prepared according to one of the many procedures described in the literature known to those skilled in the art. A representative synthesis of epoxide 1 is outlined in Reaction Scheme 2. Arylketone 3 can be halogenated with a reagent such as N-chlorosuccinimide (NCS) in a protic solvent such as acetic acid/hydrochloric acid mixture (HCl) to afford the chloroacetyl 4. Treatment of 4 by a reducing agent such as sodium borohydride ($NaBH_4$) in a polar solvent such as methanol (MeOH), gives the corresponding alcohol 5. The epoxide 1a can be obtained by treating alcohol 5 with a base such as potassium carbonate ($K_2CO_3$) in a solvent such as acetone.

In this particular synthesis, compounds 5 and 1a are both racemic and the pure enantiomeric form of each compound can be obtained by chiral chromatography. It may be appreciated by one skilled in the art that there are several methods which can produce enantiomerically enriched (R) or (S) epoxide 1a by asymmetric reduction of the haloketone 4. Asymmetric reduction can be accomplished using chiral reducing agents such as, but not limited to, (−) or (+)-DIP-CI and (R) or (S)-Alpine borane.

An alternative synthesis of epoxide 1 wherein $Ar^1$ is a pyridine ring fused to a 5 membered heterocyclic ring containing 4 nitrogen atoms (1b) is outlined in Reaction Scheme 3. Chlorinated 3-acetyl-pyridine 7 can be obtained from treating the acyl chloride 6 with dimethylmalonate, a reagent such as magnesuim chloride and a base such as triethylamine ($CH(CO_2Me)_2$, $Et_3N$, $MgCl_2$). The intermediate can undergo a decarboxylation at high temperature in a polar solvent such as dimethylsulfoxide (DMSO), according to a procedure described by Kuo (*Tetahedron*, 1992, 48, 9233). Treatment of 7 with sodium azide ($NaN_3$) in a polar solvent such as methanol in the presence of an acid such as hydrochloric acid (HCl), affords the corresponding tetrazolopyridine 8. The ketone 8 can be halogenated with a reagent such as N-bromosuccinimide (NBS) in a protic solvent such as acetic acid/HBr mixture (AcOH/HBr) to afford the bromoacetyl 9. Treatment of 9 by a reducing agent such as sodium borohydride ($NaBH_4$) in a polar solvent such as methanol, followed by an in situ treatment with a base such as sodium hydroxide (NaOH) affords the epoxide 1b.

By analogy to the synthesis of epoxide 1a, epoxide 1b can be obtained in its pure enantiomeric form by asymmetric reduction of the haloketone 9, using the chiral reagents previously described.

The epoxide 1b may be used according to Reaction Scheme 1 to produce the compound of Formula I wherein $Ar^1$ is a pyridine ring fused to a 5 membered heterocyclic ring containing 4 nitrogen atoms, and may be further treated by methods known in the art to cleave the fused heterocyclic ring from the 6 membered ring, resulting in the compounds of Formula I wherein $Ar^1$ is pyridine substituted with $NH_2$.

REACTION SCHEME 2

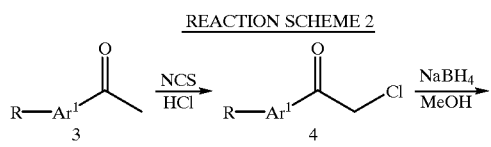

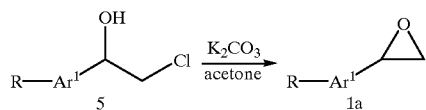

REACTION SCHEME 3

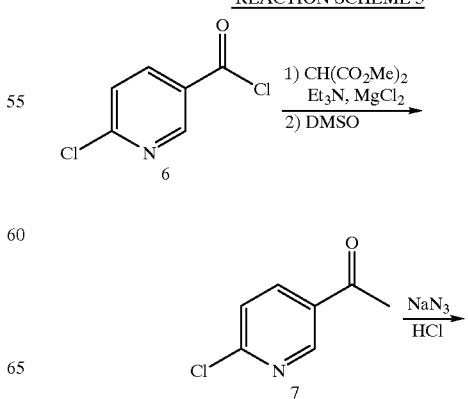

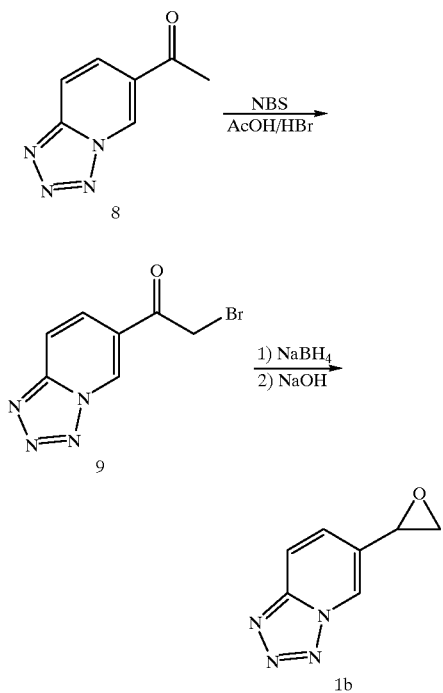

using a catalyst such as palladium on activated carbon (Pd/C) gives the chroman 12. The chroman-carboxylic acid 12 can be converted by a stepwise procedure to the amide 13 with a reagent such as oxalyl chloride ($(COCl)_2$) followed by a treatment with ammonia ($NH_3$). The amide 13 is then treated with chlorosulfonic acid ($ClSO_3H$) without solvent to afford the chroman-sulfonyl chloride 14 mainly substituted at the position 6. Other methods known to one skilled in the art may allow different substitution patterns, for example, the starting material hydroxyacetophenone 10 could be substituted at any of the aromatic positions by a functional group that can later be transformed to other regioisomers of the chroman-sulfonyl chloride 14, using the same or similar reaction sequence. Coupling of the amine 15 with the sulfonyl chloride 14 can be accomplished in an inert solvent such as THF with a base such as pyridine to afford the sulfonamide 16. Chemical reducing agents such as borane dimethyl sulfide ($BH_3.Me_2S$) or sodium bis(2-methoxyethoxy)aluminum in an inert solvent such as THF can selectively reduce the amide 16 to give the primary amine 2a.

Within the class of amine 15 of Reaction Scheme 4, many are commercially available. In particular, substituted anilines are good examples of such readily available amines. However, several may require a synthetic preparation. Other representative syntheses of amines 15 are outlined in Reaction Schemes 6, 7, 8, 11, 12, 17, 18, and 19.

REACTION SCHEME 4

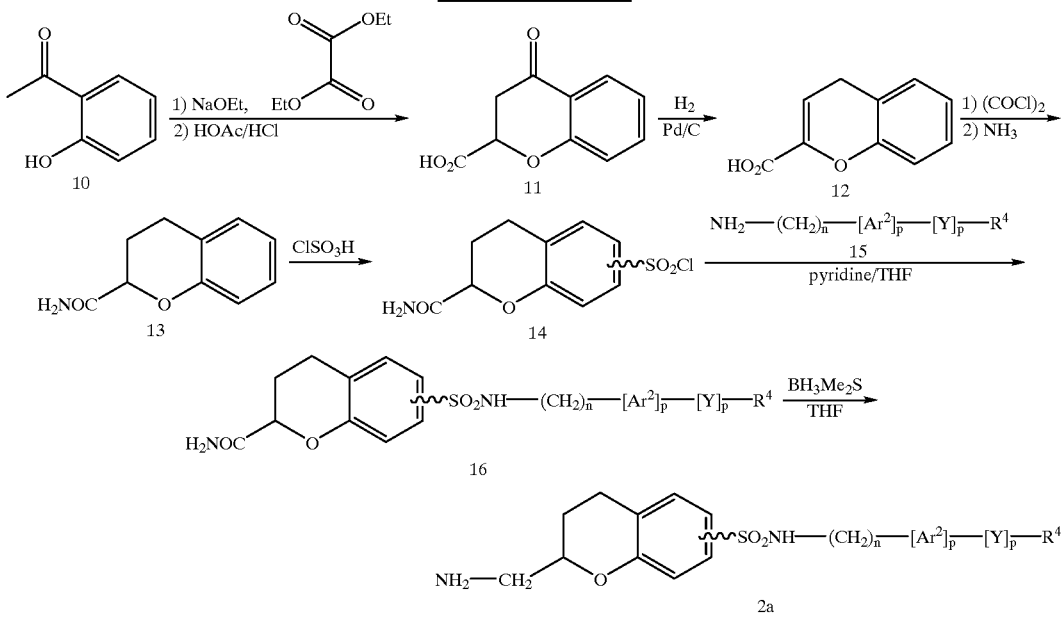

A representative synthesis of the amine 2 of Reaction Scheme 1 wherein X is $SO_2NH$ (2a) is outlined in Reaction Scheme 4. The hydroxyacetophenone 10 (commercially available) is treated with diethyl oxalate in a presence of a base such as sodium ethoxide (NaOEt) in a polar solvent such as ethanol. After work-up, the residue can be treated with a mixture of acetic acid and hydrochloric acid (HOAc/HCl), to afford the carboxylic acid 11. Hydrogenation of 11

A representative synthesis of the amine 2 wherein X is $NHSO_2$ (2b) is outlined in Reaction Scheme 5. Chroman 12 can undergo nitration with a strong acid such as concentrated nitric acid ($HNO_3$) to give the carboxylic acid 17, mainly substituted at the position 6. Other methods known to one skilled in the art may allow different substitution pattern, for example, the starting material (hydroxyacetophenone 10) could be substituted at any of the aromatic position by a functional group that can later be transformed to other regioisomers of the nitro-chroman 17, using the same or similar reaction sequence. The chroman-carboxylic acid 17 can be converted by a stepwise procedure to the amide 18 with a reagent such as oxalyl chloride (($COCl)_2$) followed by a treatment with ammonia ($NH_3$). Reduction of the nitro group to the corresponding amine can be accomplished with standard hydrogenation procedure using a catalyst such as palladium on activated carbon (Pd/C) to give the amine 19. Coupling of the sulfonyl chloride 20 with the amine 19 can be accomplished in an inert solvent such as THF with a base such as pyridine to afford the sulfonamide 21. Chemical reducing agents such as borane dimethyl sulfide ($BH_3.Me_2S$) in an inert solvent such as THF can selectively reduce the amide 21 to give the primary amine 2b.

Compound 2 of Reaction Scheme 1 wherein m is other than one can be synthesized from derivatives of compound 12. For example, compound 12 can be reduced to the corresponding alcohol by treatment with a reducing agent such as lithium aluminum hydride. The resulting alcohol can then be oxidized to the corresponding aldehyde by treatment with an oxidizing reagent such as PCC (pyridinium chlorochromate) in an appropriate solvent. The resulting aldehyde can undergo an alkyl chain extension according to well known procedures such as that described by Wittig, G. et al., in *Chem. Ber.*, 1962, 2514. This aldehyde with the extended alkyl chain can be converted to a carboxyclic acid by standard methods of oxidation well known by those skilled in the art, and can be used in place of compound 12 to make compound 2 of Reaction Scheme 1 by analogy to compound 12 in Reaction Schemes 4 and 5.

Within the class of sulfonyl chloride 20 of Reaction Scheme 5, many are commercially available. However, several may require a synthetic preparation using a reagent such as chlorosulfonic acid according to procedures known to those skilled in the art including that described in *Org. Synthesis*, 1, 8. A further example of making sulfonyl chloride 20 is illustrated in Reaction Scheme 14.

The representative preparation of amines 15 of Reaction Scheme 4 wherein $R^4$ is optionally substituted $C_1$–$C_{10}$ alkyl Y is tetrazolone, n is 0 and p is 1 in both instances (15a) is described in Reaction Scheme 6. Phenyl-tetrazolone 22, synthesized according to the procedure described by Horwitz (*JACS*, 1959, 81, 3076), can undergo nitration with a reagent such as concentrated nitric acid ($HNO_3$) to give the nitroaryl 23. Compound 23 can be treated with a base such as potassium hydroxide (KOH) and an alkyl halide such as 1-bromopropane, in a polar solvent such as dimethylformamide (DMF), to afford the alkylated tetrazolone 24. Tetrazolone 24 can then be treated with hydrogen ($H_2$) in the presence of a metal catalyst, such as palladium on carbon (Pd/C), in a polar solvent, such as ethanol, to give amine 15a.

REACTION SCHEME 6

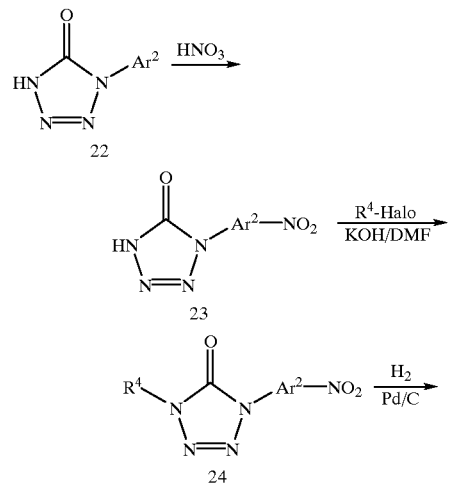

REACTION SCHEME 5

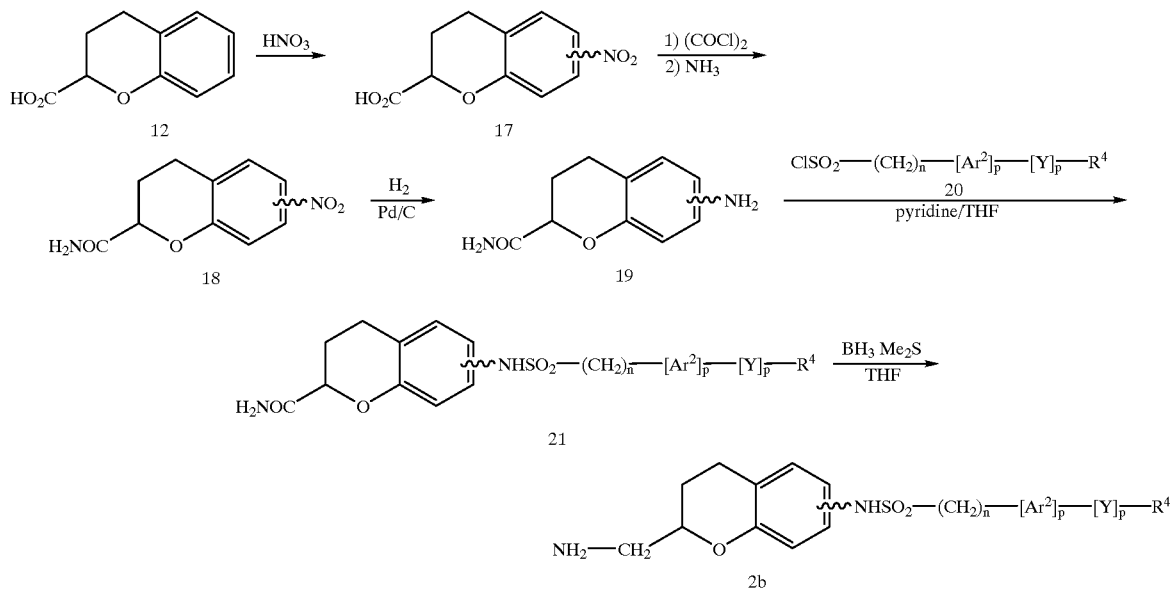

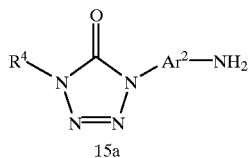

Another representative synthesis of a specific amine 15 wherein $R^4$ is $C_1-C_{10}$ alkyl substituted with $C_3-C_8$ cycloalkyl and Y is cyclic urea, n is 0 and p is 1 in both instances (15b) is outlined in Reaction Scheme 7. Aminoacetal 25 is alkylated with a alkyl halide such as 3-cyclopentyl-1-iodopropane and with a base such as potassium carbonate ($K_2CO_3$) in a polar solvent such as dimethylformamide (DMF), to afford the alkylated amine 26. The amine 26 can undergo cyclization by a stepwise procedure. Treatment of amine 26 with an appropriate isocyanate such as 4-nitrophenyl isocyanate followed by a treatment with an acid such as trifluoroacetic acid (TFA) gives the cyclic urea 27. The cyclic urea 27 can be treated with hydrogen ($H_2$) in the presence of a metal catalyst such as palladium on carbon (Pd/C) in a polar solvent, such as ethanol, to give amine 15b. Alternatively, reduction of urea 27 to amine of type 15b may also be accomplished using a reducing agent such as tin chloride dihydrate in a solvent such as ethanol at elevated temperature.

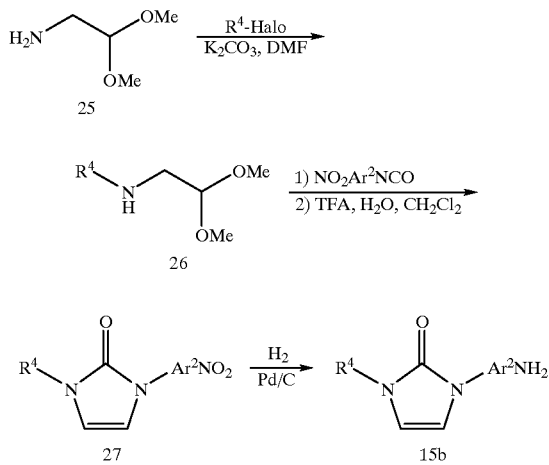

Alternatively, amine 15 can be substituted by various groups on the aromatic $Ar^2$ ring (15c). A representative synthesis in which $Ar^2$ is substituted by a methoxy is outlined in Reaction Scheme 8. The commercially available arylamine 28 can be treated with a reagent such as phosgene to produce the isocyanate 29. Treatment of the isocyanate 29 with a reagent such as sodium azide can produce the tetrazolone 30. Treatment of the tetrazole 30 with a base such as sodium hydride and an alkyl halide ($R^4$-halo) such as alkyl bromide, in a polar solvent such as dimethylformamide, can afford the alkylated tetrazolone 31. Tetrazolone 31 can then be treated with hydrogen in the presence of a metal catalyst, such as palladium on carbon, in a polar solvent, such as ethanol, to give amine 15c.

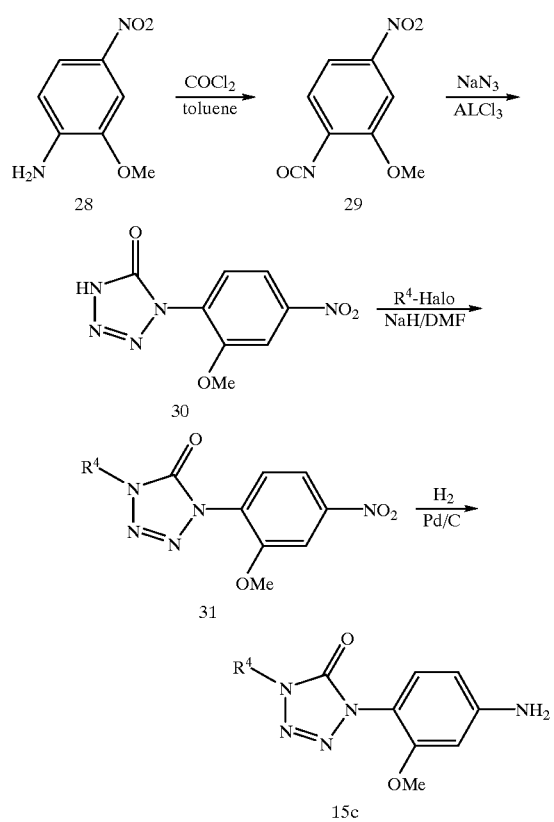

The compounds of Formula I may also be synthesized according to Reaction Scheme 9 wherein carboxylic acid 32 (synthesis of which is described in Reaction Scheme 10 and 13) is coupled with alcohol 33 to afford amide 34, which is in turn, reduced to compound of Formula I. The coupling reaction is typically carried out in an aprotic solvent such as dichloromethane ($CH_2Cl_2$), tetrahydrofuran, or acetonitrile. A coupling reagent such as 1-(3-dimethylaminopropyl)-3-ethylcarbodiimide hydrochloride (EDCl), benzotriazol-1-yloxytris(dimethylamino)phosphonium hexafluorophosphate (BOP reagent), O-(7-azabenzotriazol-1-yl)-N,N,N',N'-tetramethyluronium hexafluorophosphate (HATU), 1,1'-carbonyldiimidazole (CDI), or bis(2-oxo-3-oxazolidinyl) phosphinic chloride (BOP-Cl) is employed along with an organic base such as triethylamine ($NEt_3$) or N-methylmorpholine and optionally with a reagent such as 1-hydroxybenzotriazole (HOBT) or 1-hydroxy-7-azabenzotriazole (HOAT). The chroman 34 is then reduced to the chroman Formula I by a reducing agent such as borane dimethyl sulfide complex ($BH_3 \cdot Me_2S$) or sodium bis(2-methoxyethoxy)aluminum in an inert solvent such as tetrahydrofuran (THF). Compounds of Formula I where R is 2,5-dimethylpyrrolidyl can be further transformed to the corresponding primary amine by treatment with a reagent such as hydroxylamine hydrochloride in a mixture of solvents such as ethanol and water. The coupling and reduction sequence described in Reaction Scheme 9 is an alternative synthesis of compounds of Formula 1 described in Reaction Scheme 1, which may offer some advantages such as yields or ease of purification.

REACTION SCHEME 9

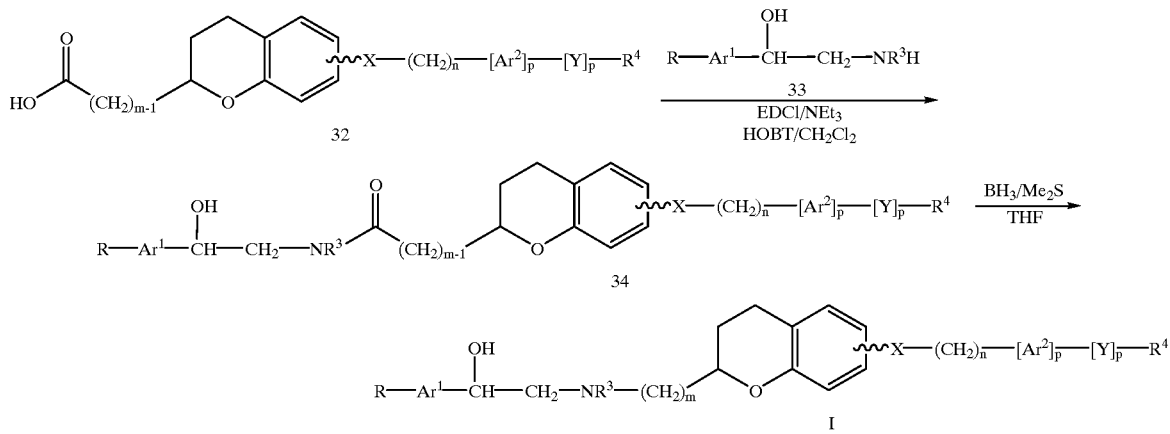

Carboxylic acid 32a wherein X is $SO_2NH$ may be synthesized according to Reaction Scheme 10 in which chroman-2-carboxylic acid 12 is treated with an alkylating agent such as isobutyl iodide or isobutyl bromide in the presence of an inorganic or organic base such as cesium carbonate, sodium carbonate, or potassium carbonate in a solvent such as N,N-dimethylformamide (DMF) to provide carboxylic ester 35. Treatment is of 35 with chlorosulfonic acid in an aprotic solvent such as dichloromethane or dichloroethane, provides sulfonyl chloride 36. Condensation of sulfonyl chloride 36 with amine 15 in the presence of an inorganic or organic base such as pyridine and a catalytic amount of an acylating agent such as 4-dimethylaminopyridine (DMAP) in an aprotic solvent such as tetrahydrofuran (THF) provides sulfonamide 37. Saponification of ester 37 using a reagent such as sodium hydroxide in a solvent such as methanol followed by treatment with an inorganic acid such as hydrochloric acid results in generation of carboxylic acid 32a.

REACTION SCHEME 10

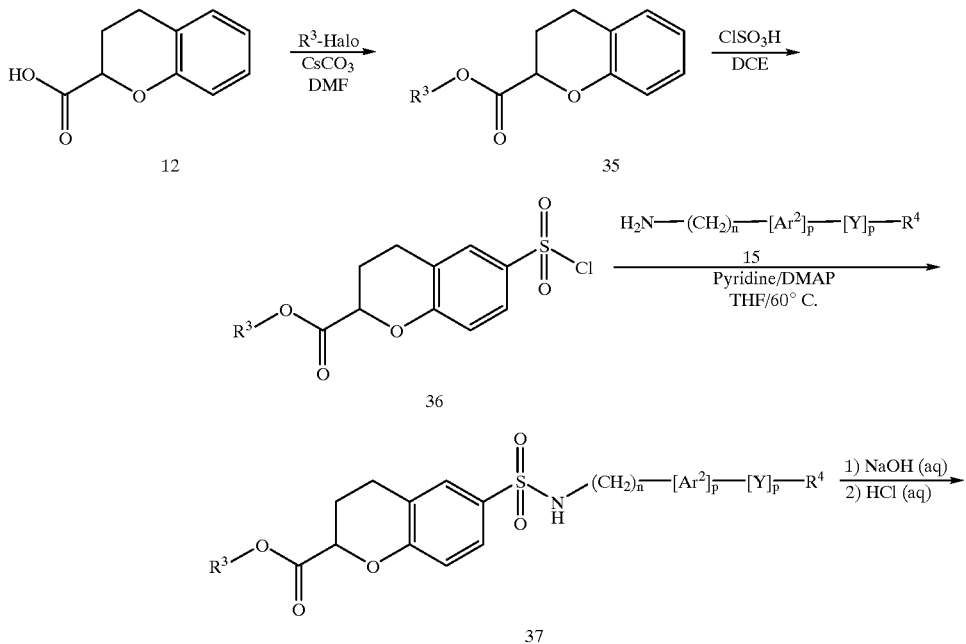

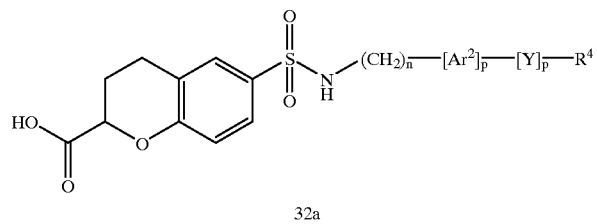

32a

The carboxylic acid 12 may be racemic or enriched to any degree in either the R- or S-chroman-2-carboxylic acid. The synthetic processes used to transform chroman-2-carboxylic acid 12 to carboxylic acid 32a, as described in Reaction Scheme 10, and subsequently to compounds of Formula I, as described in Reaction Scheme 9, do not compromise the stereochemical integrity of the 2 position of the chroman.

An alternative synthesis of amine 15 where $Ar^2$ is optionally substituted phenyl or any optionally substituted heterocycle, $R^4$ is most defined groups, and Y is tetrazole is shown in Reaction Scheme 11. Treatment of compound 38 (usually commercially available) such as phenyl chlorotetrazole, with fuming nitric acid provides nitrated compound 39. Treatment of 39 with an alcohol ($R^4OH$) in the presence of an inorganic base such as sodium hydride in a solvent such as tetrahydrofuran (THF) results in formation of the ether 40. Reaction of 40 with sodium iodide in a solvent such as N,N-dimethylformamide (DMF) provides the nitro compound 24. Reduction of 24, for example by catalytic hydrogenation using a hydrogen atmosphere and a catalyst such as palladium on activated carbon in a solvent such as ethanol, provides amine 15a.

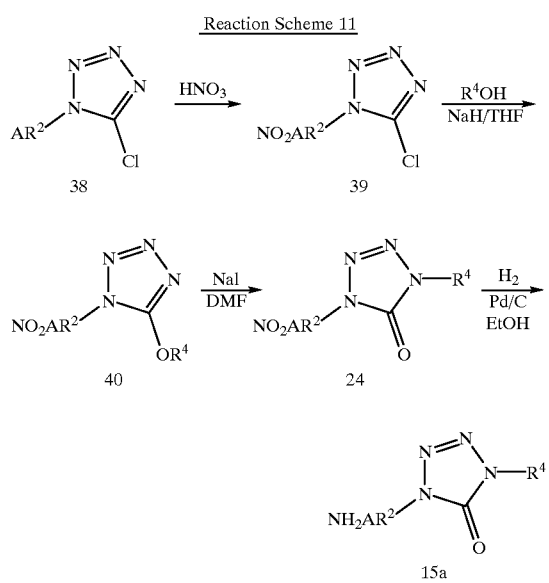

Tetrazolone 24 can also be obtained directly from compound 39 in a one step process, using the same reagents reported in Reaction Scheme 11, in a solvent such as DMF.

Alternatively, amine 15 of Reaction Scheme 10 where where $Ar^2$ is optionally substituted phenyl or any optionally substituted heterocycle, R is unsaturated $C_1$–$C_{10}$ alkyl, and Y is tetrazolone may be synthesized as shown in Reaction Scheme 12. Treatment of chlorinated compound 39 with allylic alcohol 41 in the presence of an inorganic base such as sodium hydride in a solvent such as tetrahydrofuran results in formation of tetrazolone 24a. R can be further transformed to most any $R^4$ group by means well known in the art. Reduction as described in Reaction Scheme 11 provides amine of type 15.

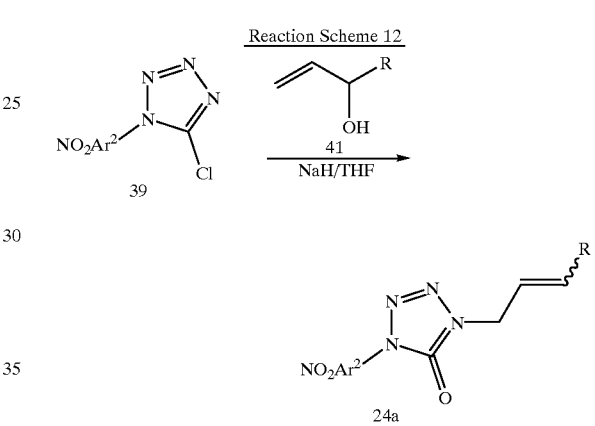

Another synthesis of carboxylic acid 32 where X is $NHSO_2$ is shown in Reaction Scheme 13, in which chroman-2-carboxylic acid ester 35 is treated with a nitrating reagent such as nitric acid to provide nitrochroman 42. Nitrochroman 42 can be reduced to the corresponding aniline 43 by hydrogen in the presence of a catalytic amount of palladium on activated carbon, in a solvent such as ethyl acetate or an alcohol such as ethanol. Treatment of aniline 43 with a sulfonyl chloride 20 in the presence of an inorganic or organic base such as pyridine and a catalytic amount of an acylating agent such as 4-dimethylaminopyridine (DMAP), in an aprotic solvent such as tetrahydrofuran (THF) provides sulfonamide 44. Saponification of ester 44 using a metal hydroxide such as sodium hydroxide in a solvent such as methanol followed by treatment with an inorganic acid such as hydrochloric acid, gives carboxylic acid 32b.

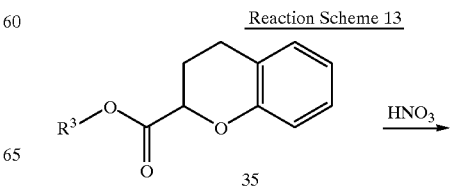

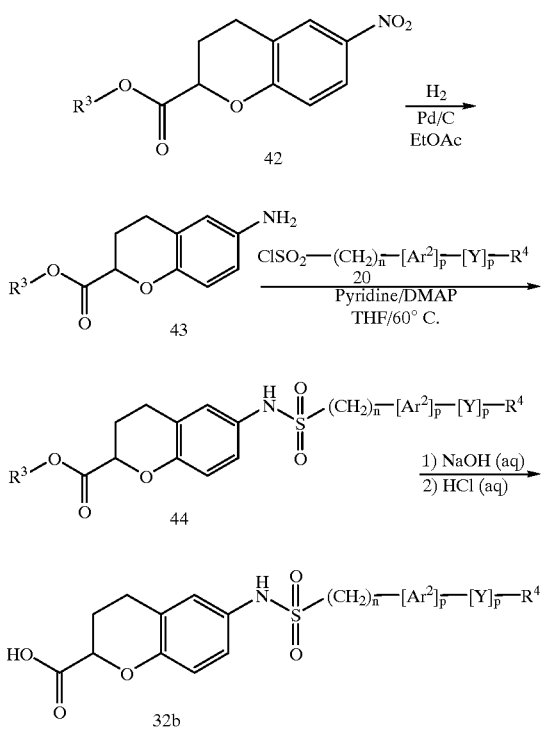

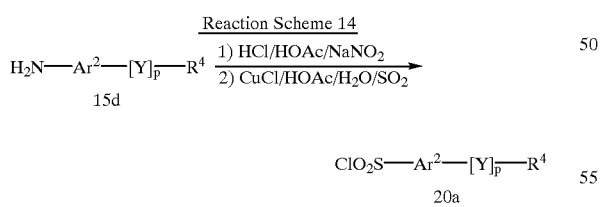

Chroman carboxylic acid 35 may be racemic or enriched to any degree in either the R- or S-chroman-2-carboxylic acid. The synthetic processes used to transform chroman-2-carboxylic acid 35 to carboxylic acid 32b, as described in Reaction Scheme 13, and subsequently to compounds of Formula I, as described in Reaction Scheme 9, do not compromise the stereochemical integrity of the 2 position of the chroman.

Sulfonyl chloride 20 of Reaction Scheme 13 where n is 0 may be synthesized as shown in Reaction Scheme 14. Treatment of amine 15d with a mixture of hydrochloric acid, acetic acid, and aqueous sodium nitrite followed by treatment with an aqueous mixture of copper (I) chloride, acetic acid, and sulfur dioxide provides sulfonyl chloride 20a.

Amines 33 of Reaction Scheme 9 are commercially available or, where $Ar^1$ is optionally substituted pyridyl or most other defined heterocycles, may be synthesized according to Reaction Scheme 15. Brominated amine 45 is treated with hexane-2,5-dione and an acid such as acetic acid in an inert solvent such as cyclohexane with azeotropic removal of water to provide pyrrole 46 (J. Chem. Soc., 1984, 2801). Pyrrole 46 may be reacted with a metal such as magnesium in the presence of a catalytic amount of iodine or 1,2-diiodoethane, in an inert solvent such as tetrahydrofuran, followed by treatment with methoxyacetamide 47 resulting in formation of ketone 48. Reduction of ketone 48 to chlorinated alcohol 49 is accomplished with an achiral or chiral reducing agent in an inert solvent such as tetrahydrofuran. When a chiral reducing agent is employed the resulting alcohol may be enriched to any degree in one or the other enantiomer. For example, when the reducing agent is R-Alpine-Borane® the resulting alcohol 49 is enriched in the R enantiomer when $Ar^1$ is not $Ar^1OCH2$ but is an aromatic ring. Treatment of chloride 49 with potassium phthalimide in an inert solvent such as N,N-dimethylformamide affords phthalimide 50. Reaction of phthalimide 50 with hydrazine monohydrate in a solvent such as ethanol followed by treatment with hydrochloric acid results in formation of hydroxylamine dihydrochloride 33a.

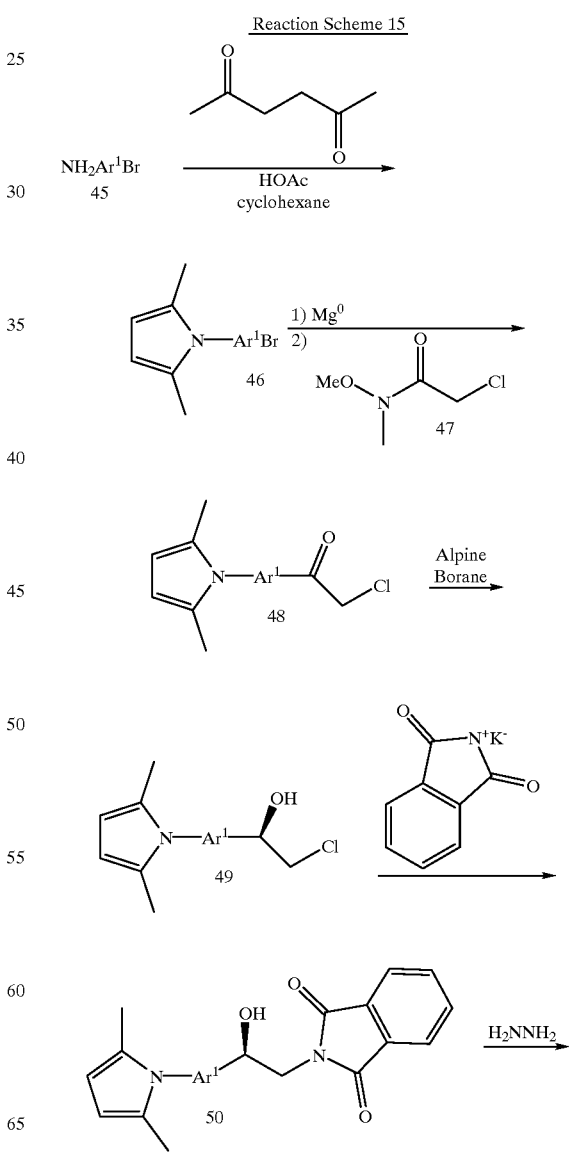

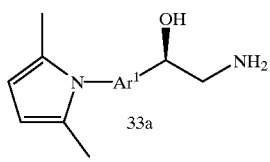

Methoxyacetamide 47 is synthesized according to Reaction Scheme 16 in which an haloacetyl chloride is treated with methoxymethylamine in the presence of a base such as potassium carbonate in a solvent mixture consisting of an organic solvent such as tert-butyl methyl ether and water.

Reaction Scheme 16

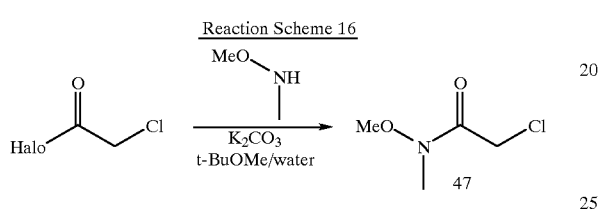

Another representative preparation of amine 15 of Reaction Scheme 10 where the carbon atom of the appropriate $R^4$ group of compound 51 that is attached to the alcohol is not sterically hindered is described in Reaction Scheme 17. Treatment of tetrazolone 23 with an alcohol such as hydroxyethyl phenyl sulfide 51 in the presence of triphenylphosphine ($PPh_3$) and diethyl azodicarboxylate (DEAD) in an inert solvent such as tetrahydrofuran (THF) affords compound 24c. Reduction of the aromatic nitro group using standard conditions as described in Reaction Scheme 13 provides amine 15a.

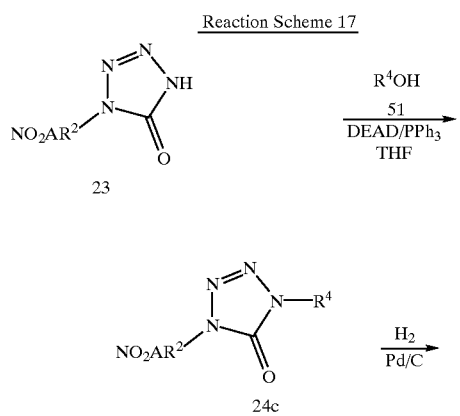

Another representative preparation of amine 15 where Y is tetrazole, is described in Reaction Scheme 18. Treatment of tetrazole 52 with an alkylating agent such as 3-cyclopentyl-1-iodopropane in the presence of a base such as sodium hydride (NaH) in an inert solvent such as N,N-dimethylformamide (DMF) affords tetrazole 53. Reduction of the aromatic nitro group using standard conditions as described in Reaction Scheme 13 provides amine 15d.

Reaction Scheme 18

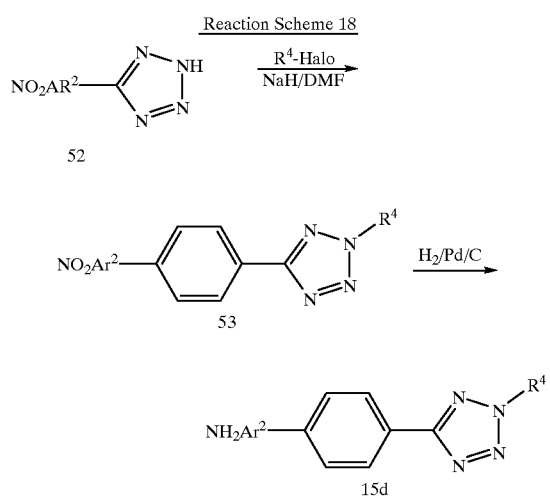

Another representative preparation of amine 15 where $Ar^2$, Y and $R^4$ can be any appropriate defined group, is described in Reaction Scheme 19. Compound 54 is readily available or can be prepared by methods known by those skilled in the art or by, for example, nitration of a florinated aromatic as shown in Reaction Scheme 11. Alcohol 55 is also commercially available or can be made by known methods such as by reducing a known ester using a reagent such as lithium aluminum hydride to directly provide the alcohol. Reaction of florinated 54 with alcohol 55 in the presence of a base such as potassium carbonate in an inert solvent such as N,N-dimethylformamide (DMF) results in formation of ether 56. Reduction of the aromatic nitro group using standard conditions as described in Reaction Scheme 13 provides amine 15e.

Reaction Scheme 19

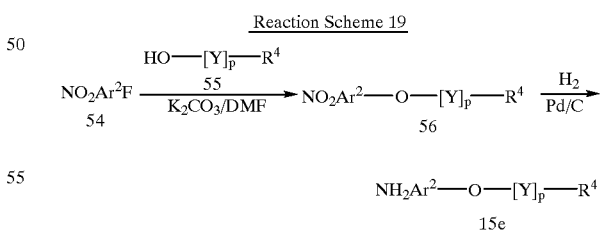

Another synthesis of compounds of Formula I where X is $SO_2$-piperazinyl or $SO_2$—$NR_3$, can be synthesized according to Reaction Scheme 10 using intermediates 57 or 58 described in Reaction Scheme 20 where the chlorosulfonyl chroman 36 is treated with a base such as 4-dimethylaminopyridine (DMAP) and an amine such as 59 or 60 in an aprotic solvent such as tetrahydrofuran (THF) provide sulfonamides 57 or 58.

Reaction Scheme 20

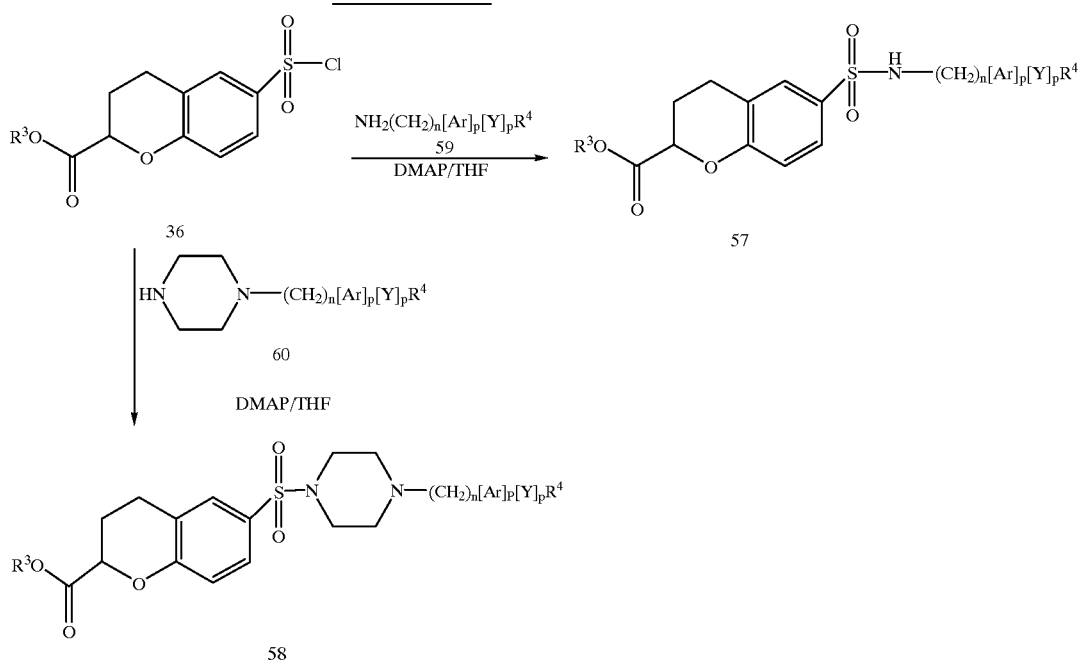

The foregoing reaction schemes are further illustrated by the specific Examples described later herein.

The salts and esters of this invention can be readily prepared by conventional chemical processes as described previously.

The compounds of Formula I of this invention are beta-3 adrenergic receptor agonists, preferably selective beta-3 adrenergic receptor agonists, that effect beta-3 adrenergic receptor mediated conditions without concurrent beta-1 and/or beta-2 receptor mediated side effects. Accordingly, an embodiment of the present invention is the administration of the compounds of this invention to a human or animal for the treatment of beta-3 receptor mediated conditions such as diabetes, obesity, gastrointestinal disorders including irritable bowel syndrome and intestinal hypermotility disorders, peptic ulcerations, esophagitis, gastritis, and duodenitis, intestinal ulcerations including inflammatory bowel disease, ulcerative colitis, Crohn's disease and proctitis, and gastrointestinal ulcerations, as well as neurogenetic inflammation such as cough and asthma, and depression. It is also believed that the compounds of this invention are effective in the treatment of hyper-triglyceridaemia, hypercholesterolaemia and conditions of low and high densitylipoprotein levels, artherosclerotic disease and cardiovascular disease and related conditions. Additionally, it is also believed that the compounds of this invention are effective in the treatment of ocular hypertension and glaucoma, as platelet aggregation inhibitors, and in the treatment of urinary disorders including pollakiuria and incontinence, as well as in the treatment of prostate disease and as topical anti-inflammatory agents.

Therefore, the compounds of this invention are expected to be valuable as therapeutic agents. An embodiment of this invention includes a method of treating beta-3 adrenergic receptor mediated conditions in a mammal which comprises administering to said mammal a composition containing an amount of the compound of Formula I that is effective in treating the target condition.

The specificity of the compounds of this invention as beta-3 adrenergic receptor agonists can readily be determined by evaluating the affinity of the compound for the different beta adrenergic receptor subtypes and comparing the activity with various receptor subtypes affinities to discover specificity as well as activity. This can be determined by standard and well-known procedures. For example, the utility of the present invention as beta-3 adrenergic receptor agonists useful in treating beta-3 adrenergic receptor mediated conditions can be demonstrated by the following procedure.

Chinese hamster ovary (CHO) cells that stably express full-length human beta-3-adrenergic receptor (Emorine, L. J. et al: *Molecular Characterization of the Human Beta-3-Adrenergic Receptor.* Science (Wash. D.C.) 245: 1118–1121,1989) were used in the following procedure. All cell lines were grown in 90% F12 nutrient mixture (HAM), 10% fetal bovine serum, 100 units/ml penicillin G sodium 100 mg/ml streptomycin sulfate and 2 mM L-glutamine at 37° C. in 95% air and 5% CO2. The transfected cell lines are exposed to G-418 (800 ug/ml) every $4^{th}$ passage or so.

To test the agonist activity, cells are exposed to test compound and then assayed for cAMP production. 100 ul CHO cells are plated at $5\times10^4$ cells/well of a 96 well plate (#3596, Costar, Cambridge, Mass.) to achieve 70% confluency the next day. After overnight incubation at 37° C., media is removed and the cells are treated for 30 minutes at 37° C. with KRP buffer(120 mM NaCl, 5.1 mM KCl, 0.6 mM $MgSO_4.7H_2O$, 0.8 mM $CaCl_2.H_2O$, 12.5 uM Phosphate buffer, 20 uM Hepes pH 7.4)+0.2 uM IBMX (100 ul/well), +1% DMSO, +/− test compounds (10 uM DMSO stocks). Test compounds are assayed from 10 uM to 3 nM with 3 fold serial dilutions. The control compound, isoproterenol (10 mM stock in 1.1 mM ascorbate), is a general agonist of all three adrenergic receptors and is assayed by 3 fold dilution beginning at 1 uM. All test compound activities are expressed as % of the maximal response of 1 uM isoproterenol. The expected $EC_{50}$ values of isoproterenol for the beta-3, beta-2, and beta-1 receptors are 5 nM, 1 nM and 0.2 nM, respectively.

After the 30 minute incubation with the test compounds, the buffer/compound mixture is removed and the cells are treated with 200 ul per well 65% ethanol for 10 minutes at room temperature. 150 ul per well of this lysate is then transferred to a Scintillation Proximity Assay plate (#6005162, Packard, Meriden, Conn.) and the plate is dried at 37° C. for 1.5 hours.

The cAMP SPA screening assay system (#RPA 556, Amersham, Arlington Heights, Ill.) is used to measure the amount of cAMP produced.

In tests utilizing the above described procedures, the test compounds of the present invention were found to have beta-3 adrenergic agonist activity.

Based upon the above and other standard laboratory techniques known to evaluate compound receptor site inhibition, by standard toxicity tests and by standard pharmacological assays for the determination of treatment of the beta-3 receptor mediated conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.01 mg/kg to about 100 mg/kg, and preferably from about 0.1 mg/kg to about 20 mg/kg body weight per day. A unit dosage may contain from about 5 mg to about 1500 mg of active ingredient, and can be administered one or more times per day. Of course the specific initial and continuing dosage regimen for each patient will vary according to the nature and severity of the condition as determined by the attending diagnostician.

The compounds of this invention can be utilized to achieve the desired pharmacological effect by administration to a patient in need thereof in an appropriately formulated pharmaceutical composition. A patient, for the purpose of this invention, is a mammal, including a human, in need of treatment for a particular beta-3 adrenergic receptor mediated condition or disease. Therefore, the present invention includes pharmaceutical compositions which are comprised of a pharmaceutically acceptable carrier and a pharmaceutically effective amount of a compound of Formula I, or a pharmaceutically acceptable salt or ester thereof. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is that amount which produces a result or exerts an influence on the particular condition being treated. The compounds of Formula I can be administered with a pharmaceutically-acceptable carrier using any effective conventional dosage unit forms, including immediate and timed release preparations, orally, parenterally, topically, or the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule which can be of the ordinary hard or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, cornstarch or gelatin, disintegrating agents intended to assist the break-up and dissolution of the tablet following administration such as potato starch, alginic acid, corn starch, and guar gum, lubricants intended to improve the flow of tablet granulation and to prevent the adhesion of tablet material to the surfaces of the tablet dies and punches, for example talc, stearic acid, or magnesium, calcium or zinc stearate, dyes coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent or emulsifying agent.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such a sucrose or saccharin.

Syrups and elixirs may be formulated with sweetening agents such as, for example, glycerol, propylene glycol, sorbitol or sucrose. Such formulations may also contain a demulcent, and preservative and flavoring and coloring agents.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acide include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (See, e.g., U.S. Pat. No. 5,023,252, issued Jun. 11, 1991, incorporated herein by reference). Such patches may be constructed for continuous, pulsatile, or on demand delivery of pharmaceutical agents.

It may be desirable or necessary to introduce the pharmaceutical composition to the patient via a mechanical delivery device. The construction and use of mechanical delivery devices for the delivery of pharmaceutical agents is well known in the art. Direct techniques, for example, for administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

The compound of this invention can be administered as the sole pharmaceutical agent or in combination with one or more other pharmaceutical agents where the combination causes no unacceptable adverse effects. For example, the compounds of this invention can be combined with known anti-obesity or other indication agents, and the like, as well as with admixtures and combinations thereof.

The compounds of Formula 1 may also be utilized, in free base form or in compositions, in research and diagnostics, or as analytical references standards, and the like. Therefore, the present invention includes compositions which are comprised of an inert carrier and an effective amount of a compound of Formula I, or a salt or ester thereof. An inert carrier is any material which does not interact with the compound to be carried and which lends support, means of conveyance, bulk, traceable material, and the like to the compound to be carried. An effective amount of compound is that amount which produces a result or exerts an influence on the particular procedure being performed.

The following specific examples are presented to illustrate the invention described herein, but they should not be construed as limiting the scope of the invention in any way.

Unless otherwise noted, reagents and solvents were obtained from commercial suppliers and were used without further purification.

Melting points were recorded in open capillary tubes and are uncorrected.

¹H NMR spectra were determined at 300 MHz using a General Electric GE-OMEGA 300 spectrometer. Chemical shifts are reported in parts per million (δ) values relative to tetramethylsilane as internal standard. Spin multiplicities are reported using the following abbreviations: singlet (s), doublet (d), triplet (t), quartet (q), multiplet (m), and broad (br). Coupling constants are in Hertz (Hz).

Fast atom bombardment (FAB) mass spectra were recorded using a Kratos Concept 1 spectrometer; electron impact (EI) and chemical ionization (CI) mass spectra were recorded using a Hewlett-Packard MS Engine (HP5989A) spectrometer; liquid chromatography-mass spectra (LC-MS) were recorded using a Finningan MAT LCQ spectrometer.

TLC was performed on silica gel plates using the following solvent systems: (A) 48:48:5 hexane/ethyl acetate/methanol; (B) 45:45:10 hexane/ethyl acetate/methanol; (C) 50:50 hexane/ethyl acetate; (D) 90:10 ethyl acetate/methanol; (E) 49:49:2 hexane/ethyl acetate/methanol; (F) 30:70 methanol/ethyl acetate; (G) 40:60 methanol/ethyl acetate; (H) 20:80 methanol/methylene chloride, (I) 65:35 hexane/ethyl acetate; (J) 90:10 dichloromethane/methanol; (K) 80:20 ethyl acetate/methanol; (L) ethyl acetate; (M) 80:20 hexane/ethyl acetate; (N) 75:25 hexane/ethyl acetate; and (O) 40:40:20 hexane/ethyl acetate/methanol.

EXAMPLE 1

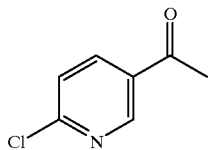

5-Acetyl-2-chloropyridine

Triethylamine (19 mL, 0.14 mol) and dimethyl malonate (7.8 mL, 59 mmol) were added to a round bottom flask containing magnesium chloride (3.8 g, 40 mmol) in anhydrous toluene (46 mL). The mixture was stirred at 25° C. for 1 h. A solution of 6-chloronicotinyl chloride (10 g, 57 mmol) in anhydrous toluene (50 mL) was slowly added to the mixture. The reaction was stirred for 1 h, then concentrated HCl (16 mL) was slowly added to the reaction. Diethyl ether (300 mL) was added and the organic layer was washed with water (2×100 mL). The organic layer was dried (MgSO₄), filtered, and concentrated to afford an oil. The product was stirred in hexanes (200 mL), eventually forming an off-white powder (12.7 g). The powder was treated with dimethyl sulfoxide (31 mL) and water (1 mL). The reaction was stirred and heated to 165° C. for 2 h. The reaction was cooled to room temperature, diluted with diethyl ether (250 mL), and washed with water (4×200 mL). The organic layer was dried (MgSO₄), filtered, and concentrated to afford a white solid. The product was passed through a pad of silica (5% diethyl ether/hexane) to yield a white solid (6.0 g, 68%). Rf=0.2 (CH₂Cl₂); mp 100–102° C.; ¹H NMR (300 MHz, CDCl₃) δ 8.94 (s, 1 H), 8.20 (dd, J=6, 9 Hz, 1 H), 7.44 (d, J=8 Hz, 1 H), 2.63 (s, 3 H); MS (EI) m/z 155 (M⁺).

EXAMPLE 2

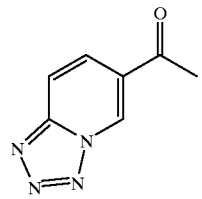

6-Acetyl tetrazolo[1,5-a] pyridine

A solution of 5-acetyl-2-chloropyridine (500 mg, 3.2 mmol) in ethanol (8 mL) and water (3 mL) was carefully treated with sodium azide (0.42 g, 6.4 mmol). Concentrated HCl (0.4 mL) was added dropwise at room temperature. The reaction was refluxed for 16 h and then cooled to room temperature. Saturated NaHCO₃ was added dropwise until pH=7. Dichloromethane (100 mL) was added and the reaction was washed with water (2×100 mL). The organic layer was dried (MgSO₄), filtered, and concentrated to afford a white solid (390 mg, 75%). Rf=0.1 (CH₂Cl₂); mp 156–158° C.; ¹H NMR (300 MHz, CDCl₃) δ 9.44 (s, 1 H), 8.23 (dd, J 8, 10 Hz, 1 H), 8.09 (dd, J=9, 10 Hz, 1 H), 2.75 (s, 3 H); MS (EI) m/z 162 (M⁺).

EXAMPLE 3

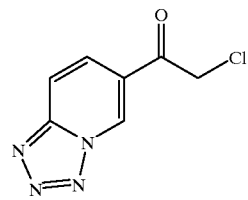

6-Bromoacetyltetrazolo[1,5-a] pyridine

6-Acetyl tetrazolo[1,5-a] pyridine (10 g, 62 mmol) in acetic acid (160 mL) was treated with 30% HBr/acetic acid (14.7 mL, 247 mmol) at 0° C. N-bromosuccinimide (11 g, 62 mmol) was slowly added and the reaction stirred for 30 minutes. Another 4 equivalents of 30% HBr/acetic acid (14.7 mL, 247 mmol) was slowly added and the reaction was allowed to warm to room temperature. After 3 hours, the reaction was diluted with ethyl acetate (500 mL) and washed with water (3×300 mL). The organic layer was dried (MgSO₄), filtered, and concentrated to afford an oil. Hexanes (75 mL) and dichloromethane (10 mL) were added to the oil and reconcentrated to afford a yellow solid (12.8 9, 86%). Rf=0.2 (CH₂Cl₂); mp 108–110° C.; ¹H NMR (300 MHz, CDCl₃) δ 10.2 (s, 1 H), 8.29 (dd, J=9, 10 Hz, 1 H), 8.18 (dd, J=8, 10 Hz, 1 H), 5.06 (s, 2 H); MS (EI) m/z 241 (M⁺).

EXAMPLE 4

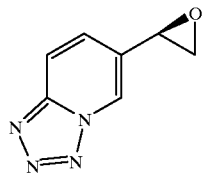

(R)-2-(tetrazolo[1,5-a]pyrid-6-yl)oxirane

To a solution of 6-Bromoacetyltetrazolo[1,5-a] pyridine (55 g, 0.23 mol) in ethanol (400 mL) was slowly treated with sodium borohydride (17 g, 0.46 mol) at 0° C. The reaction was allowed to warm to room temperature for 1 h. Ethyl acetate (400 mL) and 1N NaOH (400 mL) was added to the reaction. The organic layer was separated, washed with water, dried (MgSO$_4$), filtered and concentrated to leave an oily residue. Flash chromatography (10% CH$_3$CN/hexane) yielded an off-white solid (17 g, 46%). The racemate was separated using a Diacel Chiralpak AS column (100% MeOH, 1.0 mL/min.) yielding the title compound (7 g) in 99% ee. R$_f$=0.16 (CH$_2$Cl$_2$); mp 106–8° C.; $^1$H NMR (300 MHz, CDCl$_3$) δ 9.38 (s, 1 H), 8.17 (d, J=9, Hz, 1 H), 8.17 (dd, J=8, 10 Hz, 1 H), 4.16 (m, 1 H), 3.22 (m, 1 H), 3.09 (m, 1 H); MS (EI) m/z 162 (M$^+$); [α]$^{22}$=+6.0.

EXAMPLE 5

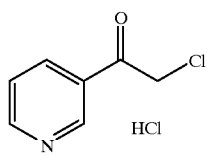

3-(2-Chloroacetyl)pyridine hydrochloride

To a solution of 100 g (0.83 moles) of 3-acetylpyridine in diethyl ether (1 L) was added of 1 M hydrogen chloride in ether (950 mL) with rapid stirring. The precipitated solids were filtered, washed with ether and dried. The hydrochloride salt (129 g, 0.83 moles) was added to a 5 L reactor equipped with a mechanical stirrer and dissolved with 1 M hydrogen chloride in acetic acid (830 mL). The mixture was stirred until a clear solution was obtained. N-chlorosuccinimide (111 g, 0.83 moles) was added, and a yellow mixture resulted. The solution was stirred at room temperature for 18 hours, gradually becoming a colorless suspension. The solids were collected by filtration and washed with ether. The filtrate was treated overnight with 80 g of N-chlorosuccinimide and additional product was collected to give a combined yield of 152 g. $^1$H NMR (DMSO-d$_6$) δ 10.3 (br s, 1 H), 9.27 (s, 1 H), 8.96 (d, J=5.1 Hz, 1 H), 8.62 (d, J=9.9 Hz, 1 H), 7.89 (m, 1 H), 5.30 (s, 2 H); MS (EI) m/z 155 (M$^+$).

EXAMPLE 6

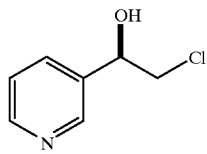

(R)-Chloromethyl-3-pyridinemethanol

A stirred, cold (–10° C.) suspension of 3-(2-chloroacetyl) pyridine hydrochloride (250 g) in methanol (1.5 L) was carefully treated with sodium borohydride (74 g) over a period of 1 hour. The resulting yellow suspension was stirred for an additional 40 minutes and was quenched by the addition of water (500 mL). The mixture was then concentrated in vacuo to remove methanol, diluted with water and neutralized with acetic acid. The biphasic mixture was extracted with ethyl acetate (Na$_2$SO$_4$), filtered and concentrated in vacuo. The crude racemic mixture was purified by silica gel chromatography (ethyl acetate/hexane) to give 146.5 g of a yellow oil which was then resolved by chiral chromatography to afford the pure enantiomer as a dark orange oil, 75 g (containing residual solvent). $^1$H NMR (CDCl$_3$) δ 8.58 (s, 1 H), 8.53 (d, J=4.8 Hz, 1 H), 7.78 (d, J=7.9 Hz, 1 H), 7.32 (m, 1 H), 4.96 (m, 1 H), 3.71 (m, 1 H); MS (EI) m/z 158 (MH$^+$).

EXAMPLE 7

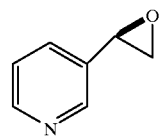

(R)-(Pyrid-3-yl)oxirane

To a solution of (R)-chloromethyl-3-pyridinemethanol (74 g, 0.47 mole) in acetone (2 L) was added potassium carbonate (300 g). The stirred mixture was heated to reflux for 18 hours and then cooled to room temperature. The dark red suspension was filtered and the filtrate was concentrated to dryness in vacuo. Flash chromatography (silica gel, 0–5% methanol/dichloromethane) afforded the epoxide (26 g, 46%) as an orange oil. $^1$H NMR (CDCl$_3$) δ 8.56 (m, 2 H), 7.53 (d, 1 H, J=7.7 Hz), 7.28 (m, 1 H), 3.88 (m, 1 H), 3.18 (t, J=4.8 Hz, 1 H), 2.81 (m, 1 H); MS (EI) m/z 121 (M$^+$).

EXAMPLE 8

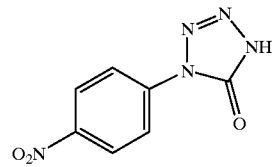

1-(4-Nitrophenyl)-5-tetrazolone

A solution of 1-phenyl-5-tetrazolone (30 g) in acetonitrile (300 mL) was stirred under argon at 0° C. and nitronium tetrafluoroborate (36.9 g) was added over 30 minutes. After stirring at 0° C. for an additional 30 minutes the mixture was poured into water (900 mL). The precipitate was collected by filtration and dried under vacuum to give 23.1 g of the title compound as cream-colored solids. The filtrate was extracted with ethyl acetate, dried (MgSO$_4$), filtered, and concentrated to give an additional 8.6 g of solids which was a 1:1 mixture of ortho- and para-substituted isomers. $^1$H NMR (acetone-d$_6$) δ 13.62 (br s, 1 H), 8.36 (ABq, J$_{AB}$=9.2 Hz, 4 H); MS (EI) m/z 207 (M$^+$); Rf=0.2 (10% methanol/dichloromethane).

EXAMPLE 9

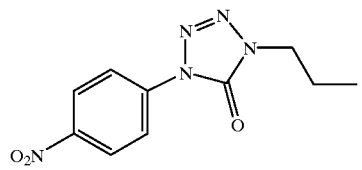

1-(4-Nitrophenyl)-4-propyl-5-tetrazolone

To a stirred solution of 1-(4-nitrophenyl)-5-tetrazolone (6 g) in anhydrous N,N-dimethylformamide (30 mL) was added powdered 85% potassium hydroxide (1.9 g) and 1-bromopropane (3.9 g). The mixture was stirred at 55° C. for 2 hours and then poured into 300 mL of water. The biphasic mixture was extracted with ethyl acetate, dried (MgSO$_4$), filtered and concentrated in vacuo. The crude product was purified by flash chromatography (silica gel, ethyl acetate:hexane) to afford 7.2 g of the title compound as a pale yellow solid. $^1$H NMR (CDCl$_3$) δ 8.32 (ABq, J$_{AB}$=9.6 Hz, 4 H), 4.02 (t, J=7.2 Hz, 2 H), 1.93 (m, 2 H), 1.03 (t, J=7.5 Hz, 3 H); MS (CI) m/z 250 (MH$^+$); R$_f$=0.6 (25% ethyl acetate/hexane).

Examples 10 to 13 can be made according to the procedures described in Example 8 and Example 9 with the appropriate alkyl halide.

EXAMPLE 10

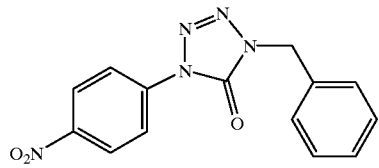

1-(4-Nitrophenyl)-4-benzyl-5-tetrazolone MS (CI) m/z 298 (MH$^+$); R$_f$=0.8 (25% ethyl acetate/hexane).

EXAMPLE 11

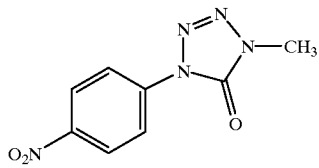

1-(4-Nitrophenyl)-4-methyl-5-tetrazolone MS (CI) m/z 222 (MH$^+$); R$_f$=0.3 (25% ethyl acetate/hexane).

EXAMPLE 12

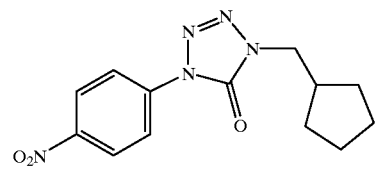

1-(4-Nitrophenyl)-4-cyclopentylmethyl-5-tetrazolone MS (CI) m/z 290 (MH$^+$); R$_f$=0.7 (25% ethyl acetate/hexane).

EXAMPLE 13

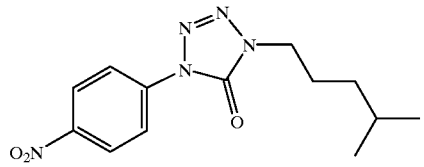

1-(4-Nitrophenyl)-4-(4-methylpentyl)-5-tetrazolone MS (EI) m/z 291 (M$^+$); R$_f$=0.7 (25% ethyl acetate/hexane).

EXAMPLE 14

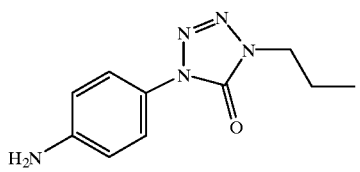

1-(4-Aminophenyl)-4-propyl-5-tetrazolone

A solution containing 1-(4-nitrophenyl)-4-propyl-5-tetrazolone (6.1 g) and 10% palladium on carbon (2.5 g) in ethanol (250 mL) was stirred under 1 atmosphere of hydrogen for 18 hours. The suspension was filtered through a pad of diatomaceous earth, and the filtrate was concentrated in vacuo. Purification by flash chromatography (silica gel, dichloromethane) gave the pure product as 5.22 g of colorless crystals. $^1$H NMR (CDCl$_3$) δ 7.62 (d, J=8.8 Hz, 2 H), 6.75 (d, J=8.8 Hz, 2 H), 3.97 (t, J=7.2 Hz, 2 H), 3.82 (br s, 2 H), 1.91 (m, 2 H), 1.01 (t, J=7.5 Hz, 3 H); MS (EI) m/z 219 (M$^+$); R$_f$=0.1 (25% ethyl acetate/hexane).

Examples 15 to 18 can be made according to the procedure described in Example 14 using Examples 10 to 13 as starting material.

EXAMPLE 15

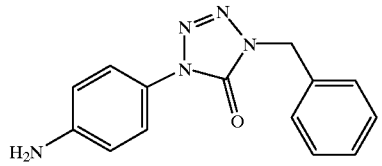

1-(4-aminophenyl)-4-benzyl-5-tetrazolone MS (EI) m/z 267 (M$^+$); R$_f$=0.1 (25% ethyl acetate/hexane).

EXAMPLE 16

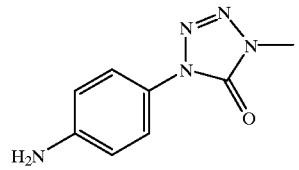

1-(4-Aminophenyl)-4-methyl-5-tetrazolone MS (EI) m/z 191 (M$^+$); R$_f$=0.4 (1:1 ethyl acetate/hexane).

EXAMPLE 17

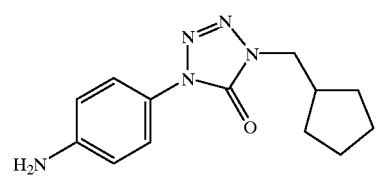

1-(4-Aminophenyl)-4-cyclopentylmethyl-5-tetrazolone MS (EI) m/z 259 (M$^+$); R$_f$=0.2 (1:3 ethyl acetate/hexane).

EXAMPLE 18

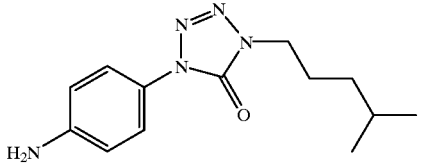

1-(4-Aminophenyl)-4-(4-methylpentyl)-5-tetrazolone MS (CI) m/z 262 (MH+); $R_f$=0.3 (25% ethyl acetate/hexane).

EXAMPLE 19

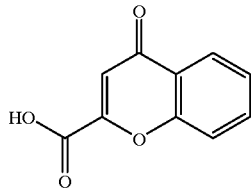

4-Oxo-4H-chromene-2-carboxylic acid

A mixture of diethyl oxalate (110 mL, 810 mmol) and 2'-hydroxyacetophenone (44 mL, 365 mmol) was added over 20 minutes to a solution of sodium ethoxide (76 g, 1.11 mol) in ethanol (600 mL). The mixture was heated to 80° C. for one hour then cooled to room temperature. Water (500 mL) and diethyl ether (600 mL) were added, and the mixture acidified to pH=2 with concentrated hydrochloric acid. The organic phase was separated and the aqueous phase further extracted with diethyl ether (2×). The combined organic phase was washed with saturated aqueous sodium chloride solution (2×), dried (MgSO$_4$), and concentrated to give an oily brown solid.

The solid was mixed with glacial acetic acid (440 mL) and concentrated HCl (110 mL) and heated to 85° C. overnight. The mixture was cooled to room temperature, diluted with water (550 mL), and filtered. The solids were washed with water (2×125 mL) and dried in a vacuum oven to give a purple solid (58 g, 83%). Mp 260–261° C.; $^1$H NMR (DMSO-d$_6$, 300 MHz) δ 8.03 (m, 1 H), 7.85 (m, 1 H), 7.71 (m, 1 H), 7.51 (m, 1 H), 6.89 (s, 1 H).

EXAMPLE 20

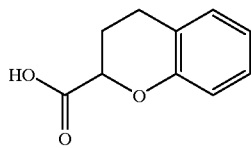

(±)-Chroman-2-carboxylic acid

A mixture of the compound from Example 19 (20.0 g, 105 mmol), and palladium on activated carbon (Pd 10%, 2.0 g) in acetic acid (200 mL) was placed under hydrogen pressure (60 psig) in a Parr hydrogenation apparatus. After 22.5 hours the mixture was removed from the hydrogen atmosphere and filtered through a pad of Celite. The Celite pad was washed with ethyl acetate (800 mL), and the combined filtrate concentrated to give a brown oil. The oil was dissolved in ethyl acetate (500 mL) and extracted with saturated aqueous NaHCO$_3$ solution (4×125 mL). The aqueous phase was acidified to pH=2 with concentrated HCl and extracted with ethyl acetate (4×100 mL). The combined organic phase was washed with saturated aqueous sodium chloride solution (100 mL), dried (MgSO$_4$), and concentrated to give a colorless solid (18.0 g, 96%). Mp 97.5–99° C.; $^1$H NMR (DMSO-d$_6$, 300 MHz) δ 12.96 (br s, 1 H), 7.03 (m, 2 H), 6.78 (m, 2 H), 4.74 (dd, J=6.4 Hz, 3.9 Hz, 1 H), 2.73 (m, 1 H), 2.63 (m, 1 H), 2.03 (m, 2 H).

EXAMPLE 21

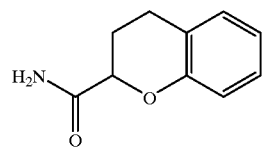

(±)-Chroman-2-carboxylic acid amide

Oxalyl chloride (11.0 mL, 126 mmol) was added dropwise to a cooled (0° C.) solution of the compound from Example 20 (15 g, 84.3 mmol) and N,N-dimethylformamide (1 mL) in tetrahydrofuran (250 mL). Upon completion of gas evolution the mixture was warmed to room temperature and concentrated in vacuo. The residue was dissolved in tetrahydrofuran (450 mL). The solution was cooled to −78° C. and ammonia condensed onto the mixture. After 30 minutes the mixture was warmed to room temperature, diluted with water, and extracted with ethyl acetate (2×). The combined organic phase was washed with saturated aqueous sodium chloride solution (2×), dried (MgSO$_4$), and concentrated to give a solid. The solid was triturated with 1:1 diethyl ether/hexanes and dried at 50° C. in vacuo to give a colorless solid (14.5 g, 97%). Mp 125–127° C.; $^1$H NMR (acetone-d$_6$, 300 MHz) δ 7.08 (m, 3 H), 6.86 (m, 2 H), 6.75 (br s, 1 H), 4.47 (dd, 9.2 Hz, 2.9 Hz, 1 H), 2.76 (m, 2 H), 2.28 (m, 1 H), 0.96 (m, 1 H).

EXAMPLE 22

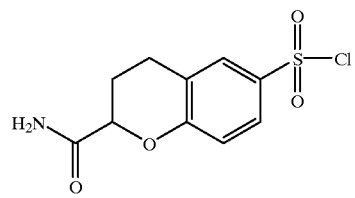

(±)-2-Carbamoylchroman-6-sulfonyl chloride

The compound from Example 21 (2.0 g, 11.3 mmol) was added in portions over 10 minutes to cooled (0° C.) chlorosulfonic acid (9 mL). After 75 minutes the mixture was added slowly and dropwise to ice (150 g). The mixture was filtered and the solids washed with water (3×20 mL) and dried at 50° C. in vacuo to give a colorless powder (2.29 g, 73%). Mp 147–148° C.; $^1$H NMR (CDCl$_3$, 300 MHz) δ 7.82 (m, 2 H), 7.08 (d, J=8.6 Hz, 1 H), 6.50 (br s, 1 H), 5.77 (br s, 1 H), 4.68 (dd, J=9.4 Hz, 3.1 Hz, 1 H), 2.95 (m, 2 H), 2.52 (m, 1 H), 2.16 (m, 1 H).

EXAMPLE 23

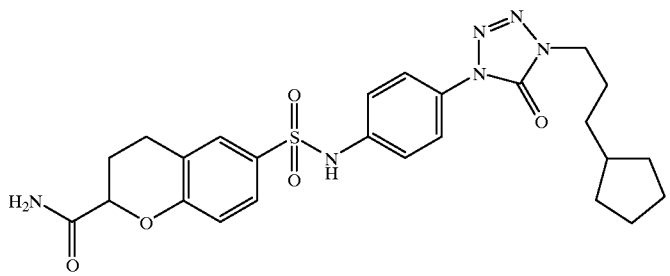

(±)-6-{4-[4-(3-Cyclopentylpropyl)-5-oxo-4,5-dihydrotetrazol-1-yl]phenylsulfamoyl}chroman-2-carboxylic acid amide Pyridine (650 mL, 8.03 mmol) followed by a solution of 1-(4-aminophenyl)-4-(3-cyclopentylpropyl)-5-tetrazolone (2.1 g, 7.32 mmol; prepared as described in WO 97/16189) in tetrahydrofuran (50 mL) were added to a cooled (0° C.) solution of the compound from Example 22 (2.02 g, 7.33 mmol) in tetrahydrofuran (50 mL). The mixture was heated to 50° C. overnight. Pyridine (650 mL) was added and the mixture re-heated to 50° C. After 72 hours the mixture was partitioned between ethyl acetate and water. The organic layer was washed with 5% aqueous hydrochloric acid (2×), saturated aqueous sodium bicarbonate, and saturated aqueous sodium chloride, dried (MgSO$_4$), and concentrated to a solid (3.7 g). The crude was recrystallized from ethyl acetate (260 mL). The recrystallization mixture was cooled to 0° C. before filtering to give colorless crystals (2.14 g). A second crop afforded 1.09 g. The combined yield was 3.22 g (83%). Mp 202–205° C.; H NMR (DMSO-d$_6$, 300 MHz) δ 10.43 (s, 1 H), 7.69 (d, J=8.8 Hz, 2 H), 7.53 (m, 3 H), 7.37 (br s, 1 H), 7.26 (d, J=8.8 Hz, 2 H), 6.95 (d, J=8.5 Hz, 1 H), 4.57 (dd, J=8.5 Hz, 3.3 Hz, 1 H), 3.92 (t, J=7.0 Hz, 2 H), 2.71 (m, 2 H), 2.13 (m, 1 H), 1.89 (m, 1 H), 1.72 (m, 5 H), 1.49 (m, 4 H), 1.30 (m, 2 H), 1.03 (m, 2 H); MS (FAB) m/z 527 (MH$^+$).

Examples 24 and 25 were prepared in analogy to the procedure of Example 23.

(±)-2-Aminomethylchroman-6-sulfonic acid {4-[4-(3-cyclopentylpropyl)-5-oxo-4,5-dihydrotetrazol-1-yl]phenyl}amide Borane-methyl sulfide complex (2.0 M solution in tetrahydrofuran, 17.1 mL, 34.2 mmol) was added to a cooled (0° C.) solution of the compound from Example 23 (3.0 g, 5.70 mmol) in tetrahydrofuran (75 mL). The mixture was heated to reflux for 90 minutes then cooled to 0° C. Methanol was added until gas evolution ceased, then 6N HCl (15 mL) was added. The mixture was heated to reflux for 60 minutes then cooled to 0° C. The mixture was brought to pH=12 with 10% aqueous sodium hydroxide and extracted with ethyl acetate (2×). the combined organic layers were dried (Na$_2$SO$_4$) and concentrated to a solid. Silica gel chromatography (gradient elution from 50:50 hexane/ethyl acetate to 45:45:10 hexane/ethyl acetate/methanol to 90:10 ethyl acetate/methanol) afforded a colorless solid (2.32 g, 80%). Mp 125–130° C. (dec); $^1$H NMR (DMSO- d$_6$, 300 MHz) δ 7.64 (d, J=8.8 Hz, 2 H), 7.54 (d, J=2.2 Hz, 1 H), 7.47 (dd, J=8.5 Hz, 2.2 Hz, 1 H), 7.22 (d, J=8.8 Hz, 2 H), 6.84 (d, J=8.8 Hz, 1 H), 5.6 (br s, 3 H), 4.04 (m, 1 H), 3.92 (t, J=7.0 Hz, 2 H), 2.83 (d, J=5.5 Hz, 2 H), 2.76 (m, 2 H), 2.0 (m, 1 H), 1.8–1.4 (m, 10 H), 1.30 (m, 2 H), 1.03 (m, 2 H); MS (FAB) m/z 513 (MH$^+$).

Examples 27 and 28 were prepared in analogy to the procedure of Example 26.

| Example | Name | MS | R$_f$ |
|---|---|---|---|
| 24 | (±)-6-(4-Isopropyl-phenylsulfamoyl)-chroman-2-carboxylic acid amide | 375 (MH$^+$) | 0.2 (E) |
| 25 | (±)-6-(4-Chloro-phenylsulfamoyl)-chroman-carboxylic acid amide | | 0.3 (C) |

| Example | Name | MS | R$_f$ |
|---|---|---|---|
| 27 | (±)-2-Aminomethyl-chroman-6-sulfonic acid (4-isopropyl-phenyl)-amide | 360 (MH$^+$) | 0.1 (B) |
| 28 | (±)-2-Aminomethyl-chroman-6-sulfonic acid (4-chloro-phenyl)-amide | 353 (MH$^+$) (Cl) | 0.1 (B) |

EXAMPLE 26

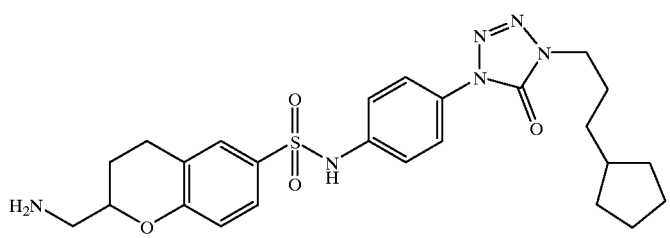

EXAMPLE 29

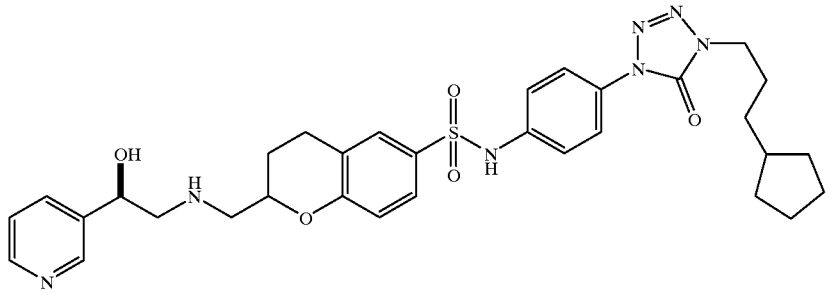

2-[(2R)-(2-Hydroxy-2-pyridin-3-ylethylamino)methyl]chroman-6-sulfonic acid {4-[4-(3-cyclopentylpropyl)-5-oxo-4,5-dihydrotetrazol-1-yl]phenyl}amide dihydrate A solution of the compound from Example 26 (563 mg, 1.1 mmol) and the compound from Example 7 (121 mg, 1.0 mmol) in 90:10 ethanol/water (20 mL) was heated to reflux for 7 hours. The mixture was concentrated in vacuo to a solid. The crude product was chromatographed on silica gel followed by alumina (methanol/dichloromethane eluent). The product was diluted with ethyl acetate, washed with saturated aqueous sodium chloride solution (3×), dried (MgSO$_4$), and concentrated to a solid. Silica gel chromatography (1:1 hexane/ethyl acetate and gradient elution of 5–15% methanol) afforded a colorless solid (68 mg, 11%). Mp 93–95° C.; $^1$H NMR (DMSO-d$_6$, 300 MHz) δ 8.54 (d, 2.2 Hz, 1 H), 8.43 (dd, J=4.8 Hz, 1.5 Hz, 1 H), 7.70 (m, 3 H), 7.54 (d, J=2.2 Hz, 1 H), 7.47 (dd, J=8.6 Hz, 2.4 Hz, 1 H), 7.32 (dd, J=7.7 Hz, 4.8 Hz, 1 H), 7.26 (d, J=9.2 Hz, 2 H), 6.85 (d, J=8.5 Hz, 1 H), 5.5 (m, 1 H), 4.7 (m, 1 H), 4.15 (m, 1 H), 3.92 (t, 7.0 Hz, 2 H), 2.75 (m, 6 H), 1.95 (m, 1 H), 1.8–1.65 (m, 6 H), 1.6–1.4 (m, 5 H), 1.30 (m, 2 H), 1.03 (m, 2 H); MS (FAB) m/z 634 (MH$^+$). Anal. calcd for C$_{32}$H$_{39}$N7O$_5$S.2 H$_2$O: C, 57.54; H, 6.46; N, 14.68. Found: C, 57.52; H, 6.15; N, 14.53.

Examples 30 to 34 were prepared in analogy to the procedure of Example 29.

| Example | Name | MS | R$_f$ |
|---|---|---|---|
| 30 | 2-{[(2R)-2-(3-Chloro-phenyl)-2-hydroxy-ethylamino]-methyl}-chroman-6-sulfonic acid (4-isopropyl-phenyl)-amide | 515 (MH$^+$) | 0.3 (A) |
| 31 | 2-[((2R)-2-Hydroxy-2-phenyl-ethylamino)-methyl]-chroman-6-sulfonic acid (4-isopropylphenyl)-amide | 481 (MH$^+$) | 0.1 (A) |
| 32 | 2-{[(2R)-2-(3-Chloro-phenyl)-2-hydroxy-ethylamino]-methyl}-chroman-6-sulfonic acid {4-[4-(3-cyclopentyl-propyl)-5-oxo-4,5-dihydrotetrazol-1-yl]-phenyl}-amide | 667 (MH$^+$) | 0.1 (B) |
| 33 | 2-{[(2R)-2-(3-Chloro-phenyl)-2-hydroxy-ethylamino]-methyl}-chroman-6-sulfonic acid (4-chloro-phenyl)-amide | 507 (MH$^+$) | 0.1 (C) |
| 34 | 2-[((2R)-2-Hydroxy-2-pyridin-3-yl-ethylamino)-methyl]-chroman-6-sulfonic acid (4-chlorophenyl)-amide | 474 (MH$^+$) | 0.3 (D) |

EXAMPLE 35

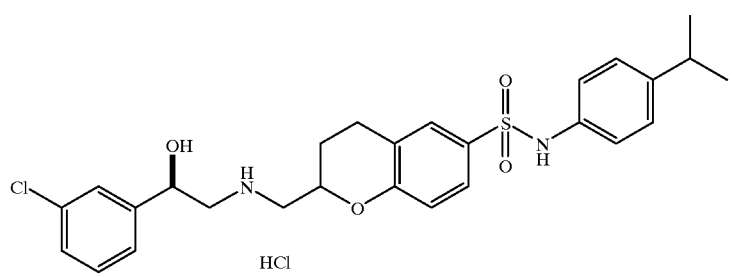

2-{[(2R)-2-(3-Chloro-phenyl)-2-hydroxy-ethylamino]-methyl}-chroman-6-sulfonic acid (4-isopropyl-phenyl)-amide hydrochloride A solution of hydrogen chloride in diethyl ether was added to a solution of the compound from Example 30 in ethyl acetate. The mixture was concentrated in vacuo to provide a solid.

EXAMPLE 36

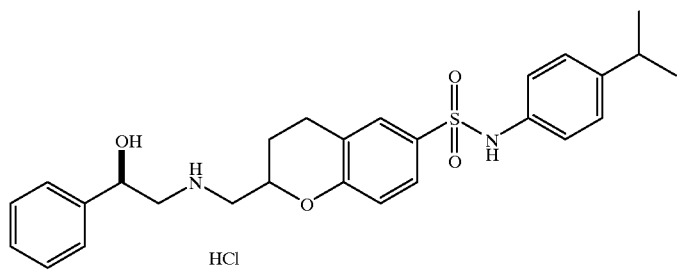

2-[((2R)-2-Hydroxy-2-phenyl-ethylamino)-methyl]-chroman-6-sulfonic acid (4-isopropyl-phenyl)-amide hydrochloride The title compound was prepared in analogy to the procedure of Example 35.

EXAMPLE 37

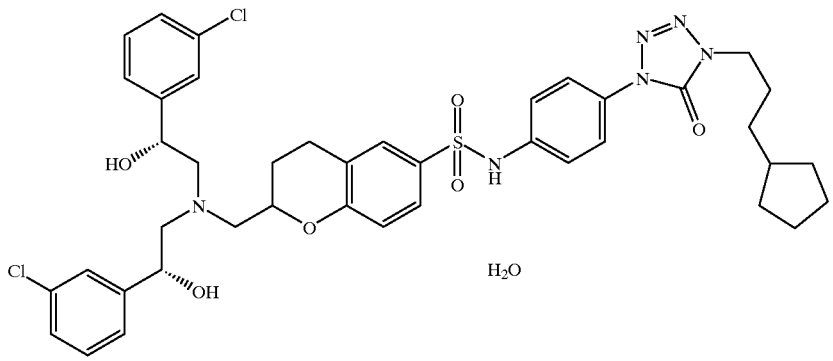

2-({Bis-[(2R)-2-(3-chloro-phenyl)-2-hydroxy-ethyl]-amino}-methyl)-chroman-6-sulfonic acid {4-[4-(3-cyclopentyl-propyl)-5-oxo-4,5-dihydro-tetrazol-1-yl]-phenyl}-amide hydrate From the same reaction mixture that produced the compound in Example 32, the title compound was obtained by silica gel chromatography as a solid (117 mg, 30%). Mp 110–115° C. (dec); MS (FAB) m/z 821 (MH$^+$); Anal. calcd for $C_{41}H_{46}Cl_2N_6O_6S \cdot H_2O$: C, 58.64; H. 5.76; N. 10.01. Found: C, 58.53; H. 5.73; N. 9.80. $R_f$=0.2 (B).

EXAMPLE 38

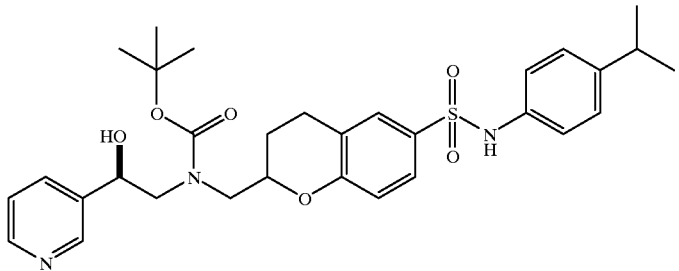

(2-Hydroxy-2-pyridin-3-yl-ethyl)-[6-(4-isopropyl-phenylsulfamoyl)-(2R)-chroman-2-ylmethyl]-carbamic acid tert-butyl ester Di-tert-butyl dicarbonate (210 mL, 0.91 mmol) was added to a solution of 2-[((2R)-2-hydroxy-2-pyridin-3-yl-ethylamino)-methyl]-chroman-6-sulfonic acid (4-isopropyl-phenyl)-amide (400 mg, 1.11 mmol, obtained as a crude solid from the intermediate in Example 27 according to the procedure in Example 29) in tetrahydrofuran (15 mL). After one hour the mixture was concentrated in vacuo. Silica gel chromatography (gradient elution with 50:50 hexane/ethyl acetate to 48:48:5 hexane/ethyl acetate/methanol) afforded a yellow oil (221 mg, 43%). $R_f$=0.4 (B).

Examples 39 and 40 were prepared in analogy to the procedure of Example 38.

| Example | Name | MS | $R_f$ |
|---|---|---|---|
| 39 | (6-{4-[4-(3-Cyclopentyl-propyl)-5-oxo-4,5-dihydro-tetrazol-1-yl]-phenylsulfamoyl}-chroman-2-ylmethyl)-((2R*)-2-hydroxy-2-tetrazolo[1,5-a]pyridin-6-yl-ethyl)-carbamic acid tert-butyl ester | 775 (MH$^+$) | 0.3 (C) |
| 40 | [6-(4-chloro-phenylsulfamoyl)-chroman-2-ylmethyl]-((2R*)-2-hydroxy-2-tetrazolo[1,5-a]pyridin-6-yl-ethyl)-carbamic acid tert-butyl ester | | 0.7 (B) |

EXAMPLE 41

2-[((2R)-2-Hydroxy-2-pyridin-3-yl-ethylamino)-methyl]-chroman-6-sulfonic acid (4-isopropyl-phenyl)-amide hydrate A solution of the intermediate from Example 38 (430 mg, 0.89 mmol) in 2N methanolic HCl (10 mL) was heated to reflux for two hours. The solution was concentrated in vacuo and the residue was partitioned between ethyl acetate and water. The aqueous phase was made basic with 10% aqueous sodium hydroxide and extracted with ethyl acetate. The organic phases were dried ($Na_2SO_4$) and concentrated in vacuo to afford a colorless crystalline solid (133 mg, 73%). $R_f$=0.1 (B); Mp 104–106° C.; MS (FAB) m/z 482 (MH$^+$); Anal. calcd for $C_{41}H_{46}Cl_2N_6O_6S \cdot 0.7\ H_2O$: C, 63.19; H, 6.61; N, 8.50. Found: C, 63.20; H, 6.51; N, 8.20.

Examples 42 and 43 were prepared in analogy to the procedure of Example 41.

| Example | Name | MS | $R_f$ |
|---|---|---|---|
| 42 | 2-[((2R*)-2-Hydroxy-2-tetrazolo[1,5-a]pyridin-6-yl-ethylamino)-methyl]-chroman-6-sulfonic acid (4-chloro-phenyl)-amide | 515 (MH$^+$) | 0.1 (B) |
| 43 | 2-[((2R*)-2-Hydroxy-2-tetrazolo[1,5-a]pyridin-6-yl-ethylamino)-methyl]-chroman-6-sulfonic acid {4-(4-(3-cyclopentyl-propyl)-5-oxo-4,5-dihydrotetrazol-1-yl]-phenyl}-amide | 675 (MH$^+$) | 0.2 (B) |

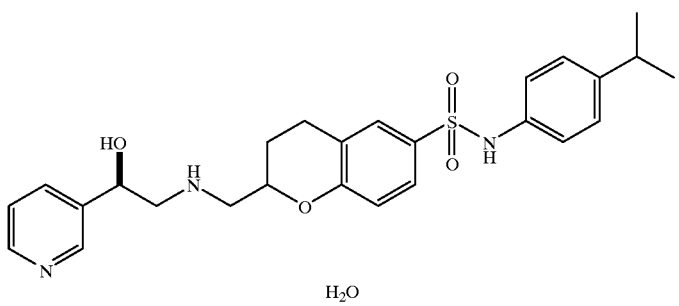

EXAMPLE 44

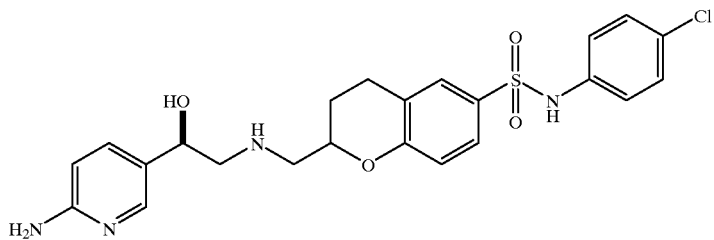

2-{[(2R*)-2-(6-Amino-pyridin-3-yl)-2-hydroxy-ethylamino]-methyl}-chroman-6-sulfonic acid (4-chlorophenyl)-amide A mixture of the compound from Example 42 (120 mg, 0.23 mmol), concentrated HCl (160 mL), and tin (II) chloride dihydrate (110 mg, 0.49 mmol) in methanol (5 mL) was heated to reflux for 18 hours. The mixture was concentrated and the residue was diluted with water and ethyl acetate. The aqueous phase was made basic with 1 N NaOH. The organic phase was removed and the aqueous phase extracted with ethyl acetate (3×). The combined organic phases were dried and concentrated to give a solid. Silica gel chromatography (gradient elution from 45:45:10 hexane/ethyl acetate/methanol to 90:10 ethyl acetate/methanol to 88:10:2 ethyl acetate/methanol/aqueous ammonium hydroxide) afforded a solid (86 mg, 77%). Mp 95° C. (dec); MS (FAB) m/z 489 (MH$^+$); R$_f$=0.2 (D); Anal. calcd for $C_{23}H_{25}ClN_4O_4S \cdot 0.42$ $H_2O$: C, 55.63; H, 5.25; N, 11.28; found: C, 55.94; H, 5.22; N, 10.88.

EXAMPLE 45

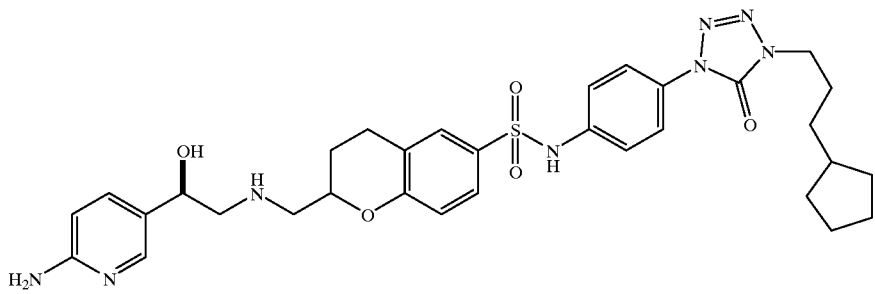

2-{[(2R*)-2-(6-Amino-pyridin-3-yl)-2-hydroxy-ethylamino]-methyl}-chroman-6-sulfonic acid {4-[4-(3-cyclopentyl-propyl)-5-oxo-4,5-dihydro-tetrazol-1-yl]-phenyl}-amide The title compound was prepared in analogy to the procedure of Example 44. MS (FAB) m/z 649 (MH$^+$); R$_f$=0.1 (B).

EXAMPLE 46

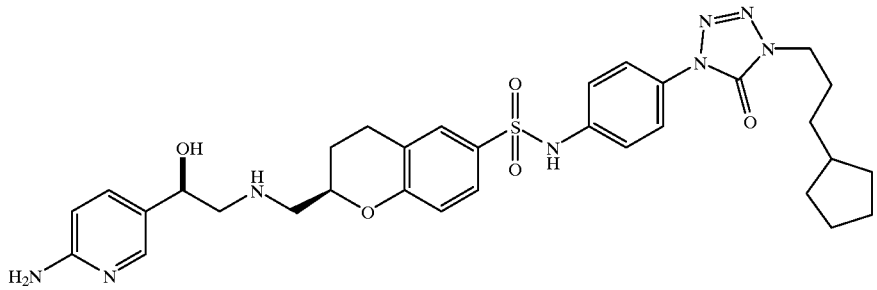

(2R)-2-[((2R)-2-Hydroxy-2-pyridin-3-yl-ethylamino)-methyl]-chroman-6-sulfonic acid {4-[4-(3-cyclopentyl-propyl)-5-oxo-4,5-dihydro-tetrazol-1-yl]-phenyl}-amide The title compound was prepared from (R)-chroman-2-carboxylic acid (prepared according to Ger. Offen. DE 4430089 A1 960229) by the procedures described in Examples 21–23, 27, and 29. $R_f$=0.1 (D).

EXAMPLE 47

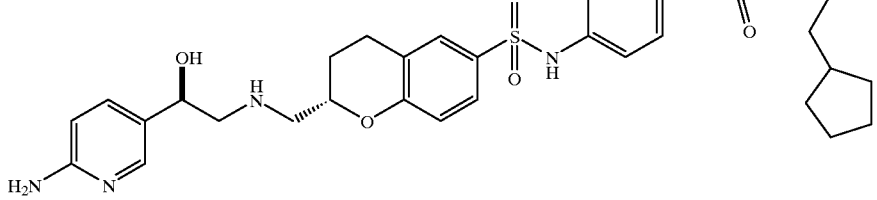

(2S)-2-[((2R)-2-Hydroxy-2-pyridin-3-yl-ethylamino)-methyl]-chroman-6-sulfonic acid {4-[4-(3-cyclopentyl-propyl)-5-oxo-4,5-dihydro-tetrazol-1-yl]-phenyl}-amide The title compound was prepared from (S)-chroman-2-carboxylic acid (prepared according to Ger. Offen. DE 4430089 A1 960229) by the procedures described in Examples 21–23, 27, and 29. $R_f$=0.1 (D).

EXAMPLE 48

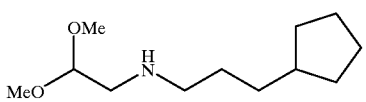

(3-Cyclopentyl-propyl)-(2,2-dimethoxy-ethyl)-amine

A mixture of 2-aminoacetaldehyde dimethyl acetal (3.0 mL, 27.5 mmol), solid potassium carbonate (2.1 g, 15.2 mmol), and 3-cyclopentyl-1-iodopropane (3.3 g, 13.9 mmol) in anhydrous N,N-dimethylformamide was stirred for 12 hours at room temperature. The mixture was filtered, and the filtrate was partitioned between water and ethyl acetate. The organic layer was washed with brine, dried ($Na_2SO_4$) and concentrated to a crude oil. The crude was passed through a plug of silica gel with ethyl acetate to provide a yellow oil (2.67 g, 89%). H NMR (300 MHz, DMSO-$d_6$) δ 4.35 (t, 1 H), 3.23 (s, 6 H), 2.54 (d, 2 H), 1.70 (m, 3 H), 1.51 (m, 6 H), 1.36 (m, 2 H), 1.27 (m, 2 H), 1.04 (m, 2 H).

EXAMPLE 49

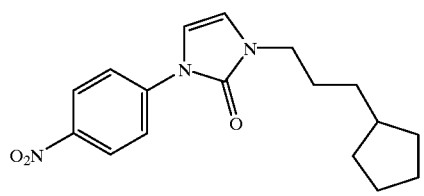

1-(3-Cyclopentyl-propyl)-3-(4-nitro-phenyl)-1,3-dihydro-imidazol-2-one

The product from Example 48 (2.6 g, 12.1 mmol) was dissolved in $CH_2Cl_2$ (30 mL) and cooled to 0° C. 4-Nitrophenylisocyanate (1.98 g, 12.1 mmol) was added, and the mixture was allowed to warm to 23° C. The reaction was diluted with additional $CH_2Cl_2$ (30 mL) and cooled to 0° C. before a 1:1 solution of trifluoroacetic acid and water was added. The biphasic solution was vigorously stirred for 18 hours at ambient temperature. The layers were separated, and the aqueous layer was extracted with $CHCl_3$. The combined organic layers were washed with saturated $NaHCO_3$, brine, dried ($MgSO_4$), and concentrated to a yellow solid. Mp 105–107° C. $R_f$=0.4 (2:1 hexanes/ethyl acetate); $^1$H NMR (300 MHz, DMSO-$d_6$) δ 8.30 (d, 2 H), 8.11 (d, 2 H), 7.26 (d, 1 H), 6.91 (d, 1 H), 3.57 (t, 2 H), 1.71 (m, 3 H), 1.63 (m, 2 H), 1.47 (m, 4 H), 1.24 (m, 2 H), 1.03 (m, 2 H); MS (CI) m/z 316 (MH$^+$).

EXAMPLE 50

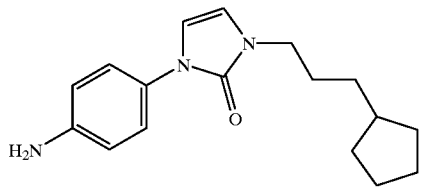

1-(4-Amino-phenyl)-3-(3-cyclopentyl-propyl)-imidazolidin-2-one

A mixture of the product from Example 49 (3.7 g, 11.7 mmol) and 10% palladium on activated carbon (0.74 g) in ethyl acetate (200 mL) was placed under an atmosphere of hydrogen overnight. The mixture was filtered through a pad of Celite with excess ethyl acetate, and the filtrate was concentrated to a crude brown oil. The crude was purified by silica gel chromatography (gradient elution from 2:1 hexanes/ethyl acetate to 1:1 hexanes/ethyl acetate) to afford a pale orange solid (2.01 g, 60%). Mp 97–99° C.; $R_f$=0.1 (2:1 hexanes/ethyl acetate); 1H NMR (300 MHz, DMSO-$d_6$) δ 7.20 (d, 2 H), 6.72 (d, 1 H), 6.63 (d, 1 H), 6.57 (d, 2 H), 5.09 (br s, 1 H), 3.50 (t, 2 H), 1.72 (m, 3 H), 1.59 (m, 6 H), 1.26 (m, 2 H), 1.03 (m, 2 H); MS (FAB) m/z 286 (MH$^+$).

EXAMPLE 51

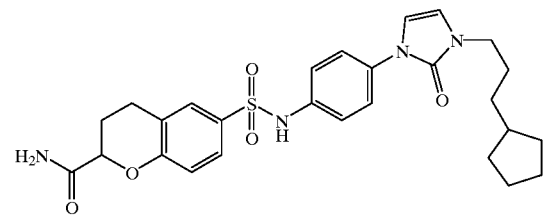

6-{4-[3-(3-Cyclopentyl-propyl)-2-oxo-2,3-dihydro-imidazol-1-yl]-phenylsulfamoyl}-chroman-2-carboxylic acid amide The title compound was prepared from Example 50 by the procedure described in Example 23. Yield 71%. $R_f$=0.1 (2:1 ethyl acetate/hexanes); H NMR (300 MHz, DMSO-$d_6$) δ 10.15 (s, 1 H), 7.53 (m, 4 H), 7.47 (s, 1 H), 7.37 (s, 1 H), 7.12 (d, 2 H), 6.95 (d, 1 H), 6.90 (d, 1 H), 6.72 (d, 1 H), 4.57 (dd, 1 H), 3.50 (t, 2 H), 2.77 (m, 1 H), 2.71 (m, 1 H), 2.11 (m, 1 H), 1.88 (m, 1 H), 1.71 (m, 3 H), 1.56 (m, 6 H), 1.24 (m, 2 H), 1.02 (m, 2 H); MS (ES) m/z 525 (MH$^+$).

EXAMPLE 52

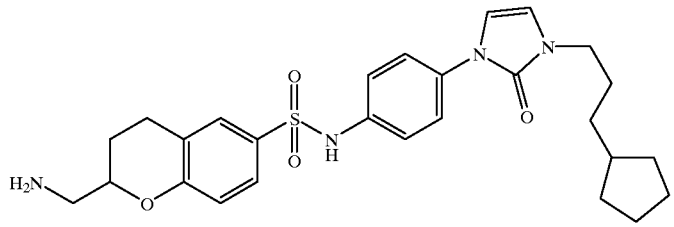

2-Aminomethyl-chroman-6-sulfonic acid {4-[3-(3-cyclopentyl-propyl)-2-oxo-2,3-dihydro-imidazol-1-yl]-phenyl}-amide The title compound was prepared from Example 51 by the procedure described in Example 26. Yield 28%. H NMR (300 MHz, CD$_3$OD) δ 7.41 (m, 4 H), 7.38 (d, 2 H), 7.05 (d, 2 H), 6.85 (m, 1 H), 5.56 (dd, 1 H), 4.10 (m, 2 H), 3.62 (m, 1 H), 3.24 (m, 2 H), 2.96 (m, 2 H), 2.77 (m, 2 H), 2.04 (m, 1 H), 1.79 (m, 3 H), 1.58 (m, 6 H), 1.33 (m, 2 H), 1.10 (m, 2 H); MS (ES) m/z 511 (MH$^+$).

EXAMPLE 53

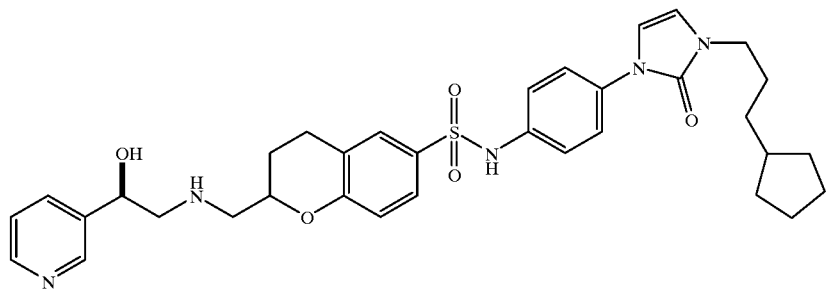

2-[(2-Hydroxy-2-pyridin-3-yl-ethylamino)-methyl]-chroman-6-sulfonic acid {4-[3-(3-cyclopentyl-propyl)-2-oxo-2,3-dihydro-imidazol-1-yl]-phenyl}-amide The title compound was prepared from Example 52 by the procedure described in Example 29. Yield 12%. Mp 90–92° C.; $R_f$=0.1 (9:1 ethyl acetate/methanol); H NMR (300 MHz, $CD_3OD$) δ 8.57 (s, 1 H), 8.44 (d, 1 H), 7.85 (d, 1 H), 7.42 (m, 5 H), 7.17 (d, 2 H), 6.82 (d, 1 H), 6.76 (d, 1 H), 6.63 (d, 1 H), 4.24 (m, 1 H), 3.64 (t, 2 H), 2.86 (m, 6 H), 1.78 (m, 6 H), 1.57 (m, 5 H), 1.32 (m, 2 H), 1.09 (m, 2 H); MS (ES) m/z 631 ($MH^+$).

Examples 54 to 56 were prepared in analogy to the procedure of Example 26.

| Example | Name | MS | $R_f$ |
|---|---|---|---|
| 54 | (±)-2-Aminomethyl-chroman-6-sulfonic acid [4-(4-methyl-5-oxo-4,5-dihydrotetrazol-1-yl)-phenyl]-amide | 417 ($MH^+$) | 0.1 (G) |
| 55 | (±)-2-Aminomethyl-chroman-6-sulfonic acid [4-(4-benzyl-5-oxo-4,5-dihydrotetrazol-1-yl)-phenyl]-amide | 493 ($MH^+$) (Cl) | 0.1 (G) |
| 56 | (±)-2-Aminomethyl-chroman-6-sulfonic acid [4-(4-cyclopentyl-methyl-5-oxo-4,5-dihydrotetrazol-1-yl)-phenyl]-amide | 485 ($MH^+$) (Cl) | 0.1 (G) |

Examples 57 to 59 were prepared in analogy to the procedure of Example 29 using Examples 54 to 56 as starting material.

| Example | Name | MS | $R_f$ |
|---|---|---|---|
| 57 | 2-[(2-Hydroxy-2-pyridin-3-yl-ethylamino)-methyl]-chroman-6-sulfonic acid [4-(4-methyl-5-oxo-4,5-dihydro-tretazol-1-yl)-phenyl]-amide | 538 ($MH^+$) | 0.2 (F) |
| 58 | 2-[(2-Hydroxy-2-pyridin-3-yl-ethyl-amino)-methyl]-chroman-6-sulfonic acid [4-(4-benzyl-5-oxo-4,5-dihydro-tretazol-1-yl)-phenyl]-amide | 614 ($MH^+$) | 0.3 (F) |
| 59 | 2-[(2-Hydroxy-2-pyridin-3-yl-ethyl-amino)-methyl]-chroman-6-sulfonic acid [4-(4-cyclopentylmethyl-5-oxo-4,5-dihydrotretazol-1-yl)-phenyl]-amide | 606 ($MH^+$) | 0.3 (F) |

EXAMPLE 60

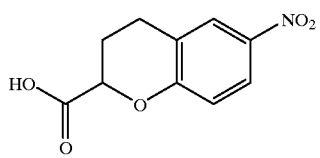

(±)-6-Nitro-chroman-2-carboxylic acid

To a solution of concentrated nitric acid (70%, 166 mL), at 0° C., was added the chroman acid, from Example 20, (10.0 g, 56.0 mmol) portionwise. The reaction mixture was stirred until all solids were dissolved (1 h) and was then poured onto ice (400 g). The fine precipitate was collected via filtration through a medium porosity sintered glass funnel. The crude precipitate was washed with water (2×100 mL) followed by brine (1×50 mL) and finally dried under vacuum at 60° C. for 24 h to afford (8.85 g, 70.4%) pure product. $R_f$=0.2 (methylene chloride:methanol 9:1); mp 110–111° C.; MS (FAB) m/z 224 ($MH^+$).

EXAMPLE 61

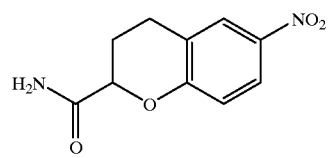

(±)-6-Nitro-chroman-2-carboxylic acid amide

To a solution of compound from example 60 (1.5 g, 6.7 mmol) and N,N-dimethylformamide (3 drops) in tetrahydrofuran (45 mL) at 0° C. was added oxalyl chloride (1.45 g, 11.4 mmol, 1.0 mL). The reaction mixture was stirred at 0° C. for 1 h and at room temperature for 3 h. The solvent was evaporated and crude taken to next step.

To a 3-neck flask containing a condenser, argon adapter, and a thermometer, was placed a solution of 6-nitro-2-chlorocarbonyl-benzotetrahydropyran (1.5 g, 7.0 mmol) and tetrahydrofuran (45 mL). The temperature was brought to −78° C. with an acetone/dry ice bath and an excess of ammonia gas was condensed into the reaction mixture. The reaction mixture was stirred at −78° C. for 1 h. The ice bath was removed and the reaction mixture stirred at room temperature for 1 h. The precipitate was collected via filtration and was washed with water (3×50 mL), followed by hexane (2×50 mL). The solid was dried under vacuum at 60° C. for 24 h to afford (6.8 g, 99%). $R_f$=0.6 (methylene chloride:methanol 95:5); MS (FAB) m/z 221 ($MH^+$).

EXAMPLE 62

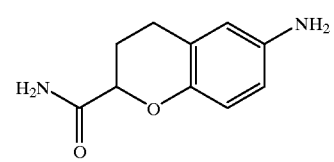

(±)-6-Amino-chroman-2-carboxylic acid amide

A mixture of compound from example 61 (6.75g, 30.0 mmol), absolute ethanol (700 mL) and 10% activated palladium on carbon (1.35 g) was placed under a hydrogen balloon for 24 h. The product was filtered through celite and the solvent was evaporated to afford the title compound (5.76 g, 100%). $R_f$=0.4 (methylene chloride:methanol 95:5); MS (FAB) m/z 193 ($MH^+$).

EXAMPLE 63

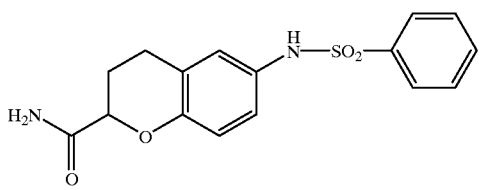

(±)-6-Phenylsulfonamide-chroman-2-carboxylic acid amide

To a solution of compound from example 62 (1.88 g, 9.8 mmol) and pyridine (0.78 g, 9.8 mmol, 0.8 mL) in tetrahydrofuran (90 mL) at 0° C. was added benzene sulfonyl chloride (1.72 g, 9.8 mmol, 1.24 mL) via syringe. The ice bath was removed and reaction mixture was refluxed for 18 h. Solvent was evaporated and the residue suspended in ethyl acetate (250 mL) and was then washed with water (1×50 mL), 5% HCl (1×50 mL), saturated sodium carbonate (1×50 mL) and brine (1×50 mL). The product was dried (MgSO$_4$), filtered and evaporated to yield 1 g crude product, which was suspended in hexane:ethyl acetate (1:1) and collected by filtration and finally washed with hexane (50 mL) and dried under vacuum at 60° C. for 24 h to afford (3.24 g, 99.6%). R$_f$=0.4 in (hexane:ethyl acetate, 1:1); MS (FAB) m/z 333 (MH$^+$).

EXAMPLE 64

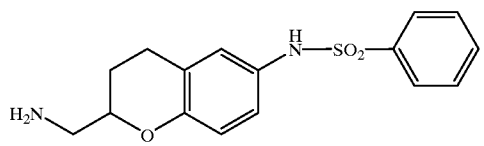

(±)-6-Phenylsulfonamide-2-aminomethylchroman

To a solution compound from example 63 (3.1 g, 9.3 mmol) in tetrahydrofuran (150 mL) at 0° C., under argon, was added boron methyl sulfide (2M in tetrahydrofuran) (27.9 ml, 55.8 mmol) via syringe. The ice bath was removed and the reaction mixture refluxed for 18 h. The reaction mixture was cooled to 0° C. and methanol (21 mL) was slowly added. When gas evolution ceased, 6N HCl (27 mL) was added slowly and the solution was refluxed for 1 h. The solution was cooled to 0° C. and the pH adjusted to 12 with 20% sodium hydroxide. The aqueous layer was extracted with ethyl acetate (2×200 mL). The organic layer was washed with water (2×25 mL), dried (MgSO$_4$), filtered and evaporated to yield crude product (1.6 g). The crude product was chromatographed on silica and eluted with methylene chloride:methanol 9:1 to afford pure product (1.0 g, 32%) as a viscous oil. R$_f$=0.4 (J); MS (FAB) m/z (MH$^+$).

EXAMPLE 65

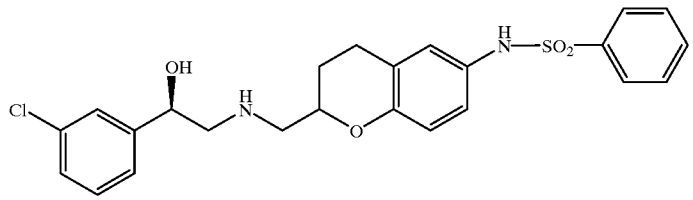

2-{[(3-chlorophenyl)-2-hydroxy-ethylamino]-methyl}-chroman-6-yl-(4-chloro)-bezenesulfonamide To a solution of the compound from Example 64 (0.25 g, 0.74 mmol) in absolute ethanol (15 mL), and dimethylformamide (1 mL) under argon, was added (R)-(+)-3-chlorostyrene oxide (0.11 g, 0.7 mmol) in tetrahydrofuran (2 mL) via syringe at reflux. The reaction mixture was refluxed for 24 h. The solvent was evaporated and the crude product passed through silica and eluted on a gradient from 48:48:5 hexane/ethyl cetate/methanol to 45:45:10 hexane/ethyl acetate/methanol. The product was chromatographed on silica and eluted with 9:1 methylene chloride/methanol to afford pure product (77 mg, 21%) of the mono-alkylated product R$_f$=0.3 (A); MS (FAB) m/z 473 (MH$^+$); $^1$H NMR (d$_6$-DMSO 300 MHz) δ 7.95 (s, 1 H), 7.66 (m, 2 H), 7.53 (m, 3 H), 0.27 (m, 3 H), 6.71 (m, 2 H), 6.55 (d, 1 H, J=8.46 Hz), 5.44 (m, 1 H), 4.62 (m, 1 H), 3.96 (m, 1 H), 2.86 (s, 2 H), 2.62 (m, 6 H), 1.86 (m, 1 H).

Examples 66 to 72 were prepared from Example 62 in analogy to the procedures described in Examples 63 and either (R)-(+)-3-chlorostyrene oxide or Example 7.

| Example | Name | MS | R$_f$ |
|---|---|---|---|
| 66 | N-(2-{[2-(3-chloro-phenyl)-2-hydroxy-ethylamino]-methyl}-chroman-6-yl)-4-Chloro-benzenesulfonamide | 507 (MH$^+$) | 0.3 (A) |
| 67 | N-(2-{[2-(3-chloro-phenyl)-2-hydroxy-ethylamino]-methyl}-chroman-6-yl)-4-isopropyl-benzene-sulfonamide | 515 (MH$^+$) | 0.2 (A) |
| 68 | N-(2-{[2-(3-chloro-phenyl)-2-hydroxy-ethylamino]-methyl}-chroman-6-yl)-4-methyl-benzene-sulfonamide | 487 (MH$^+$) | 0.2 (A) |
| 69 | N-(2-{[2-(3-chloro-phenyl)-2-hydroxy-ethylamino]-methyl}-chroman-6-yl)-4-methoxy-benzene-sulfonamide | 503 (MH$^+$) | 0.3 (A) |
| 70 | N-(2-{[2-(3-chloro-phenyl)-2-hydroxy-ethylamino]-methyl}-chroman-6-yl)-4-[4-(3-cyclopentyl-propyl)-5-oxo-4,5-dihydro-tetrazol-1-yl]-benzenesulfonamide | 667 (MH$^+$) | 0.1 (A) |
| 71 | N-{2-[(2-hydroxy-2-pyridin-3-yl-ethylamino)-methyl]-chroman-6-yl)-4-Chloro-benzenesulfonamide | 474 (MH$^+$) | 0.4 (H) |
| 72 | N-{2-[(2-hydroxy-2-pyridin-3-yl-ethylamino)-methyl]-chroman-6-yl)-4-isopropyl-benzenesulfonamide | 482 (MH$^+$) | 0.3 (A) |

EXAMPLE 73

| | |
|---|---|
| A capsule formula is prepared from | |
| 2-[(2-Hydroxy-2-pyridin-3-yl-ethylamino)-methyl]-chroman-6-sulfonic acid {4-[3-(3-cyclopentyl-propyl)-2-oxo-2,3-dihydro-imidazol-1-yl]-phenyl}-amide | 40 mg |
| Starch | 109 mg |
| Magnesium steatrate | 1 mg |

The components are blended, passed through an appropriate mesh sieve, and filled into hard geltatin capsules.

EXAMPLE 74

| | |
|---|---:|
| A tablet is prepared from | |
| (2S)-2-[((2R)-2-Hydroxy-2-pyridin-3-yl-ethylamino)-methyl]-chroman-6-sulfonic acid {4-[4-(3-cyclopentyl-propyl)-5-oxo-4,5-dihydro-tetrazol-1-yl]-phenyl}-amide | 25 mg |
| Cellulose, microcrystaline | 200 mg |
| Colloidal silicon dioxide | 10 mg |
| Stearic acid | 5.0 mg |

The ingredients are mixed and compressed to form tablets.

EXAMPLE 75

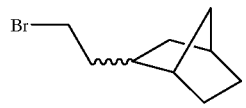

2-(2-Bromo-ethyl)-bicyclo[2.2.1]heptane

2-Norbornane acetic acid (15 g, 97 mmol) was dissolved in anhydrous tetrahydrofuran (150 mL) and treated dropwise with lithium aluminum hydride (195 mL, 1 M in tetrahydrofuran) at 0° C. The reaction was stirred for three days then quenched by dropwise addition of water (50 mL). The reaction was diluted with diethyl ether (300 mL) and washed with water (3×200 mL). The combined organic phases were dried (MgSO$_4$), filtered, and concentrated to yield an oil. The product was passed through a pad of silica gel to yield 2-bicyclo[2.2.1]hept-2-yl-ethanol as a colorless oil (13.1 g, 96%).

2-Bicylco[2.2.1]hept-2-yl-ethanol (13.0 g, 93 mmol) was dissolved in acetonitrile (200 mL) and treated with dibromotriphenylphosphorane (47.0 g, 0.11 mol). After 1.5 hours the mixture was quenched with water (10 mL), diluted with diethyl ether (400 mL), and washed with water (2×400 mL). The organic phase was dried (MgSO$_4$) and concentrated to yield an oil. The product was passed through a pad of silica gel to yield 2-(2-bromo-ethyl)-bicyclo[2.2.1]heptane as a colorless oil (18 g, 95%). $^1$H NMR (CDCl$_3$, 300 MHz) δ 3.37 (t, 7.4 Hz, 2 H), 2.22 (m, 1 H), 1.97 (m, 1 H), 1.86 (m, 1 H), 1.7–1.4 (m, 5 H), 1.3–0.9 (m, 5 H); MS (FAB) m/z 203 (MH$^+$).

EXAMPLE 76

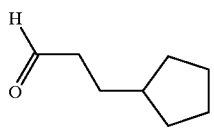

3-Cyclopentyl-propionaldehyde

3-Cyclopentyl-1-propanol (15.0 g, 117 mmol) was dissolved in dichloromethane (600 mL) and treated with Celite (50 g) and pyridinium chlorochromate (50.0 g, 232 mmol). The reaction was stirred at room temperature for 24 hours. The reaction was found to be complete by thin layer chromatography (stain: potassium permanganate) and filtered through a pad of silica (dichloromethane) to afford 3-cyclopentyl-propionaldehyde as an oil (10.3 g, 70%). $^1$H NMR (CDCl$_3$, 300 MHz) δ 11.1–10.8 (br s, 1 H), 2.36 (t, 7.73 Hz, 2 H), 1.8–1.5 (m, 9 H), 1.09 (m, 2 H).

EXAMPLE 77

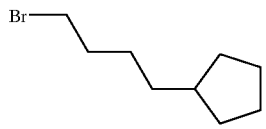

(4-Bromo-butyl)-cyclopentane

Methoxymethyl triphenylphosphonium chloride (36 g, 0.11 mol) was suspended in anhydrous tetrahydrofuran (400 mL) and treated with potassium tert-butoxide (12.8 g, 0.11 mol). The reaction stirred for 10 minutes and 3-cyclopentyl-propionaldehyde (10.29 g, 0.082 mol, Example 76) was added dropwise as a solution in anhydrous tetrahydrofuran (100 mL). After 24 hours the reaction was quenched with water. The reaction was diluted with diethyl ether (600 mL) and washed with water (3×300 mL). The organic phase was dried (MgSO$_4$) and concentrated to afford an oil. The oil was taken up in tetrahydrofuran (50 mL) and concentrated hydrochloric acid (20 mL) was added. After six hours, the reaction was diluted with diethyl ether and washed with water (2×200 mL). The organic phase was dried (MgSO$_4$), filtered, and concentrated to yield an oil. The oil was filtered through a pad of silica gel to yield 4-cyclopentyl-butyraldehyde as an oil (6.21 g, 54%).

4-Cyclopentyl-butyraldehyde (4.9 g, 35 mmol) was taken up in ethanol (100 mL) and treated slowly with sodium borohydride (1.72 g, 4.54 mmol). The reaction was stirred for three days and quenched with water (10 mL). The reaction was diluted with dichloromethane (200 mL) and washed with water (2×100 mL). The organic phase was dried (MgSO$_4$), filtered, and concentrated to yield an oil. The product was passed through a pad of silica to yield 4-cyclopentyl-butan-1-ol as a colorless oil (3.12 g, 63%).

A solution of 4-cyclopentyl-butan-1-ol (3.1 g, 22 mmol) in acetonitrile (200 mL) was treated with dibromotriphenylphosphorane (10.1 g, 23.9 mmol). The reaction was stirred for two hours and quenched with water (10 mL). The reaction was diluted with dichloromethane (300 mL) and washed with water (3×100 mL). The organic phase was dried (MgSO$_4$), filtered, and concentrated to yield an oil. The product was passed through a pad of silica to yield (4-bromo-butyl)-cyclopentane as a colorless oil (3.37 g, 76%). $^1$H NMR (CDCl$_3$, 300 MHz) δ 3.42 (t, 7.0 Hz, 2 H), 1.9–1.7 (m, 4 H), 1.6–1.3 (m, 9 H), 1.07 (m, 2 H).

Examples 78 and 79 were prepared in analogy to the procedure of Example 9.

| Example | Name | MS |
|---|---|---|
| 78 | 1-(4-Nitrophenyl)-4-(3-phenylpropyl)-1,4-dihydrotetrazol-5-one | 326 (MH$^+$, Cl) |
| 79 | 1-[3-(4-Fluoro-phenoxy)-propyl]-4-(4-nitro-phenyl)-1,4-dihydro-tetrazol-5-one | 360 (MH$^+$, Cl) |

EXAMPLE 80

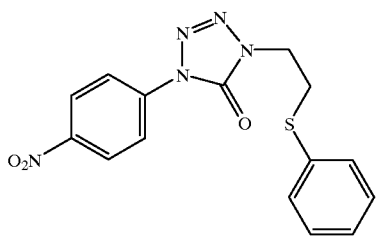

1-(4-Nitrophenyl)-4-(2-phenylsulfanylethyl)-1,4-dihydrotetrazol-5-one 1-(4-Nitrophenyl)-5-tetrazolone (Example 8) (153 mg, 0.74 mmol), 2-hydroxyethyl phenyl sulfide (0.1 mL, 0.74 mmol), and triphenylphosphine (194 mg, 0.74 mmol) were suspended in tetrahydrofuran (2.5 mL). Diethyl azodicarboxylate (0.12 mL, 0.74 mmol) was added dropwise. After 12 hours the mixture was concentrated in vacuo to an oil. Silica gel chromatography (9:1 hexane/ethyl acetate) afforded a solid (230 mg, 90%). $^1$H NMR (CDCl$_3$, 300 MHz) δ 8.30 (d, 9.2 Hz, 2 H), 8.13 (d, 9.2 Hz, 2 H), 7.37 (d, 7.0 Hz, 2 H), 7.20 (d, 7.0 Hz, 2 H), 7.12 (m, 1 H), 4.19 (t, 6.6 Hz, 2 H), 3.32 (t, 6.6 Hz, 2 H); MS (CI) m/z 344 (MH$^+$).

Examples 81 and 82 were prepared in analogy to the procedure of Example 9.

| Example | Name | MS | R$_f$ |
|---|---|---|---|
| 81 | 1-[3-(4-Methoxyphenyl)propyl]-4-(4-nitrophenyl)-1,4-dihydro-tetrazol-5-one | 356 (MH$^+$, CI) | 0.38 (N) |
| 82 | 1-(2-Cyclopentyloxyethyl)4-(4-nitrophenyl)-1,4-dihydrotetrazol-5-one | 320 (MH$^+$, CI) | 0.42 (N) |

EXAMPLE 83

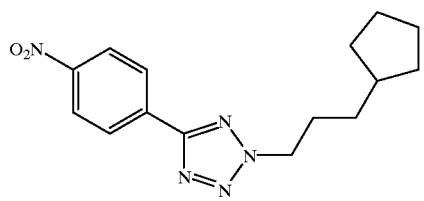

2-(3-Cyclopentyl-propyl)-5-(4-nitro-phenyl)-2N-tetrazole

To a suspension of 60% sodium hydride in mineral oil (424 mg, 10.6 mmol) in anhydrous N,N-dimethylformamide (10 mL) was added 5-(4-nitrophenyl)-1H-tetrazole (2.0 g, 10.5 mmol) as a solution in N,N-dimethylformamide (20 mL). After 10 minutes, 3-cyclopentyl-1-iodopropane (2.75 g, 11.6 mmol, 1.1 equiv) was added. After two days the mixture was poured onto ice, and the resulting precipitate was collected by filtration. The solid was washed with water and dried at 50° C. under vacuum to afford the title compound (3.09 g, 98%) as a low melting yellow solid. $^1$H NMR (DMSO-d$_6$, 300 MHz) δ 8.39 (d, 8.8Hz, 2 H), 8.30 (d, 8.8Hz, 2 H), 4.76 (t, 7.0Hz, 2 H), 1.98 (m, 2 H), 1.72 (m, 3 H), 1.4–1.5 (m, 4 H), 1.29 (m, 2 H), 1.02 (m, 2 H); MS (CI) 302 (MH$^+$); R$_f$=0.90 (C).

EXAMPLE 84

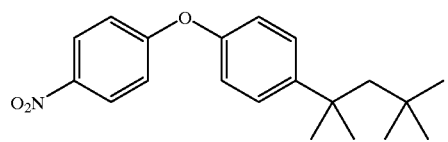

4-[4-(1,1,3,3-Tetramethyl-butyl)-phenoxy]-nitrobenzene

A solution of 1-fluoro-4-nitrobenzene (3.4 g, 0.024 mol), K$_2$CO$_3$ (6.6 g, 48 mmol) and 4-(tert-octyl)phenol (5.0 g, 0.024 mol) in dimethylformamide (50 mL) was heated at reflux for 24 hours. The mixture was allowed to cooled to room temperature, diluted with water (200 mL), and extracted with ethyl acetate (250 mL). The organic phase was washed with water (5×100 mL), dried (Na$_2$SO$_4$), and concentrated under reduced pressure to afford the desired product as a yellow solid (7.8 g, 100%): $^1$H NMR (DMSO-d$_6$, 300 MHz) δ 8.24 (d, 9.2 Hz, 2 H), 7.48 (d, 8.8 Hz, 2 H), 7.09–7.05 (m, 4H), 1.72 (s, 2 H), 1.34 (s, 6 H), 0.69 (s, 9 H); MS (FAB) m/z 328 (MH$^+$); R$_f$=0.92 (15:85 ethyl acetate/hexane).

EXAMPLE 85

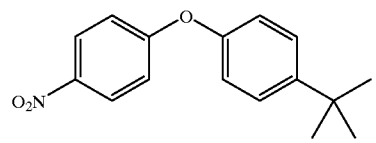

4-(4-tert-Butyl-phenoxy)-nitrobenzene The title compound was made in analogy to the procedure of Example 84. MS (FAB) m/z 272 (MH$^+$); TLC R$_f$=0.81 (10:90 ethyl acetate/hexane).

Example 86 through Example 90 were prepared in analogy to the procedure of Example 29.

| Example | Name | MS | R$_f$ |
|---|---|---|---|
| 86 | 2-[(2R)-(2-Hydroxy-2-pyridin-3-yl-ethylamino)-methyl]-chroman-6-sulfonic acid (4-phenoxyphenyl)-amide | 532 (MH$^+$) | 0.17 (C) |
| 87 | 2-[(2H)-(2-Hydroxy-2-pyridin-3-yl-ethylamino)-methyl]-chroman-6-sulfonic acid {4-[2-(3-cyclopentyl-propyl)-2N-tetrazol-5-yl]-phenyl}-amide | 618 (MH$^+$, HPLC MS) | 0.10 (D) |
| 88 | 2-[(2H)-(2-Hydroxy-2-pyridin-3-yl-ethylamino)-methyl]-chroman-6-sulfonic acid [4-(5-oxo-4-propyl-4,5-dihydro-tetrazol-1-yl)-phenyl]-amide | 566 (MH$^+$) | 0.83 (J) |
| 89 | 2-[(2R)-(2-Hydroxy-2-pyridin-3-yl-ethylamino)-methyl]-chroman-6-sulfonic acid {4-[4-(4-methyl-pentyl)-5-oxo-4,5-dihydro-tetrazol-1-yl]-phenyl}amide | 608 (MH$^+$) | 0.20 (C) |
| 90 | 2-[((2R)-Hydroxy-2-pyridin-3-ylethyl amino)-methyl]-chroman-6-sulfonic acid (4-{4-[3-(4-fluorophenoxy)-propyl]-5-oxo-4,5-dihydrotetrazol-1-yl}-phenyl)amide | 676 (MH$^+$) | |

EXAMPLE 91

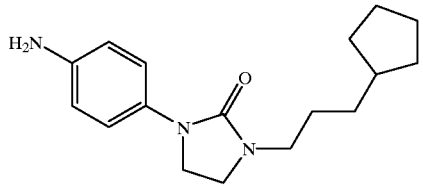

1-(4-Amino-phenyl)-3-(3-cyclopentyl-propyl)-imidazolidin-2-one

The title compound was prepared from 1-(4-nitro-phenyl)-3-(3-cyclopentyl-propyl)-imidazol-2-one (Example 50) by the method described in Example 50. mp 97–100° C.; $^1$H NMR (DMSO-$d_6$, 300 MHz) δ 7.14 (d, 8.8 Hz, 2 H), 6.51 (d, 8.8 Hz, 2 H), 4.77 (br s, 2 H), 3.65 (t, 7.0 Hz, 2 H), 3.34 (t, 6.0 Hz, 2 H), 3.10 (t, 7.0 Hz, 2 H), 1.72 (m, 3 H), 1.46 (m, 6 H), 1.27 (m, 2 H), 1.05 (m, 2 H); MS (FAB) m/z 288 (MH$^+$); R$_f$=0.13 (I).

EXAMPLE 92

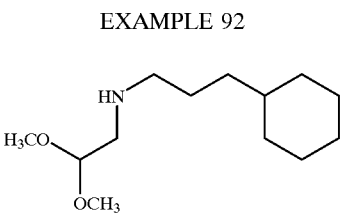

(3-Cyclohexyl-propyl)-(2,2-dimethoxy-ethyl)-amine

1-Chloro-3-cyclohexylpropane (11.1 g, 69.0 mmol), 2-aminoacetaldehyde (15.0 mL, 138.0 mmol, 2.0 equiv) and sodium iodide (2.1 g, 14.0 mmol, 0.2 equiv) were combined in anhydrous N,N-dimethylformamide (20 mL). The solution was stirred over solid potassium carbonate (9.66 g, 70 mmol) at 80° C. for 16 hours. The mixture was cooled to room temperature and diluted with water. The solution was extracted with ethyl acetate (2×). The combined organic phase was washed with brine (3×), dried (MgSO$_4$), and concentrated in vacuo to a crude oil. Silica gel chromatography (gradient elution from 50:50 hexane/ethyl acetate to 100% ethyl acetate) yielded the title compound as a yellow oil (12.0 g, 76%). $^1$H NMR (CDCl$_3$, 300 MHz) δ 4.46 (t, 5.5 Hz, 1 H), 3.38 (s, 6 H), 2.71 (d, 5.5 Hz, 2 H), 2.57 (t, 7.4 Hz, 2 H), 1.75–1.60 (m, 3 H), 1.47 (m, 2 H), 1.17 (m, 8 H), 0.86 (m, 2 H); R$_f$=0.27 (50:50 hexane/ethyl acetate).

EXAMPLE 93

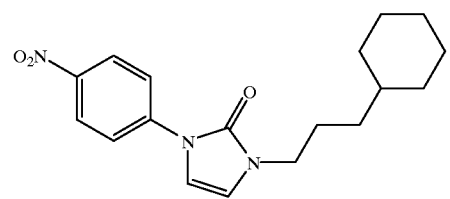

1-(3-Cyclohexyl-propyl)-3-(4-nitro-phenyl)-1,3-dihydro-imidazol-2-one

The title compound was prepared from (3-cyclohexyl-propyl)-(2,2-dimethoxy-ethyl)-amine (Example 92) by the method described in Example 49. A yellow solid was obtained in 95% yield. mp 153–156° C.; $^1$H NMR (CDCl$_3$, 300 MHz) δ 8.26 (d, 9.2 Hz, 2 H), 7.87 (d, 9.2 Hz, 2 H), 6.66 (d, 2.9 Hz, 1 H), 6.40 (d, 2.9 Hz, 1 H), 3.62 (t, 7.4 Hz, 2 H), 1.67 (m, 7 H), 1.23–1.10 (m, 6 H), 0.86 (m, 2 H); MS (CI) m/z 330 (MH$^+$); R$_f$=0.79 (50:50 hexane/ethyl acetate).

EXAMPLE 94

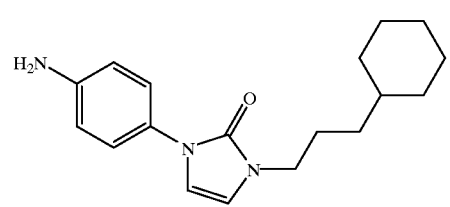

1-(4-Amino-phenyl)-3-(3-cyclohexyl-propyl)-1,3-dihydro-imidazol-2-one 1-(3-Cyclohexyl-propyl)-3-(4-nitro-phenyl)-1,3-dihydro-imidazol-2-one (15.4 g, 46.8 mmol) and tin chloride dihydrate (53.0 g, 234.5 mmol, 5.0 equiv) were combined in ethanol and heated at 70° C. for two hours. The mixture was cooled to 25° C. and poured onto ice (500 mL). The aqueous mixture was adjusted to pH=8 with 1 N aqueous sodium hydroxide solution. The aqueous phase was extracted with ethyl acetate (3×). The combined organic phase was washed with saturated aqueous sodium chloride solution, dried (MgSO$_4$), and concentrated in vacuo to an orange solid (13.4 g, 95%). Mp 83–85° C.; $^1$H NMR (CDCl$_3$, 300 MHz) δ 7.26 (d, 8.5 Hz, 2 H), 6.64 (d, 8.5 Hz, 2 H), 6.40 (d, 2.9 Hz, 1 H), 6.24 (d, 2.9 Hz, 1 H), 3.70 (br s, 2 H), 3.57 (t, 7.4 Hz, 2 H), 1.64 (m, 7 H), 1.19 (m, 6 H), 0.85 (m, 2 H); MS (CI) m/z 300 (MH$^+$); R$_f$=0.24 (50:50 hexane/ethyl acetate).

EXAMPLE 95

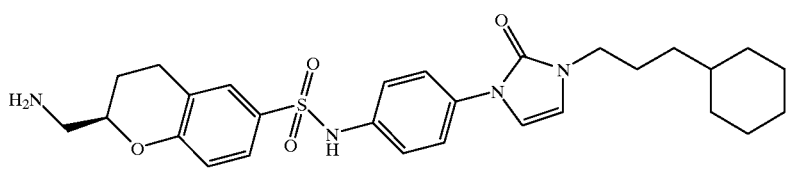

(2R)-2-Aminomethyl-chroman-6-sulfonic acid {4-[3-(3-cyclohexyl-propyl)-2-oxo-2,3-dihydro-imidazol-1-yl)-phenyl}-amide 6-{4-[3-(3-Cyclohexyl-propyl)-2-oxo-2,3-dihydro-imidazol-1-yl]-phenylsulfamoyl}-chroman-(2R)-2-carboxylic acid amide (3.0 g, 5.57 mmol) was suspended in anhydrous tetrahydrofuran (90 mL) and sodium bis(2-methoxyethoxy)aluminum hydride (65% in toluene, 7.0 mL, 23.3 mmol, 4.2 equivalents) was added. The solution was heated at reflux for three hours, cooled to room temperature, and 1 N aqueous sodium hydroxide solution (5 mL) was added dropwise. The mixture was diluted with ethyl acetate and passed through a pad of silica gel. The silica gel was washed thoroughly with 50:50 ethyl acetate/methanol. The combined filtrate was concentrated in vacuo to a solid. Silica gel chromatography (gradient elution from 100% ethyl acetate to 60:40 ethyl acetate/methanol) afforded the title compound as a pale yellow solid (2.60 g, 89%). mp 106–110° C.; $^1$H NMR (CD$_3$OD, 300 MHz) δ 7.50 (m, 2 H), 7.43 (d, 8.8 Hz, 2 H), 7.16 (d, 8.8 Hz, 2 H), 6.87 (d, 8.5 Hz, 1 H), 6.76 (d, 2.9 Hz, 1 H), 6.63 (d, 2.9 Hz, 1 H), 4.15 (m, 1 H), 3.62 (t, 7.0Hz, 2 H), 2.80 (m, 3 H), 2.10 (m, 1 H), 1.69 (m, 8 H), 1.23 (m, 7 H), 0.85 (m, 2 H); LC/MS m/z 525 (MH$^+$); R$_f$=0.14 (80:20 ethyl acetate/methanol).

EXAMPLE 96

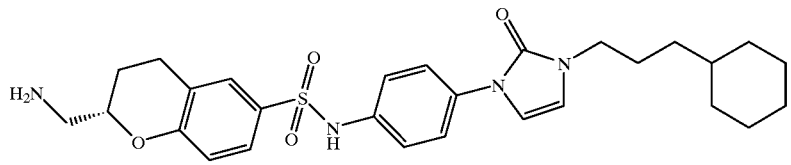

(2S)-2-Aminomethyl-chroman-6-sulfonic acid {4-[3-(3-cyclohexyl-propyl)-2-oxo-2,3-dihydro-imidazol-1-yl]-phenyl}-amide The title compound was prepared from 6-{4-[3-(3-cyclohexyl-propyl)-2-oxo-2,3-dihydro-imidazol-1-yl]-phenylsulfamoyl}-chroman-(2S)-2-carboxylic acid amide in 69% yield by the method described in Example 95. mp 108–110° C.; $^1$H NMR (CD$_3$OD, 300 MHz) δ 7.50 (m, 2 H), 7.43 (d, 8.8 Hz, 2 H), 7.16 (d, 8.8 Hz, 2 H), 6.87 (d, 8.5 Hz, 1 H), 6.76 (d, 2.9 Hz, 1 H), 6.63 (d, 2.9 Hz, 1 H), 4.15 (m, 1 H), 3.62 (t, 7.0 Hz, 2 H), 2.80 (m, 3 H), 2.10 (m, 1 H), 1.69 (m, 8 H), 1.23 (m, 7 H), 0.85 (m, 2 H); MS (ES) m/z 525 (MH$^+$); R$_f$=0.14 (K).

EXAMPLE 97

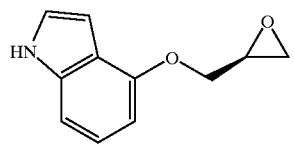

(4S)-4-Oxiranylmethoxy-1N-indole

To a suspension of 60% sodium hydride in mineral oil (88 mg, 2.2 mmol) in N,N-dimethylformamide (DMF, 2 mL) was added 4-hydroxyindole (0.27 g, 2.0 mmol) as a solution in DMF (5 mL). The mixture was stirred for 20 minutes. (2S)-(+)-glycidyl-3-nitrobenzene sulfonate (0.52 g, 2.0 mmol) was added as a solution in DMF (3 mL), and the mixture was stirred for one hour. The reaction was poured onto ice, and the aqueous mixture was extracted with ethyl acetate. The organic phase was washed with brine, dried (Na$_2$SO$_4$), and concentrated in vacuo to a crude solid. Silica gel chromatography (50:50 hexane/ethyl acetate) afforded the title compound as a brown oil (0.315 g, 83%). $^1$H NMR (DMSO-d$_6$, 300 MHz) δ 11.08 (br s, 1 H), 7.21 (s, 1 H), 6.99 (m, 2 H), 6.47 (m, 2 H), 4.40 (dd, 11.4 Hz, 2.6 Hz, 1 H), 3.29 (m, 1 H), 3.19 (m, 1 H), 2.76 (m, 1 H); MS (EI) m/z 189 (M$^+$); R$_f$=0.80 (50:50 hexane/ethyl acetate).

Example 98 to Example 113 were prepared by the method described in Example 29 and purified by methods described in Example 38 and Example 41.

| Example | Name | MS | R$_f$ |
|---|---|---|---|
| 98 | 2-[(2R)-(2-Hydroxy-2-pyridin-3-yl-ethylamino)-methyl]-chroman-6-sulfonic acid {4-[3-(3-cyclopentyl-propyl)-2-oxo-imidazolidin-1-yl]-phenyl}-amide | 634 (MH$^+$) | 0.10 (D) |
| 99 | (2R)-2-[{(2R)-2-Hydroxy-2-pyridin-3-yl-ethylamino)-methyl]-chroman-6-sulfonic acid {4-[3-3-cyclohexyl-propyl)-2-oxo-2,3-dihydroimidazol-1-yl]-phenyl}-amide; hydrate | 646 (MH$^+$) | 0.10 (D) |

-continued

| Example | Name | MS | R$_f$ |
|---|---|---|---|
| 100 | (2S)-2-[{(2R)-2-Hydroxy-2-pyridin-3-yl-ethylamino)-methyl]-chroman-6-sulfonic acid {4-[3-3-cyclohexyl-propyl)-2-oxo-2,3-dihydroimidazol-1-yl]-phenyl}-amide; hydrate | 646 (MH$^+$) | 0.10 (D) |
| 101 | 4-[4-(3-Cyclohexyl-propyl)-5-oxo-4,5-dihydrotetrazol-1-yl]-N-((2R)-2-{[(2R)-2-hydroxy-3-(1N-indol-4-yloxy)-propylamino]-methyl}-chroman-6-yl)-benzenesulfonamide | 715 (M$^+$, HPLC/MS) | 0.53 (B) |
| 102 | 2-[(2-Hydroxy-2-pyridin-3-yl-ethylamino)-methyl]-chroman-6-sulfonic acid [4-(4-tert-butyl-phenoxy)-phenyl]-amide | 588 (MH$^+$) | 0.50 (B) |
| 103 | 2-[(2-Hydroxy-2-pyridin-3-yl-ethylamino)-methyl]-chroman-6-sulfonic acid {4-[4-(1,1,3,3-tetramethyl-butyl)-phenoxy]-phenyl}-amide | 644 (MH$^+$); | 0.33 (J) |
| 104 | 2-[(2R)-(2-Hydroxy-2-pyridin-3-ylethylamino)methyl]chroman-6-sulfonic acid {4-[4-(3-cyclopentylpropyl)-5-oxo-4,5-dihydrotetrazol-1-yl]-3-methoxyphenyl}amide | 663 (MH$^+$, electrospray) | 0.04 (L) |
| 105 | N-((2R)-2-{[3-(4-Acetyl-3-hydroxy-2-propylphenoxy)-2-hydroxy-propylamino]-methyl}-chroman-6-yl)-4-[(3-cyclohexyl- | 777 (MH$^+$, electrospray) | 0.65 (K) |

| Example | Name | MS | $R_f$ |
|---|---|---|---|
| | propyl)-5-oxo-4,5-dihydro-tetrazol-1-yl]benzenesulfonamide | | |
| 106 | 2-[(2R)-(2-Hydroxy-2-pyridin-3-yl-ethylamino)-methyl]-chroman-6-sulfonic acid {4-[4-(3-cyclopentyl-butyl)-5-oxo-4,5-dihydro-tetrazol-1-yl]-phenyl}-amide | 648 (MH$^+$) | 0.2 (C) |
| 107 | 2-[(2R)-(2-Hydroxy-2-pyridin-3-yl-ethylamino)-methyl]-chroman-6-sulfonic acid {4-[4-(4-cyclopentyl-butyl)-5-oxo-4,5-dihydro-tetrazol-1-yl]-phenyl}-amide | 648 (MH$^+$) | 0.2 (C) |
| 108 | 2-[(2R)-(2-Hydroxy-2-pyridin-3-yl-ethylamino)-methyl]-chroman-6-sulfonic acid {4-[4-(4-tert-butyl-benzyl)-5-oxo-4,5-dihydro-tetrazol-1-yl]-phenyl}-amide | 550 (MH$^+$) | 0.3 (C) |
| 109 | (2R)-[((2R)-2-Hydroxy-2-pyridin-3-yl-ethylamino)-methyl]-chroman-6-sulfonic acid {4-[4-(2-bicyclo[2.2.1]hept-2-yl-ethyl)-5-oxo-4,5-dihydro-tetrazol-1-yl]-phenyl}-amide | 646 (MH$^+$) | 0.21 (C) |
| 110 | (2R)-[((2R)-Hydroxy-2-pyridin-3-ylethylamino)methyl]chroman-6-sulfonic acid {4-[5-oxo-4-(3-phenylpropyl)-4,5-dihydrotetrazol-1-yl]phenyl}amide | 642 (MH$^+$) | 0.24 (O) |
| 111 | (2S)-[((2R)-Hydroxy-2-pyridin-3-ylethylamino)methyl]chroman-6-sulfonic acid {4-[5-oxo-4-(2-phenylsulfanylethyl)-4,5-dihydrotetrazol-1-yl]phenyl}amide | 660 (MH$^+$) | 0.27 (O) |
| 112 | (2R)-[(2R)-Hydroxy-2-pyridin-3-ylethylamino)methyl]chroman-6-sulfonic acid {4-[5-oxo-4-(2-phenylsulfanylethyl)-4,5-dihydro-tetrazol-1-yl]phenyl}amide | 660 (MH$^+$) | 0.27 (O) |
| 113 | (2S)-[((2R)-Hydroxy-2-pyridin-3-ylethylamino)methyl]chroman-6-sulfonic acid {4-[5-oxo-4-(3-phenylpropyl)-4,5-dihydrtetrazol-1-yl]phenyl}amide | 642 (MH$^+$) | 0.24 (O) |
| 114 | (2S)-[((2R)-Hydroxy-2-pyridin-3-ylethylamino)methyl]chroman-6-sulfonic acid (4-{4-[3-(4-methoxyphenyl)propyl]-5-oxo-4,5-dihydrotetrazol-1-yl}phenyl)amide | 672 (MH$^+$) | 0.28 (O) |
| 115 | (2S)-[((2R)-Hydroxy-2-pyridin-3-ylethylamino)methyl]chroman-6-sulfonic acid {4-[4-(2-cyclopentyl-oxyethyl)-5-oxo-4,5-dihydrotetra-zol-1-yl]phenyl}amide | 636 (MH$^+$, electrospray) | 0.27 (O) |

Example 116 to Example 117 were prepared in analogy to the procedure of Example 35.

| Example | Name | MS | $R_f$ |
|---|---|---|---|
| 116 | (2S)-{[2-(6-Aminopyridin-3-yl)-(2R)-hydroxyethylamino]methyl}chroman-6-sulfonic acid {4-[4-(3-cyclopentylpropyl)-5-oxo-4,5-dihydrotetrazol-1-yl]phenyl}amide; dihydrochloride | 649 (MH$^+$, electrospray) | |
| 117 | 4-[4-(3-Cyclohexylpropyl)-5-oxo-4,5-dihydrotetrazol-1-yl]-N-{2R-[(2R-hydroxy-2-pyridin-3-ylethylamino)-methyl]chroman-6-yl}benzenesulfon-amide; dihydrochloride | 648 (MH$^+$, electrospray) | |

Example 118 to Example 122 were prepared in analogy to the procedure of Example 44.

| Example | Name | MS | $R_f$ |
|---|---|---|---|
| 118 | (2S)-{[(2R)-2-(6-Amino-pyridin-3-yl)-2-hydroxy-ethylamino]-methyl}-chroman-6-sulfonic acid {4-[4-(3-cyclohexyl-propyl)-5-oxo-4,5-dihydro-tetrazol-1-yl]-phenyl}-amide | 663 (MH$^+$) | 0.1 (B) |
| 119 | 2-{[(2R)-2-(6-Amino-pyridin-3-yl)-2-hydroxy-ethylamino]-methyl}-chroman-6-sulfonic acid {4-[4-(4-cyclopentyl-butyl)-5-oxo-4,5-dihydro-tetrazol-1-yl]-phenyl}-amide | 663 (MH$^+$) | 0.1 (B) |
| 120 | (2S)-{[(2H)-2-(6-Amino-pyridin-3-yl)-2-hydroxy-ethylamino]-methyl}-chroman-6-sulfonic acid {4-[4-(2-bicyclo[2.2.1]hept-2-yl-ethyl)-5-oxo-4,5-dihydro-tetrazot-1-yl]-phenyl}-amide | 661 (MH$^+$) | 0.1 (B) |
| 121 | (2R)-{[(2R)-2-(6-Amino-pyridin-3-yl)-2-hydroxy-ethylamino]-methyl}-chroman-6-sulfonic acid {4-[4-(2-bicycto[2.2.1 ]hept-2-yl-ethyl)-5-oxo-4,5-dihydro-tetrazol-1-yl]-phenyl}-amide | 661 (MH$^+$) | 0.1 (B) |
| 122 | 2S-{[2-(6-Aminopyridin-3-yl)-2H-hydroxyethylamino]methyl}chroman-6-sulfonic acid {4-[4-(3-cyclopentylpropyl)-5-oxo-4, 5-dihydro-tetrazol-1-yl]phenyl}amide | 649 (MH$^+$) | |

Example 123 was prepared in analogy to the procedure of Example 44 and purified by methods described in Example 38 and Example 41.

| Example | Name | MS | $R_f$ |
|---|---|---|---|
| 123 | (2S)-2-{[(2H)-2-(6-Amino-pyridin-3-yl)-2-hydroxy-ethylamino]-methyl}-chroman-6-sulfonic acid {4-[3-(3-cyclohexyl-propyl)-2-oxo-2,3-dihydro-imidazol-1-yl]-phenyl}-amide; hydrate | 661 (MH$^+$) | 0.10 (D) |

EXAMPLE 124

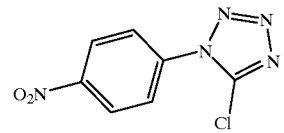

5-Chloro-1-(4-nitro-phenyl)-1H-tetrazole

5-Chloro-1-phenyl-1H-tetrazole (500 g, 2.78 mol) was carefully added in one portion to stirred white fuming nitric acid (91.5% HNO$_3$, 2.5 L). The internal temperature of the mixture increased steadily to 65° C. then fell. An aliquot was removed and partitioned between water and dichloromethane. TLC analysis (80:20 hexanes/ethyl acetate) indicated consumption of starting material. The mixture was carefully poured into stirred ice (3 L), water (2 L) and dichloromethane (2 L). The layers were separated and the aqueous was extracted with dichloromethane (2 L). The combined organic phase was washed with 5% aqueous sodium bicarbonate solution (1 L), dried (MgSO$_4$), filtered, and concentrated to a solid. The solid was mixed with 90:10 hexanes/ethyl acetate (3 L) and heated to 65° C. The mixture was cooled overnight (2–5° C.). Filtration afforded a white crystalline solid (544 g, 87%). $^1$H NMR (CDCl$_3$, 300 MHz) δ 8.51 (d, 9.5 Hz, 2 H), 7.91 (d, 8.8 Hz, 2 H); mp 96.5° C.; R$_f$=0.2 (K).

EXAMPLE 125

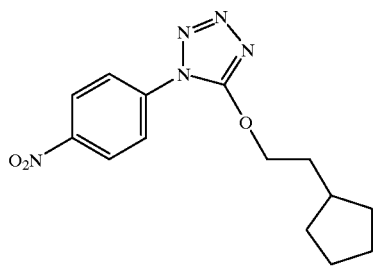

5-(3-Cyclohexyl-propoxy)-1-(4-nitro-phenyl)-1H-tetrazole

Cyclohexylpropyl alcohol (237 mL, 1.56 mol) was added to a suspension of NaH (66.0 g, 1.65 mol) in tetrahydrofuran (1.40 L). A solution of 5-Chloro-1-(4-nitro-phenyl)-1H-tetrazole (320 g, 1.42 mol) in tetrahydrofuran (900 mL) was added dropwise over 1.5 hours. The reaction was allowed to cool to room temperature and stirred overnight. The mixture was concentrated in vacuo to a solid. The solid was dissolved in ethyl acetate, washed with saturated aqueous sodium chloride solution (2×), dried (Na$_2$SO$_4$), and filtered through silica gel (700 g). The red filtrate was concentrated in vacuo until product began to precipitate from solution. Hexane was added and the slurry filtered to provide a tan solid (320 g, 64%). Mp 82–88° C. (dec); $^1$H NMR (CDCl$_3$, 300 MHz) δ 8.43 (d, 9.2 Hz, 2 H), 8.04 (d, 9.2 Hz, 2 H), 4.70 (t, 7.0 Hz, 2 H), 1.96 (m, 2 H), 1.75–1.64 (m, 5 H), 1.39–1.13 (m, 6 H), 0.97–0.87 (m, 2 H); MS (CI) m/z 332 (MH$^+$); Anal. calcd for C$_{16}$H$_{21}$N$_5$O$_3$: C, 57.99; H, 6.39; N, 21.13. Found: C, 57.80; H, 6.35; N, 21.02; R$_f$=0.43 (N).

EXAMPLE 126

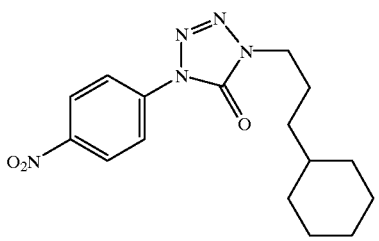

1-(3-Cyclohexyl-propyl)-4-(4-nitro-phenyl)-1,4-dihydro-tetrazol-5-one

Sodium iodide (427 g, 2.85 mol) was added to a solution of 5-(3-cyclohexyl-propoxy)-1-(4-nitro-phenyl)-1H-tetrazole (315 g, 950 mmol) in N,N-dimethylformamide (3.15 L). The mixture was slowly heated with stirring to 108° C. over 2.0 hours. The mixture was allowed to gradually cool to 94° C. over 1.0 hour and was then cooled in an ice bath to between 0 and 5° C. Water (3.25 L) was added dropwise to the vigorously stirred mixture over a period of 2.5 hours. The mixture was stirred overnight at room temperature. Water (1.75 L) was added to the mixture. A fine yellow precipitate was collected by filtration and dried overnight in vacuo at 45° C. to afford a yellow solid (309 g, 98%). Mp 77–82° C.; $^1$H NMR (CDCl$_3$, 300 MHz) δ 8.39 (d, 9.2 Hz, 2 H), 8.28 (d, 9.2 Hz, 2 H), 4.03 (t, 7.4 Hz, 2 H), 1.91 (m, 2 H), 1.73–1.63 (m, 5 H), 1.31–1.11 (m, 6 H), 0.95–0.85 (m, 2 H); MS (CI) m/z 332 (MH$^+$); Anal. calcd for C$_{16}$H$_{21}$N$_5$O$_3$: C, 57.99; H, 6.39; N, 21.13. Found: C, 57.90; H, 6.49; N, 20.97; R$_f$=0.56 (75:25 hexane/ethyl acetate).

EXAMPLE 127

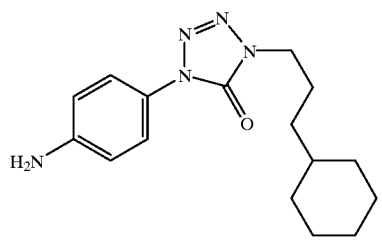

1-(4-Amino-phenyl)-4-(3-cyclohexyl-propyl)-1,4-dihydro-tetrazol-5-one

A solution of 1-(3-cyclohexyl-propyl)-4-(4-nitro-phenyl)-1,4-dihydro-tetrazol-5-one (69.6 g, 210 mmol) in a mixture of absolute ethanol (220 mL) and ethyl acetate (300 mL) was added to a 2 L Parr hydrogenation vessel containing Degussa 10% Pd/C (3.48 g). The Parr vessel was shaken at room temperature under a hydrogen atmosphere maintained at 20 psi for 4.5 hours. The mixture was filtered through Celite and concentrated in vacuo to a light yellow oil which spontaneously crystallized to afford a light brown crystalline solid (63.5 g, 98%). Mp 64–69° C.; $^1$H NMR (CDCl$_3$, 300 MHz) δ 7.64 (d, 8.8 Hz, 2 H), 6.78 (d, 9.2 Hz, 2 H), 3.98 (t, 7.0 Hz, 2 H), 1.88 (m, 2 H), 1.72–1.63 (m, 5 H), 1.29–1.11 (m, 6 H), 0.94–0.84 (m, 2 H); MS (EI) m/z 302.2 (MH$^+$); Anal. calcd for C$_{16}$H$_{23}$N$_5$O: C, 63.76; H, 7.69; N, 23.24. Found: C, 64.00; H, 7.78; N, 22.87; R$_f$=0.67 (B).

EXAMPLE 128

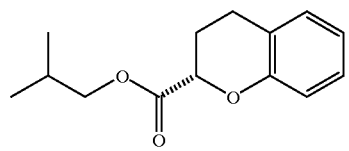

(2S)-Chromancarboxylic acid isobutyl ester

Chroman (S)-2-carboxylic acid (300 g, 1.68 mol), 1-iodo-2-methylpropane (619 g, 3.36 mol) and cesium carbonate (411 g, 1.26 mol) were suspended in dimethylformamide (3.0 L) and heated with stirring for 8 hours. The mixture was poured into water (15 L) and extracted with ethyl acetate (2×3 L). The combined organic extracts were washed with water (2 L) and saturated aqueous sodium chloride solution (2 L), dried (MgSO$_4$), and concentrated in vacuo to afford the product (390 g, 99%). $^1$H NMR (CDCl$_3$, 300 MHz) 7.12 (t, 13.6 Hz, 1 H), 7.06 (d,14.7 Hz, 1 H), 6.98 (d, 21.7 Hz, 1 H), 6.86 (t, 23.5 Hz, 1 H), 4.76 (dd, 7.0 Hz, 4.0 Hz, 1 H), 3.97 (dd, 6.62 Hz, 4.0 Hz, 2 H), 2.89–2.69 (m, 2 H), 2.34–2.15 (m, 2 H), 2.01–1.88 (m, 1 H), 0.90 (d, 6.6 Hz, 6 H); R$_f$=0.6 (4:1 hexane/ethyl acetate).

EXAMPLE 129

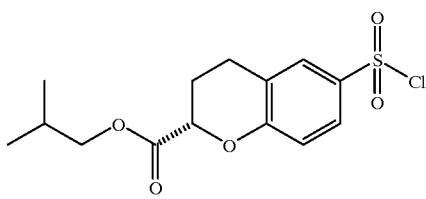

6-Chlorosulfonyl-chroman-(2S)-carboxylic acid isobutyl ester

Chlorosulfonic acid (260 mL, 3.88 mol) in dichloroethane (200 mL) was cooled to −20° C. A solution of (2S)-chroman carboxylic acid isobutyl ester (Example 128; 130 g, 0.56 mol) in dichloroethane (200 mL) was added slowly via an addition funnel so that the internal temperature of the mixture was maintained η0° C. After two hours the mixture was poured over ice and extracted with diethyl ether (4×200 mL). The organic extracts were combined, dried (MgSO$_4$) and concentrated to a dark purple oil. The product was used without additional purification.

EXAMPLE 130

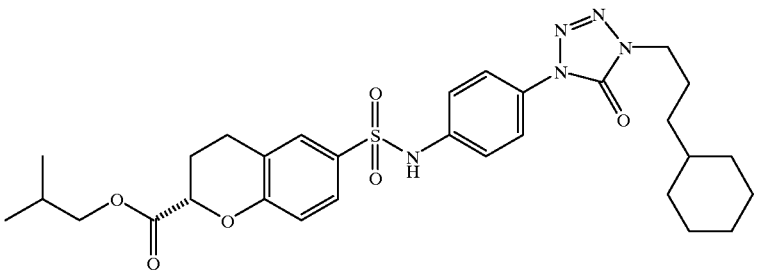

6-{4-[4-(3-Cyclopentyl-propyl)-5-oxo-4,5-dihydro-tetrazol-1-yl]-phenylsulfamoyl}-chroman-(2S)-carboxylic acid isobutyl ester 6-Chlorosulfonyl-chroman-(2S)-carboxylic acid isobutyl ester (Example 129; 81g, 0.24 mol), 4-[4-(3-cyclopentyl-propyl)-5-oxo-4,5-dihydro-tetrazol-1-yl]-phenylamine (prepared in analogy to Example 127; 66.5 9, 0.23 mol), pyridine (57 g, 0.72 mol) and 4-dimethylaminopyridine (1.0 g) were dissolved in tetrahydrofuran and heated to 600 for 16 hours. The mixture was cooled to room temperature and concentrated. The mixture was partitioned between ethyl acetate (700 mL) and 1N hydrochloric acid (250 mL). The organic phase was washed with 1N hydrochloric acid (250 mL), saturated sodium bicarbonate solution (250 mL), and saturated aqueous sodium chloride solution (250 mL), dried (MgSO$_4$), and concentrated to a solid. The solid was dissolved in dichloromethane (100 mL) and chromatographed (12 micron spherical silica gel; 3:1 hexane/ethyl acetate, 400 mL/min) to afford a colorless solid (97 g, 71%). mp 102° C.; $^1$H NMR (CDCl$_3$, 300 MHz) 7.82 (m, 2 H), 7.53 (m, 2 H), 7.20 (m, 2 H), 7.05 (s, 1 H), 6.92 (d, 8.8 Hz, 1 H), 4.81 (t, 10.0 Hz, 1 H), 4.01–3.90 (m, 4 H), 2.82–2.65 (m, 2 H), 2.26–2.19 (m, 2 H), 1.94–1.82 (m, 3 H), 1.79–1.69 (m, 3 H), 1.62–1.46 (m, 5 H), 1.41–1.3 (m, 2 H), 1.11–1.02 (m, 2 H), 0.85 (d, 6.6 Hz, 6 H); R$_f$=0.2 (N).

Example 131 through Example 136 were prepared by the method described in Example 130.

| Example | Name | MS | R$_f$ |
|---|---|---|---|
| 131 | (H)-6-Hexylsulfamoyl-chroman-2-carboxylic acid isobutyl ester | 397 (M$^+$) | 0.2 (M) |
| 132 | (H)-6-(4-Phenyl-piperazine-1-sulfonyl)-chroman-2-carboxylic acid isobutyl ester | 459 (MH$^+$) | 0.2 (M) |
| 133 | (H)-6-(3-butoxy-propylsulfamoyl)-chroman-2-carboxylic acid isobutyl ester | 428 (MH$^+$) | 0.15 (M) |
| 134 | (H)-6-Cyclohexylsulfamoyl-chroman-2-carboxylic acid isobutyl ester | 396 (MH$^+$; HPLC/MS) | 0.25 (N) |
| 135 | (H)-6-(Dibenzofuran-2-ylsulfamoyl)-chroman-2-carboxylic acid isobutyl ester | 450 (MH$^+$, HPLC/MS) | 0.19 (N) |
| 136 | (R)-6-[(Furan-2-ylmethyl)-sulfamoyl]-chroman-2-carboxylic acid isobutyl ester | 394 MH$^+$, electrospray) | 0.19 (N) |

EXAMPLE 137

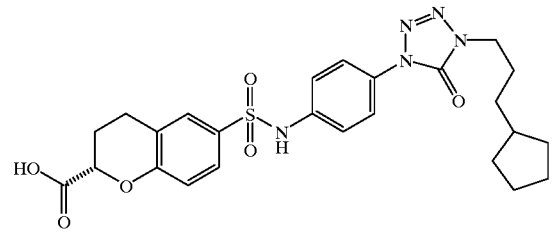

6-{4-[4-(3-Cyclopentyl-propyl)-5-oxo-4,5-dihydro-tetrazol-1-yl]-phenylsulfamoyl}-chroman-(S)-2-carboxylic acid 6-{4-[4-(3-Cyclopentyl-propyl)-5-oxo-4,5-dihydro-tetrazol-1-yl]-phenylsulfamoyl}-chroman-(2S)-carboxylic acid isobutyl ester (Example 130, 96 g, 0.164 mol) was added to 25% aqueous sodium hydroxide (66 mL, 412 mmol) and methanol (480 mL). The mixture was stirred at room temperature for 45 minutes. 1 N hydrochloric acid (425 ml, 0.425 mol) was added until the pH of the mixture was 3. The mixture was extracted with CH$_2$Cl$_2$ (3×1 L). The organic phase was washed with water and brine, dried (Na$_2$SO$_4$) and concentrated to give a solid. In order to remove residual isobutyl alcohol, cyclohexane was added and the mixture concentrated by rotary evaporation. The residue was washed with ether to obtain a slight yellow solid (87.6 g, 100% yield). $^1$H NMR (300 MHz, CDCl$_3$), δ 7.74(d, 8.8 Hz, 2 H), 7.52 (dd, 2.4 Hz, 8.5 Hz, 1 H), 7.47 (br s, 1 H), 7.34 (s, 1 H), 7.16 (d, 8.8 Hz, 2 H), 6.89 (d, 8.5 Hz, 1 H), 5.38 (br s, 1 H), 4.19 (dd, 4.5 Hz, 6 Hz, 1 H), 3.97 (t, 7.2 Hz, 2 H), 2.60–2.83 (m, 2 H), 2.14–2.32 (m, 2 H), 2.66–192 (m, 5 H), 1.30–1.54 (m, 6 H), 0.95–1.13(m, 2 H); LC/MS (ES) m/z 528 (MH$^+$); Anal. calcd. for $C_{25}H_{29}N_5O_6S$: C, 56.91; H, 5.54; N, 13.27; S, 6.08. Found: C, 57.27; H, 5.47; N, 13.42; S, 6.25.

EXAMPLE 138

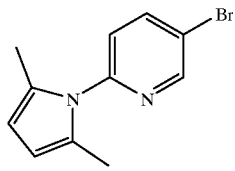

5-Bromo-2-(2,5-dimethyl-pyrrol-1-yl)-pyridine

Hexane-2,5-dione (97 mL, 831 mmol) was added to a solution of 2-amino-5-bromo-pyridine (125 g, 722 mmol) in cyclohexane (625 mL) and acetic acid (20 mL). The solution was heated to reflux under argon atmosphere with a Dean-Stark trap. A total of 30 mL of water was collected from the Dean-Stark trap. The mixture was allowed to cool to room temperature, diluted with water, and extracted with diethyl ether. The organic phase was washed with 1N hydrochloric acid (4×), saturated aqueous sodium bicarbonate solution (2×) and saturated aqueous sodium chloride solution (2×). The organic phase was dried (MgSO$_4$) and concentrated in vacuo to yield a yellow solid. The product was dissolved in hot hexanes (200 mL). Charcoal was added and the mixture filtered. Crystallization proceeded over three hours at 0° C. The solid was collected by filtration to yield yellow crystals (145 g, 80%). Mp=69° C.; $^1$H NMR (CDCl$_3$, 300 MHz) δ 8.66 (d, 9 Hz, 1 H), 7.96 (dd, 9 Hz, 8 Hz, 1 H), 7.15 (d, 8 Hz, 1 H), 5.91 (s, 2 H), 2.14 (s, 6 H); MS (CI) m/z 251 (MH$^+$); Anal. Calcd. for $C_{11}H_{11}BrN_2$: C, 52.61; H, 4.42; N, 11.16; Br, 31.82. Found: C, 52.62; H, 4.56; N, 11.18; R$_f$=0.4 (60:40 dichloromethane/hexanes).

EXAMPLE 139

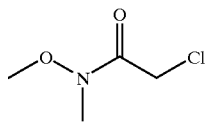

N-methoxy-N-methylchloroacetamide

A solution of N,O-dimethylhydroxylamine hydrochloride (200 g, 2.05 mol) and tert-butyl methyl ether (2 L) was added to a cooled (0° C.) solution of potassium carbonate (624 g, 4.1 mol) in water (2 L). The mixture was cooled to −5° C. and chloroacetyl chloride added such that the temperature remained below 5° C. The vigorously stirred mixture was allowed to warm to room temperature and stirred for an additional 3.5 hours. The phases were separated and the aqueous phase was extracted with tert-butyl methyl ether (3×1 L). The combined organic phase was washed with saturated aqueous sodium chloride solution (2×1 L), dried (MgSO$_4$), and concentrated. The residue was dried in vacuo to yield a white solid (257 g, 92%). Mp 39–40.5° C.; $^1$H NMR (CDCl$_3$, 300 MHz) δ 4.24 (s, 2 H), 3.74 (s, 3 H), 3.22 (s, 3 H); MS (CI) 138 (MH$^+$); Anal. calcd for $C_4H_8ClNO_2$: C, 34.92; H, 5.86; N, 10.18. Found: C, 35.06; H, 5.88; N, 10.23.

EXAMPLE 140

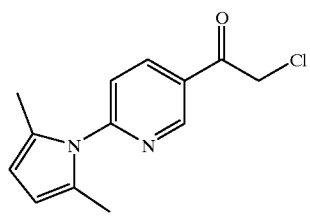

2-Chloro-1-[6-(2,5-dimethyl-pyrrol-1-yl)-pyridin-3-yl]-ethanone

Magnesium turnings (7.26 g, 0.30 mol) were placed in 2 L three neck flask equipped with a dropping funnel and reflux condenser. The system was purged with argon and heated for ten minutes. After cooling the flask to room temperature under argon, tetrahydrofuran (500 mL) and a crystal of iodine were added. A portion of a solution of 5-bromo-2-(2,5-dimethyl-pyrrol-1-yl)-pyridine (Example 138; 75 g, 0.30 mol) in tetrahydrofuran (200 mL) was added to initiate the reaction. The flask was heated to maintain reflux as the remainder of the solution was added. After three hours the mixture was cooled in an ice-water bath. A solution of N-methoxy-N-methylchloroacetamide (Example 139; 49.3 g, 0.35 mol) in tetrahydrofuran (200 mL) was transferred to the suspension via cannula. The mixture was warmed to ambient temperature. After 18 hours the mixture was quenched with two-thirds saturated aqueous ammonium chloride solution and extracted with ethyl acetate (3×). The combined organic phase was dried (MgSO$_4$) and concentrated to an oil. Silica gel chromatography (75:25 hexane/ethyl acetate) afforded an oil (67 g). The oil was a 7:3 mixture of the title compound and 2-(2,5-dimethyl-pyrrol-1-yl)-pyridine. $^1$H NMR (CDCl$_3$, 300 MHz; peaks corresponding to the title compound) δ 9.16 (dd, 2.6 Hz, 0.7 Hz, 1 H), 8.40 (dd, 8.5 Hz, 2.6 Hz, 1 H), 7.35 (dd, 8.5 Hz, 0.7 Hz, 1 H), 5.96 (s, 2 H), 4.71 (s, 2 H), 2.21 (s, 6 H); R$_f$=0.2 (5:1 hexane/ethyl acetate).

EXAMPLE 141

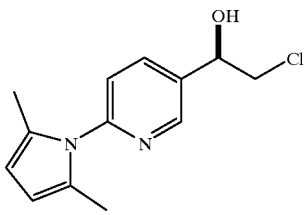

(1R)-2-Chloro-1-[6-(2.5-dimethyl-pyrrol-1-yl)-pyridin-3-yl]-ethanol (R)-Alpine borane (1.5 L, 0.5 M in tetrahydrofuran) was added slowly to a cooled (0° C.), neat, 2-chloro-1-[6-(2,5-dimethyl-pyrrol-1-yl)-pyridin-3-yl]-ethanone (Example 140; 93 g). The mixture was warmed to room temperature and reduced to one third its original volume by distilling tetrahydrofuran. After four days, the mixture was cooled to 0° C. and 3 M aqueous solution of K$_2$CO$_3$ (600 mL) was added. Then the reaction mixture was oxidized by drop wise addition of 30% H$_2$O$_2$ (250 mL). After stirring at room temperature for 3 h, the reaction mixture was diluted ethyl acetate, organic layer was separated. Aqueous portion was extracted (ethyl acetate), combined organic extracts were washed with water and dried. After concentration in vacuo, the resulting oil was purified by chromatography on silica gel (hexanes/ethyl acetate as eluent) to afford a yellow solid (35 g). $^1$H NMR (CDCl$_3$, 300 MHz) δ 8.59 (m, 1 H), 7.88 (dd, 8.1 Hz, 2.2 Hz, 1 H), 7.26 (m, 1 H), 5.91 (m, 2 H), 4.96 (m, 1 H), 3.78 (m, 2 H), 3.35 (br s, 1 H), 2.11 (2, 6 H); MS (FAB) m/z 251 (MH$^+$); Anal. calcd for C$_{13}$H$_{15}$N$_2$OCl: C, 62.28; H, 6.03; N, 11.17. Found: C, 61.95; H, 6.03; N, 10.92; R$_f$=0.4 (60:40 hexanes/ethyl acetate).

EXAMPLE 142

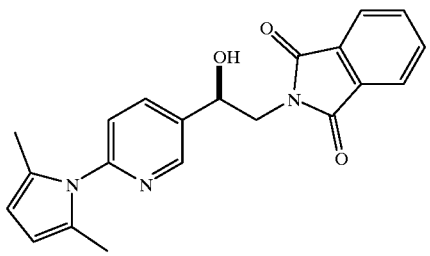

(R)-2-{2-[6-(2,5-Dimethylpyrrol-1-yl)pyridin-3-yl]-2-hydroxyethyl}isoindol-1,3-dione A mixture of (2R)-2-chloro-1-[6-(2,5-dimethyl-pyrrol-1-yl)-pyridin-3-yl]-ethanol (Example 141; 33.45 g, 133.41 mmol) and potassium phthalimide (24.12 g, 130.22 mmol) was dried in vacuo for 3 hours. Anhydrous N,N-dimethylformamide (250 mL) was added and the mixture was heated to 80° C. for 45 hours. The mixture was cooled to room temperature and poured into ethyl acetate (800 mL). The organic phase was washed with saturated aqueous sodium chloride solution (4×2 L), dried (Na$_2$SO$_4$), and concentrated to a volume of approximately 50 mL, producing a precipitate. The mixture was filtered, and the precipitate washed with hexanes (50 mL) and dried under vacuum to afford a tan solid (35.21 g, 75%). Mp 167–170° C.; $^1$H NMR (DMSO-d$_6$, 300 MHz): δ 1.98 (s, 6 H), 3.74 (dd, 5.9 Hz, 13.6 Hz, 1 H), 3.88 (dd, 7.7 Hz, 13.6 Hz, 1 H), 5.01 (m, 1 H), 5.77 (s, 2 H), 5.96 (d, 4.4 Hz, 1 H), 7.34 (d, 8.4 Hz, 1 H), 7.83 (m, 4 H), 7.93 (dd, 2.2 Hz, 8.4 Hz, 1 H), 8.47 (d, 2.2 Hz, 1 H); MS (EI) m/z 362 (MH$^+$); Anal. Calcd for C$_{21}$H$_{19}$N$_3$O$_3$.0.15 H$_2$O: C, 69.27; H, 5.34; N, 11.54. Found: C, 69.07; H, 5.11; N, 11.51; R$_f$=0.37 (60:40 hexanes/ethyl acetate).

EXAMPLE 143

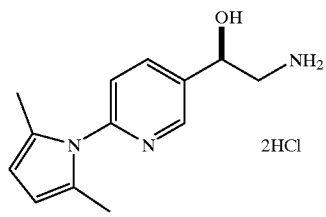

(R)-2-Amino-1-[6-(2,5-dimethylpyrrol-1-yl)pyridin-3-yl]ethanol dihydrochloride

A refluxing solution of (R)-2-{2-[6-(2,5-dimethylpyrrol-1-yl)pyridin-3-yl]-2-hydroxyethyl}isoindol-1,3-dione (Example 142; 65.6 g, 182 mmol) in ethanol (1.3 L) was treated with hydrazine monohydrate (9.80 g, 196 mmol). After three hours the mixture was cooled to 5° C. Concentrated hydrochloric acid (80 mL) was slowly added at a rate which maintained the internal temperature below 10° C. The mixture was heated to reflux for 20 minutes, cooled to room temperature, and filtered. The filtrate was concentrated under vacuum at 30° C. and the material was dried under high vacuum at 35° C. for 16 hours to provide a yellow solid (59.3 g,>100%). A small sample was free-based with 1.0 N sodium hydroxide, extracted into dichloromethane and converted to the dihydrochloride salt with ethereal HCl. Mp>250° C.; $^1$H NMR (DMSO-d$_6$, 300 MHz); δ 2.03 (s, 6 H), 3.02 (m, 1 H), 3.16 (m, 1 H), 5.02 (m, 1 H), 5.79 (s, 2 H), 7.43 (d, 8.1 Hz, 1 H), 8.01 (dd, 2.2 Hz, 8.1 Hz, 1 H), 8.27 (br s, 3 H), 8.59 (d, 2.2 Hz, 1 H); MS (ES) m/z 232 (MH$^+$); Anal. Calcd for C$_{13}$H$_{19}$N$_3$O.2 HCl.0.20 H$_2$O: C, 50.72; H, 6.35; N, 13.65; Cl, 23.03. Found: C, 50.55; H, 6.19; N, 13.43; Cl, 23.23.

EXAMPLE 144

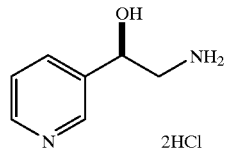

(R)-2-Amino-1-pyridin-3-yl-ethanol dihydrochloride

The title compound was prepared from (R)-chloromethyl-3-pyridinemethanol (Example 6) according to the procedures described in Examples 142 and 143.

EXAMPLE 145

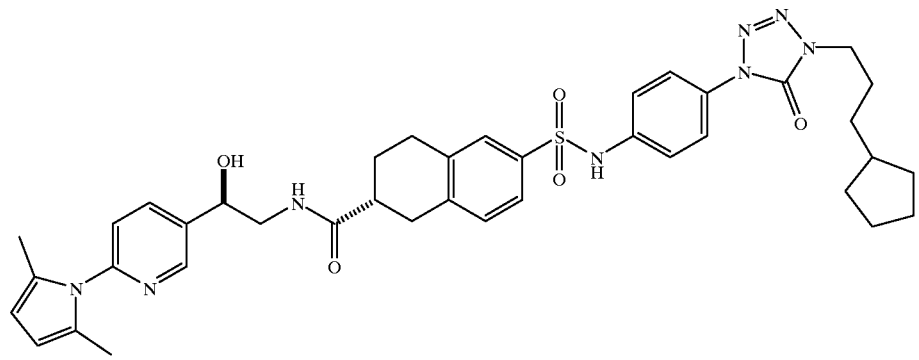

6-{4-[4-(3-cyclopentyl-propyl)-5-oxo-4,5-dihydro-tetrazol-1-yl]-phenylsulfamoyl}-chroman-(2S)-2-carboxylic acid {2-[6-(2,5-dimethyl-pyrrol-1-yl)-pyridin-3-yl]-(2R)-2-hydroxy-ethyl }-amide To a stirred mixture of 6-{4-[4-(3-cyclopentyl-propyl)-5-oxo-4,5-dihydro-tetrazol-1-yl]-phenylsulfamoyl}-chroman-(2S)-2-carboxylic acid (Example 137; 69 g, 0.13 mol) and (R)-2-Amino-1-[6-(2,5-dimethylpyrrol-1-yl)pyridin-3-yl] ethanol dihydrochloride (Example 143; 43.81 g, 0.144 mol) in dichloromethane (690 mL) was added 1-hydroxybenzotriazole (35.13 g, 0.26 mol), N-ethyl N'-dimethylaminopropylcarbodiimide (49.84 g, 0.26 mol), and triethylamine (55 mL, 0.39 mol). After stirring overnight the mixture was washed with water (1.4 L). The aqueous phase was extracted with dichloromethane (2×). The combined organic phase was washed with saturated aqueous sodium chloride solution (500 mL), dried ($Na_2SO_4$) and concentrated to a stiff gum. The gum was dissolved in dichloromethane and filtered through a pad of silica gel (1 kg); elution with dichloromethane and then with a gradient (0.5–2% methanol/dichloromethane) afforded a beige foam (78.0 g, 81%). $^1H$ NMR (DMSO-$d_6$, 500 MHz) δ 10.41 (s, 1 H), 8.46 (d, 2.4 Hz, 1 H), 8.02 (dd, 5.8 Hz, 6.0 Hz, 1 H), 7.79 (dd, 8.2 Hz, 2.4 Hz, 1 H), 7.67 (d, 9.0 Hz, 1 H), 7.51–2 (2 H), 7.27 (d, 8.2 Hz, 1 H), 7.26 (d, 8.9 Hz, 1 H), 6.95 (d, 9.3 Hz, 1 H), 5.76 (s, 2 H), 4.8 (m, 1 H), 4.6 (dd, 8.4 Hz, 3.4 Hz, 1 H), 3.92 (t, 7.0 Hz, 2 H), 3.4 (m, 2 H), 2.75 (m, 1 H), 2.56 (m, 1 H), 1.99 (m, 1 H), 1.81 (m, 1 H), 1.78 (m, 3 H), 1.73 (m, 2 H), 1.53 (m, 2 H), 1.48 (m, 2 H), 1.29 (m, 2 H), 1.03 (m, 2 H); HPLC MS (ES) m/z 740; Anal. calcd. for $C_{38}H_{44}N_8O_6S+0.5\ H_2O$: C, 60.87; H, 6.05; N, 14.94; O, 13.87; S, 4.28. Found: C, 60.63; H, 5.9; N, 14.9; S, 4.4; $R_f$=0.25 (10% methanol/dichloromethane); $R_f$=0.46 (ethyl acetate).

EXAMPLE 146

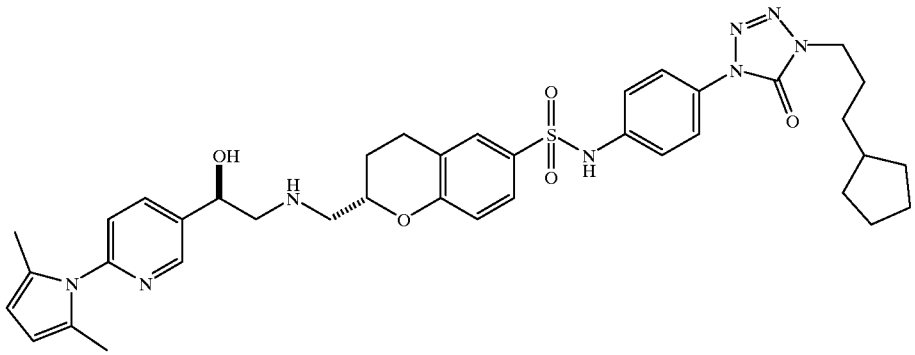

6-{4-[-(3-Cyclopentyl-propyl)-5-oxo-4,5-dihydro-tetrazol-1-yl]-phenylsulfamoyl}-chroman-(2S)-2-carboxylic acid {2-[6-(2,5-dimethyl-pyrrol-1-yl)-pyridin-3-yl]-(2R)-2-hydroxy-ethylamino}-amide Borane dimethylsulfide complex in tetrahydrofuran (2 N, 325 mL, 0.65 mol) was added carefully in one portion to a solution of 6-{4-[4-(3-cyclopentyl-propyl)-5-oxo-4,5-dihydro-tetrazol-1-yl]-phenylsulfamoyl}-choman-(2S)-2-carboxylic acid {2-[6-(2,5-dimethyl-pyrrol-1-yl)-pyridin-3-yl]-(2R)-2-hydroxy-ethyl}-amide (Example 145; 80 g, 0.11 mol) in tetrahydrofuran (325 mL). The mixture was heated to reflux (64° C.) for 2 hours, then cooled to <5° C. Methanol (25 mL) was added slowly to destroy excess borane. Hydrochloric acid (6N, 125 mL) and hydroxylamine hydrochloride (37 g, 0.54 mol) were added and the solution was returned to reflux for 1 hour. After cooling to 5° C., the pH of the solution was adjusted to 7 with 2 N sodium hydroxide. Methanol and tetrahydrofuran were removed under reduced pressure. Water (200 mL) was added and the pH adjusted to 10. The aqueous phase was extracted with ethyl acetate (3×400 mL), washed with saturated aqueous sodium chloride solution, dried ($MgSO_4$), and concentrated in vacuo to a white foam (75 g, 95%). $^1H$ NMR ($CDCl_3$, 300 MHz) δ 10.32 (m, 1 H), 8.55 (s, 1 H), 7.89 (dd, 8.3 Hz, 2.2 Hz, 1 H), 7.79 (d,1.83 Hz, 1 H), 7.64 (d, 8.9 Hz, 5 H), 7.51–7.42 (m, 5 H), 7.31–7.20 (m, 7 H), 6.80 (d, 8.8 Hz, 2 H), 6.35 (d, 8.8 Hz, 1 H), 5.73 (d, 5,9 Hz, 4 H), 4.76–4.72 (m, 1 H), 4.46–4.37 (m, 2 H), 4.15–4.08 (m, 2 H), 3.09 (t, 14 Hz, 1 H), 3.38–3.33 (m, 2 H), 2.77–2.72 (m, 2 H), 1.77–1.69(m, 3 H), 1.55–1.45 (m, 2 H), 1.38–1.26 (m, 2 H), 1.08–0.94 (m, 1 H); MS (FAB) m/z 728 (MH⁺); $R_f$=0.6 (B).

Example 147 through Example 153 were prepared by the methods described in Example 137, Example 145, and Example 146.

| Example | Name | MS | $R_f$ |
|---|---|---|---|
| 147 | (2R)-2-[(2R)-(2-Hydroxy-2-pyridin-3-yl-ethylamino)-methyl]-chroman-6-sulfonic acid hexylamide | 509 (MH⁺) | 0.15 (J) |
| 148 | (2R)-2-{[6-(4-Phenyl-piperazine-1-sulfonyl)-chroman-(2R)-2-ylmethyl]-amino}-1-pyridin-3-yl-ethanol | 448 (MH⁺) | 0.1 (L) |
| 149 | (2R)-2-[(2R)-(2-Hydroxy-2-pyridin-3-yl-ethylamino)-methyl]-chroman-6-sulfonic acid (3-butoxy-propyl)-amide | 478 (MH⁺) | 0.4 (J) |
| 150 | (2R)-2-[((2R)-2-Hydroxy-2-pyridin-3-yl-ethylamino)-methyl]-chroman-6-sulfonic acid {4-[4-(3-cyclohexyl-propyl)-5-oxo-4,5-dihydro- | 648 (MH⁺) | 0.2 (C) |

-continued

| Example | Name | MS | $R_f$ |
|---|---|---|---|
| | tetrazol-1-yl]-phenyl}-amide | | |
| 151 | (2R)-2-[(2R)-(2-Hydroxy-2-pyridin-3-yl-ethylamino)-methyl]-chroman-6-sulfonic acid cyclohexylamide | 446 (MH⁺, electrospray, HPLC/MS) | 0.40 (J) |
| 152 | (2R)-2-[(2R)-(2-Hydroxy-2-pyridin-3-yl-ethylamino)-methyl]-chroman-6-sulfonic acid dibenzofuran-2-ylamide | 530 (MH⁺, electrospray, HPLC/MS) | 0.40 (J) |
| 153 | (2R)-2-[(2R)-(2-Hydroxy-2-pyridin-3-yl-ethylamino)-methyl]-chroman-6-sulfonic acid (furan-2-ylmethyl)-amide | 444 (MH⁺, electrospray, HPLC/MS) | 0.40 (J) |

EXAMPLE 154

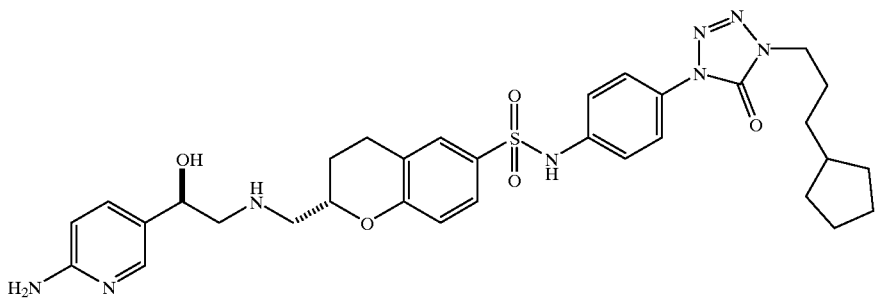

(2S)-2-{[(2R)-2-(6-Amino-pyridin-3-yl)-2-hydroxy-ethylamino]-methyl}-chroman-6-sulfonic acid {4-[3-cyclopentyl-propyl)-5-oxo-4,5-dihydro-tetrazol-1-yl]-phenyl}-amide 6-{4-[-(3-Cyclopentyl-propyl)-5-oxo-4,5-dihydro-tetrazol-1-yl]-phenylsulfamoyl}- chroman-(2S)-2-carboxylic acid {2-[6-(2,5-dimethyl-pyrrol-1-yl)-pyridin-3-yl]-(2R)-2-hydroxy-ethylamino}-amide (Example 146; 75 g, 0.103 mol) was combined with hydroxylamine hydrochloride (52.2 g, 0.75 mol) in water (325 mL) and ethanol (400 mL) and heated to reflux for 12 hours. The solution was cooled, diluted with ethyl acetate (250 mL), and the pH adjusted to 10 with 2N sodium hydroxide. After extraction the aqueous phase was further extracted ethyl acetate (2×250 mL). The combined organic phase was washed with saturated aqueous sodium chloride (200 mL), dried (MgSO$_4$), and concentrated to a solid. The solid was dissolved in ethyl acetate (100 mL) and chromatographed (8 micron spherical silica gel, 5:1 ethyl acetate/methanol, 225 mL/min) to afford a colorless solid (38.5 g, 58%). mp 99.3–99.7° C.; $^1$H NMR (DMSO-d$_6$, 300 MHz) δ 7.81 (s, 1 H), 7.67 (d, 8.8 Hz, 2 H), 7.53 (s, 1 H), 7.46 (dd, 8.8 Hz, 2.5 Hz, 1 H), 7.31 (dd, 8.4 Hz, 2.2 Hz, 1 H), 7.24 (d, 8.9 Hz, 1 H), 6.83 (d, 8.8 Hz, 1 H), 6.37 (d, 8.0 Hz, 1 H), 5.75 (s, 2 H), 5.12–5.05 (m, 1 H), 4.47–4.43 (m, 1 H), 4.18–4.11 (m, 1 H), 3.92 (t, 14 Hz, 2 H), 2.84–2.58 (m, 6 H), 2.00–1.96 (m, 1 H), 1.79–1.46 (m, 6 H), 1.56–1.42 (m, 5 H), 1.33–1.26 (m, 2 H), 1.04–0.99 (m, 2 H). MS (FAB) m/z 649 (MH$^+$). Anal. Calcd. for: C$_{32}$H$_{40}$N$_8$O$_5$S: C, 59.24; H, 6.21; N, 17.27; S, 4.94. Found: C, 58.72; H, 6.20; N, 16.98; S, 4.79; R$_f$=0.4 (1:1 ethyl acetate/methanol); [α]$_D^{25}$ +37.8 (c=0.01 in ethanol).

EXAMPLE 155

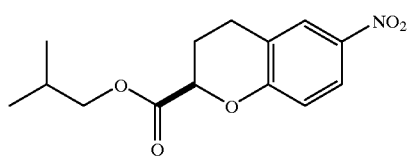

Isopropyl (R)-6-nitro-chroman-2-carboxylate

Isopropyl (R)-6-nitro-chroman-2-carboxylate (40.0 g, 170 mmol) was added over several minutes to cooled (0° C.) nitric acid (400 mL). The internal temperature of the mixture was η5° C. throughout the addition. After four hours the mixture was poured into ice water (1.4 L) and extracted with ethyl acetate (3×350 mL). The combined organic phase was washed with water (2×350 mL), dried (MgSO$_4$), and concentrated to a brown oil. Diethyl ether (250 mL) was added and the solution concentrated by rotary evaporation. The residue was mixed with isopropyl alcohol (65 mL) producing a precipitate. The mixture was heated in an oil bath at 65° C. until all the solids had dissolved. The solution was cooled to –17° C. for three hours. The resultant crystals were filtered, washed with cold isopropyl alcohol (2×65 mL), and dried in vacuo to give a beige solid (21.2 g, 45%). mp 87–88° C.; $^1$H NMR (CDCl$_3$, 300 MHz) δ 8.01 (m, 2 H), 7.01 (d, 8.8 Hz, 1 H), 4.91 (d, 5.0 Hz, 1 H), 3.98 (d, 6.6 Hz, 2 H), 2.88 (m, 2 H), 2.30 (m, 2 H), 1.94 (sept, 6.7 Hz, 1 H), 0.90 (d, 7.0 Hz, 6 H); MS (CI) m/z 280 (MH$^+$); R$_f$=0.61 (67:33 hexane/ethyl acetate).

The enantiomeric purity was determined by HPLC as follows. A Rainin HPLC system was equipped with an R,R Whelk-O1 column (4.6×500 mm). The system was equilibrated with a mobile phase consisting of 10% isopropyl alcohol and 90% hexane at a flow rate of 0.7 mL/min. The effluent was monitored at 280 nm. Under these conditions, the desired R enantiomer eluted at 32.0 minutes and the undesired S enantiomer eluted at 38.1 minutes. The ratio of enantiomers was 98:2.

EXAMPLE 156

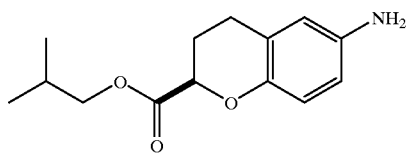

Isopropyl (R)-6-amino-chroman-2-carboxylate

To an argon flushed 2.5 L Parr bottle was added 10% Pd on carbon (3.40 g), ethyl acetate (1.2 L), and isopropyl (R)-6-amino-chroman-2-carboxylate (84.4 g, 303 mmol). The mixture was placed under 20 psig H$_2$ on a Parr apparatus. After 1.5 hours the H$_2$ was replaced with argon. The mixture filtered through Celite and the filtrate concentrated to a light pink solid (74.5 g, 99%). Mp 65–66° C.; $^1$H NMR (C$_6$D$_6$, 300 MHz) δ 6.93 (d, 8.4 Hz, 1 H), 6.18 (dd, 8.5 Hz, 3.0 Hz, 1 H), 5.96 (d, 2.9 Hz, 1 H), 4.49 (dd, 7.0 Hz, 3.7 Hz, 1 H), 3.78 (m, 2 H), 2.37 (m, 2 H), 1.98 (m, 1 H), 1.89 (m, 1 H), 1.66 (m, 1 H), 0.66 (dd, 6.6 Hz, 1.1 Hz, 6 H); MS (ES) m/z 250 (MH$^+$); R$_f$=0.07 (m).

The enantiomeric purity was determined by HPLC as follows. A Rainin HPLC system was equipped with a Chiralpak AS column (4.6×250 mm). The system was equilibrated with a mobile phase consisting of 20.5% isopropyl alcohol and 79.5% hexane at a flow rate of 1.0 mL/min. The sample was dissolved in ethanol (1 mg/mL) and 10 mL sample was injected into the system. The effluent was monitored at 298 nm. Under these conditions, the two enantiomers eluted at 10.1 min and 14.6 min. The ratio of enantiomers was 97:3.

EXAMPLE 157

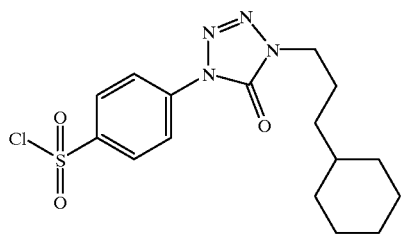

4-[4-(3-Cyclohexyl-propyl)-5-oxo-4,5-dihydro-tetrazol-1-yl]-benzenesulfonyl chloride A stirred mixture of concentrated aqueous hydrochloric acid (450 mL) and glacial acetic acid (107 mL) was cooled below −20° C., and the intermediate from Example 127 (82.7 g, 0.27 mol) was added all at once. A solution of sodium nitrite (24.4 g, 0.34 mol) in water (150 mL) was added dropwise, maintaining pot temperature below −16° C. The resulting mixture was stirred at between −20° C. and −26° C. Meanwhile, a stirred suspension of copper (I) chloride (10.5 g, 0.1 mol) in glacial acetic acid (420 mL) and water (30 mL) was cooled in ice water while sulfur dioxide gas was bubbled in at a moderate rate. After 45 minutes the diazotization mixture was poured into the vigorously stirred suspension via a long-stemmed funnel producing a vigorous gas evolution. After 30 minutes the ice water bath was removed. After one hour the mixture was poured into vigorously stirred water (10 L). The precipitated solid was filtered and washed with water (1 L). The solid was dissolved in dichloromethane and washed with saturated aqueous sodium chloride solution. The aqueous phase was extracted with hexanes (2×). The combined organic phases were diluted with hexanes to make a 2:1 hexanes/dichloromethane mixture. The mixture was dried ($Na_2SO_4$) and filtered through silica gel (875 g). Elution with 50:50 followed by 33:67 hexanes/dichloromethane afforded a nearly colorless solid (62.3 g, 60%). Recrystallization of a sample from dichloromethane/hexanes afforded a colorless solid. Mp 113.5–115° C.; $^1$H NMR ($CDCl_3$, 300 MHz) δ 8.36 (d, 8.8 Hz, 2 H), 8.18 (d, 8.8 Hz, 2 H), 4.0 (t, 7.3 Hz, 2 H), 1.91 (m, 2 H), 1.69 (m, 5 H), 1.28 (m, 6 H), 0.91 (m, 2 H); MS (CI) m/z 385 (MH$^+$); Anal. calcd. for $C_{16}H_{21}ClN_4O_3S$: C, 49.93; H, 5.5; Cl, 9.21; N, 14.56; O, 12.47; S, 8.33. Found: C, 50.11; H, 5.69; Cl, 9.02; N, 14.73; S. 8.32; $R_f$=0.42 (80:20 hexanes/ethyl acetate); $R_f$=0.23 (50:50 hexanes/dichloromethane).

EXAMPLE 158

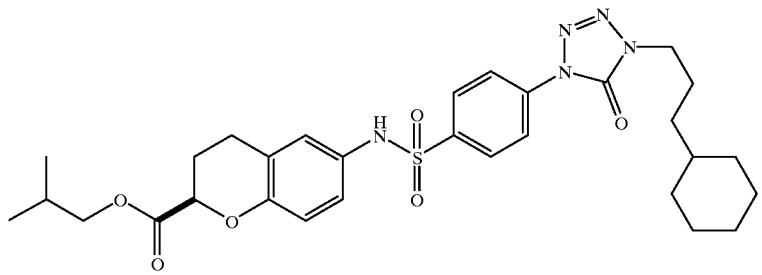

(2R)-6-{4-[4-(3-Cyclohexylpropyl)-5-oxo-4,5-dihydrotetrazol-1-yl]-benzenesulfonylamino}-chroman-carboxylic acid isobutyl ester Pyridine (33 mL, 403 mmol) and N,N-dimethylaminopyridine (100 mg) were added to a solution of isopropyl (R)-6-amino-chroman-2-carboxylate (Example 156; 40 g, 161 mmol) and 4-[4-(3-cyclohexyl-propyl)-5-oxo-4,5-dihydro-tetrazol-1-yl]-benzenesulfonyl chloride (Example 157; 62 g, 161 mmol) in tetrahydrofuran (1 L). The reaction mixture was heated to reflux for 12 hours. The mixture was cooled to room temperature and water (200 mL) and ethyl acetate (500 mL) were added. The organic phase was washed with 1 N HCl (3×) followed by brine. The organic phase was dried (sodium sulfate) and concentrated in vacuo. The crude product was chromatographed through a short pad of silica gel (50:50 ethyl acetate/hexane). The resulting solid was mixed with hexane/diethyl ether (90:10) and the mixture filtered to afford a light yellow solid (87 g, 90%). $^1$H NMR ($CDCl_3$, 300 MHz) δ 8.12 (d, 8.8 Hz, 2 H), 7.80 (d, 8.8 Hz, 2 H), 6.84 (d, 2.6 Hz, 1 H), 6.74 (m, 1 H), 6.66 (m, 1 H), 6.24 (s, 1 H), 4.71 (m, 1 H), 4.0–3.9 (m, 4 H), 2.69 (m, 2 H), 2.18 (m, 2 H), 1.88 (m, 3 H), 1.66 (m, 5 H), 1.22 (m, 6 H), 0.86 (m, 7.0 Hz, 8 H); MS (FAB) m/z 598 (MH$^+$); $R_f$=0.76 (C).

EXAMPLE 159

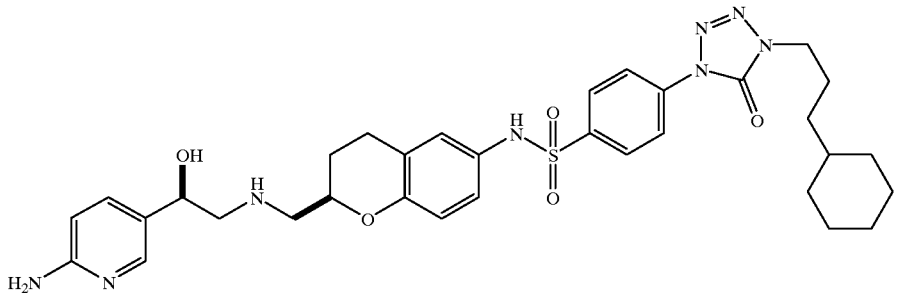

N-((2R)-2-{[(2R)-2-(6-Amino-pyridin-3-yl)-2-hydroxy-ethylamino]-methyl}-chroman-6-yl)-4-[4-(3-cyclohexyl-propyl)-5-oxo-4,5-dihydro-tetrazol-1-yl]-benzenesulfonamide Prepared from (2R)-6-{4-[4-(3-cyclohexylpropyl)-5-oxo-4,5-dihydrotetrazol-1-yl] benzenesulfonylamino} chroman-carboxylic acid isobutyl ester (Example 158) according to the procedures of Examples 137, 145, 146 and 154. mp 94–95° C.; $^1$H NMR (CD$_3$OD, 300 MHz) δ 8.08 (d, 8.8 Hz, 2 H), 7.87 (d, 2.2 Hz, 1 H), 7.82 (d, 8.8 Hz, 2 H), 7.49 (dd, 8.6 Hz, 2.4 Hz, 1 H), 6.75 (m, 2 H), 6.58 (m, 2 H), 4.66(m, 1 H), 4.10 (m, 1 H), 3.98 (t, 7.2 Hz, 2 H), 2.95–2.70 (m, 4 H), 2.65 (m, 2 H), 1.86 (m, 3 H), 1.71 (m, 6 H), 1.29 (m, 6 H), 0.91 (m, 2 H); $^{13}$C NMR (CD$_3$OD, 500 MHz) δ 160.5, 153.8, 150.5, 146.0, 139.8, 139.3, 137.6, 130.7, 129.8, 128.7, 125.7, 124.0, 123.7, 120.0, 118.1, 110.2, 76.1, 70.9, 57.4, 54.3, 46.5, 38.4, 35.2, 34.3, 27.7, 27.4, 26.7 26.4, 25.5; MS (ES) m/z 663 (MH$^+$); Anal. calcd for C$_{33}$H$_{42}$N$_8$O$_5$S: C, 59.80; H, 6.39; N, 16.91; S, 4.84; Found: C, 58.79; H, 6.40; N, 16.60; S, 4.61; R$_f$=0.10 (D).

Example 160 and Example 161 were prepared by the methods described in Example 137, Example 145, and Example 146.

| Example | Name | MS | R$_f$ |
|---|---|---|---|
| 160 | 4-[4-(3-Cyclohexylpropyl)-5-oxo-4,5-dihydrotetrazol-1-yl]-N-{(2R)-[((2R)-hydroxy-2-pyridin-3-ylethyl-amino)methyl]chroman-6-yl}benzenesulfonamide | 648 (M$^+$, electrospray) | 0.37 (O) |
| 161 | 4-[4-(3-Cyclohexylpropyl)-5-oxo-4,5-dihydrotetrazol-1-yl]-N-{(2S)-hydroxy-2-pyridin-3-ylethylamino)-methyl]chroman-6-yl}benzenesulfonamide | 648 (MH$^+$, electrospray) | 0.10 (K) |

EXAMPLE 162

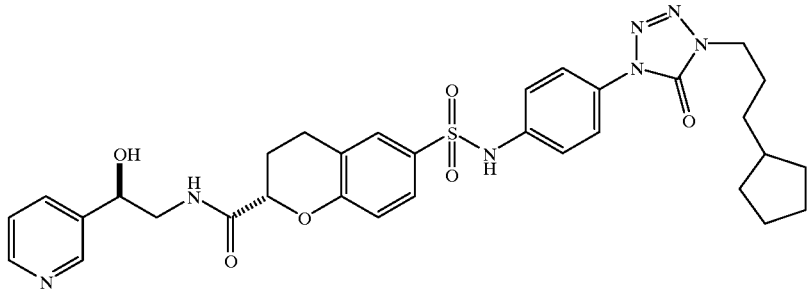

6-{4-[4-(3-Cyclopentyl-propyl)-5-oxo-4,5-dihyydro-tetrazol-1-yl]-phenylsulfamoyl}-chroman-(2S)-carboxylic acid [(2R)-hydroxy-2-pyridin-3-yl-ethyl]-amide To a stirring slurry of (R)-2-amino-1-pyridin-3-yl-ethanol dihydrochloride (Example 144, 800 mg, 3.79 mmol) in dichloromethane (25 mL) was added 6-{4-[4-(3-cyclopentyl-propyl)-5-oxo-4,5-dihydro-tetrazol-1-yl]-phenylsulfamoyl}-chroman-(S)-2-carboxylic acid (2 g, 3.79 mmol), benzotriazol-1-yloxytris(dimethylamino) phosphonium hexafluorophosphate (BOP reagent; 1.67 g, 3.79 mmol) and triethylamine(2.12 mL, 15.2 mmol). After stirring overnight the mixture was poured onto brine, diluted with ethyl acetate (25 mL), and extracted. The organic phase was washed with saturated sodium bicarbonate solution, 1N hydrochloric acid, and water. The organic phase was dried (MgSO$_4$), and concentrated to a yellow solid (2.26 g, 92%). Mp 123° C.: $^1$H NMR (DMSO-d$_6$, 300 MHz) δ 3.9(t, 2 H), 4.9(m, 1 H), 7.3(m, 2 H), 10.5(s, 1 H); R$_f$=0.43 (5:95 methanol/ethyl acetate).

It should be apparent to one of ordinary skill in the art that changes and modifications can be made to this invention without departing from the spirit or scope of the invention as it is set forth herein.

What is claimed as new and useful is:

1. A compound of the formula I:

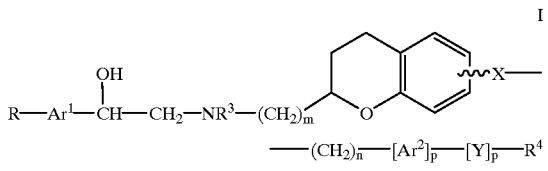

I wherein

R is hydrogen, hydroxy, oxo, halo, $C_1$–$C_{10}$haloalkyl, $C_1$–$C_{10}$ alkyl, cyano, nitro, $NR^1R^1$, $SR^1$, $OR^1$, $SO_2R^2$, $OCOR^2$, $NR^1COR^2$, $COR^2$, $NR^1SO_2R^2$, $NR^1CO_2R^1$, pyrrole, or $Ar^2$, each moiety being optionally substituted with hydroxy, halogen, cyano, $NR^1R^1$, $SR^1$, trifluoromethyl, $OR^1$, $C_3$–$C_8$ cycloaklyl, phenyl, $NR^1COR^2$, $COR^2$, $SO_2R^2$, $OCOR^2$, $NR^1SO_2R^2$, or $NR^1CO_2R^1$;

$R^1$ is hydrogen, $C_1$–$C_{10}$ alkyl optionally substituted with 1 to 4 substituents selected from hydroxy, halogen, $CO_2H$, $CO_2C_1$–$C_{10}$ alkyl, $SO_2C_1$–$C_{10}$alkyl, $C_1$–$C_{10}$ alkoxy; or $C_3$–$C_8$ cycloalkyl, phenyl or naphthyl, each optionally substituted with 1 to 4 substituents selected from halogen, nitro, oxo, $C_1$–$C_{10}$ alkyl, $C_1$–$C_{10}$ alkoxy, and $C_1$–$C_{10}$ alkylthio;

$R^2$ is $R^1$ or $NR^1R^1$;

$R^3$ is hydrogen, $C_1$–$C_{10}$ alkyl or

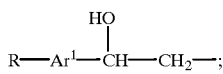

$Ar^1$ is $Ar^1$—O—$CH_2$, phenyl, or a 5 or 6 membered heterocyclic ring with from 1 to 4 heteroatoms selected from O, S and N, each moiety being optionally fused to a 5 or 6 membered heterocyclic ring containing from 1 to 4 hetero atoms selected from O, S, and N, the fused heterocyclic ring being optionally fused to a phenyl ring or substituted with oxo;

m is 1, 2 or 3;

$(CH_2)_m$ may be optionally replaced with C—(O)—$(CH_2)_m$;

X is $SO_2$-piperizinyl, $NR^3$—$SO_2$, or $SO_2$—$NR^3$;

n is 0, 1, 2, 3, or 4;

$Ar^2$ is phenyl, or a 5 or 6 membered heterocyclic ring with from 1 to 4 heteroatoms selected from O, S and N, each moiety being optionally substituted with halogen, $C_1$–$C_{10}$ alkyl, $C_1$–$C_{10}$ alkoxy, and OR, or being fused to a 5 or 6 membered heterocyclic ring containing from 1 to 4 hetero atoms selected from O, S, and N, the fused heterocyclic ring being optionally fused to a phenyl ring or optionally substituted with oxo;

Y is O—Y, $NR^1$, $NR^1CO$, $C_3$–$C_8$ cycloalkyl or a 5 or 6 membered heterocyclic ring with from 1 to 4 heteroatoms selected from O, S and N, each of which is optionally fused to phenyl, or optionally substituted with oxo;

p is 0 or 1;

$R^4$ is hydrogen, $R^1$, $R^2$, oxo, $C_1$–$C_{10}$ heteroalkyl, $C_1$–$C_{10}$ alkyl, $C_1$–$C_{10}$ haloalkyl, each being optionally substituted with $C_3$–$C_8$ cycloalkyl, phenyl, naphthyl, benzofuran, carbazole, dibenzothiofuran, or a 5 or 6 membered heterocyclic ring with from 1 to 4 heteroatoms selected from O, S, and N, each ring structure being optionally substituted with halo and $C_1$–$C_{10}$ alkyl, and pharmaceutically acceptable salts and esters thereof.

2. A compound of claim 1 wherein $Ar^1$ is optionally substituted phenyl or pyridyl, X is $NR^3$—$SO_2$ or $SO_2$—$NR^3$, $Ar^2$ is phenyl, pyridyl pyrimidinyl or pyrrolyl, Y is optionally substituted pyridyl, pyrrolyl, pyrimidinyl, quinolinyl, imadazolyl, and dihydrobenzofuranyl, and $R^4$ is $R^1$ or optionally substituted $C_1$–$C_{10}$ alkyl.

3. A compound of claim 2 wherein m is one and n is zero or one.

4. A compound of claim 3 wherein $R^3$ is hydrogen and $R^4$ is $C_1$–$C_{10}$ alkyl optionally substituted with $C_3$–$C_8$ cycloalkyl, phenyl, or pyridyl, each ring structure being optionally substituted with halo and $C_1$–$C_{10}$ alkyl.

5. A compound of claim 4 wherein R is hydrogen, halo, $C_1$–$C_{10}$ alkyl, nitro or $NR^1R^1$, X is attached to the chroman moiety in the 6 position, n is zero, $Ar^2$ is phenyl or pyridyl, and Y is pyridyl or pyrrolyl each optionally substituted with oxo.

6. A compound of claim 1 wherein the —OH group of the compound of Formula 1 is in the R configuration.

7. A pharmaceutical composition comprising an effective amount of a compound of claim 1 or a pharmaceutically acceptable salt thereof in combination with a pharmaceutically acceptable carrier.

8. A method of treating a beta-3 adrenergic receptor mediated condition which comprises administering to a patient in need thereof a pharmaceutically effective amount of a compound of Formula I:

Formula I

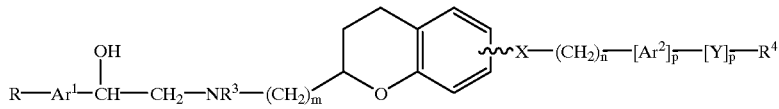

wherein

R is hydrogen, hydroxy, oxo, halo, $C_1$–$C_{10}$haloalkyl, $C_1$–$C_{10}$ alkyl, cyano, nitro, $NR^1R^1$, $SR^1$, $OR^1$, $SO_2R^2$, $OCOR^2$, $NR^1COR^2$, $COR^2$, $NR^1SO_2R^2$, $NR^1CO_2R^1$, pyrrole, or $Ar^2$, each moiety being optionally substituted with hydroxy, halogen, cyano, $NR^1R^1$, $SR^1$, trifluoromethyl, $OR^1$, $C_3$–$C_8$ cycloaklyl, phenyl, $NR^1COR^2$, $COR^2$, $SO_2R^2$, $OCOR^2$, $NR^1SO_2R^2$, or $NR^1CO_2R^1$;

$R^1$ is hydrogen, $C_1$–$C_{10}$ alkyl optionally substituted with 1 to 4 substituents selected from hydroxy, halogen, $CO_2H$, $CO_2C_1$–$C_{10}$ alkyl, $SO_2C_1$–$C_{10}$alkyl, $C_1$–$C_{10}$ alkoxy; or $C_3$–$C_8$ cycloalkyl, phenyl or naphthyl, each optionally substituted with 1 to 4 substituents selected from halogen, nitro, oxo, $C_1$–$C_{10}$ alkyl, $C_1$–$C_{10}$ alkoxy, and $C_1$–$C_{10}$ alkylthio;

$R^2$ is $R^1$ or $NR^1R^1$;

$R^3$ is hydrogen, $C_1$–$C_{10}$ alkyl or

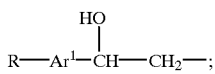

$Ar^1$ is $Ar^1$—O—$CH_2$, phenyl, or a 5 or 6 membered heterocyclic ring with from 1 to 4 heteroatoms selected from O, S and N, each moiety being optionally fused to a 5 or 6 membered heterocyclic ring containing from 1 to 4 hetero atoms selected from O, S, and N, the fused heterocyclic ring being optionally fused to a phenyl ring or substituted with oxo;

m is 1, 2 or 3;

$(CH_2)_m$ may be optionally replaced with $C(O)$—$(CH_2)_m$;

X is $SO_2$-piperizinyl, $NR^3$—$SO_2$, or $SO_2$—$NR^3$;

n is 0, 1, 2, 3, or 4;

$Ar^2$ is phenyl, or a 5 or 6 membered heterocyclic ring with from 1 to 4 heteroatoms selected from O, S and N, each moiety being optionally substituted with halogen, $C_1$–$C_{10}$ alkyl, $C_1$–$C_{10}$ alkoxy, and OR, or being fused to a 5 or 6 membered heterocyclic ring containing from 1 to 4 hetero atoms selected from O, S, and N, the fused heterocyclic ring being optionally fused to a phenyl ring or optionally substituted with oxo;

Y is O—Y, $NR^1$, $NR^1CO$, $C_3$–$C_8$ cycloalkyl or a 5 or 6 membered heterocyclic ring with from 1 to 4 heteroatoms selected from O, S and N, each of which is optionally fused to phenyl or optionally substituted with oxo;

p is 0 or 1;

$R^4$ is hydrogen, $R^1$, $R^2$, oxo, $C_1$–$C_{10}$ heteroalkyl, $C_1$–$C_{10}$ alkyl, $C_1$–$C_{10}$ haloalkyl, each being optionally substituted with $C_3$–$C_8$ cycloalkyl, phenyl, naphthyl, benzofuran, carbazole, dibenzothiofuran, or a 5 or 6 membered heterocyclic ring with from 1 to 4 heteroatoms selected from O, S, and N, each ring structure being optionally substituted with halo and $C_1$–$C_{10}$ alkyl, and pharmaceutically acceptable salts and esters thereof.

9. A method of treating obesity in a mammal which comprises administering to a patient in need thereof a pharmaceutically effective amount of a compound of Formula I:

Formula I

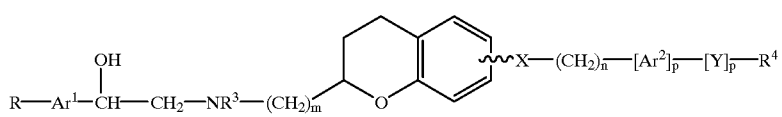

wherein

R is hydrogen, hydroxy, oxo, halo, $C_1$–$C_{10}$haloalkyl, $C_1$–$C_{10}$ alkyl, cyano, nitro, $NR^1R^1$, $SR^1$, $OR^1$, $SO_2R^2$, $OCOR^2$, $NR^1COR^2$, $COR^2$, $NR^1SO_2R^2$, $NR^1CO_2R^1$, pyrrole, or $Ar^2$, each moiety being optionally substituted with hydroxy, halogen, cyano, $NR^1R^1$, $SR^1$, trifluoromethyl, $OR^1$, $C_3$–$C_8$ cycloaklyl, phenyl, $NR^1COR^2$, $COR^2$, $SO_2R^2$, $OCOR^2$, $NR^1 SO_2R^2$, or $NR^1 CO_2R^1$;

$R^1$ is hydrogen, $C_1$–$C_{10}$ alkyl optionally substituted with 1 to 4 substituents selected from hydroxy, halogen, $CO_2H$, $CO_2C_1$–$C_{10}$ alkyl, $SO_2C_1$–$C_{10}$alkyl, $C_1$–$C_{10}$ alkoxy; or $C_3$–$C_8$ cycloalkyl, phenyl or naphthyl, each optionally substituted with 1 to 4 substituents selected from halogen, nitro, oxo, $C_1$–$C_{10}$ alkyl, $C_1$–$C_{10}$ alkoxy, and $C_1$–$C_{10}$ alkylthio;

$R^2$ is $R^1$ or $NR^1 R^1$;

$R^3$ is hydrogen, $C_1$–$C_{10}$ alkyl or

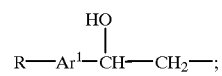

$Ar^1$ is $Ar^1$—O—$CH_2$, phenyl, or a 5 or 6 membered heterocyclic ring with from 1 to 4 heteroatoms selected from O, S and N, each moiety being optionally fused to a 5 or 6 membered heterocyclic ring containing from 1 to 4 hetero atoms selected from O, S, and N, the fused heterocyclic ring being optionally fused to a phenyl ring or substituted with oxo;

m is 1, 2 or 3;

$(CH_2)_m$ may be optionally replaced with $C(O)$—$(CH_2)_m$;

X is $SO_2$-piperizinyl, $NR^3$—$SO_2$, or $SO_2$—$NR^3$;

n is 0, 1, 2, 3, or 4;

$Ar^2$ is phenyl, or a 5 or 6 membered heterocyclic ring with from 1 to 4 heteroatoms selected from O, S and N, each moiety being optionally substituted with halogen, $C_1$–$C_{10}$ alkyl, $C_1$–$C_{10}$ alkoxy, and OR, or being fused to a 5 or 6 membered heterocyclic ring containing from 1 to 4 hetero atoms selected from O, S, and N, the fused heterocyclic ring being optionally fused to a phenyl ring or optionally substituted with oxo;

Y is O—Y $NR^1$, $NR^1CO$, $C_3$–$C_8$ cycloalkyl or a 5 or 6 membered heterocyclic ring with from 1 to 4 heteroatoms selected from O, S and N, each of which is optionally fused to phenyl or optionally substituted with oxo;

p is 0 or 1;

$R^4$ is hydrogen, $R^1$, $R^2$, oxo, $C_1$–$C_{10}$ heteroalkyl, $C_1$–$C_{10}$ alkyl, $C_1$–$C_{10}$ haloalkyl, each being optionally substituted with $C_3$–$C_8$ cycloalkyl, phenyl, naphthyl, benzofuran, carbazole, dibenzothiofuran, or a 5 or 6 membered heterocyclic ring with from 1 to 4 heteroatoms selected from O, S, and N, each ring structure being optionally substituted with halo and $C_1$–$C_{10}$ alkyl, and pharmaceutically acceptable salts and esters thereof.

10. A method of treating diabetes in mammals which comprises administering to a patient in need thereof a pharmaceutically effective amount of a compound of Formula I:

Formula I

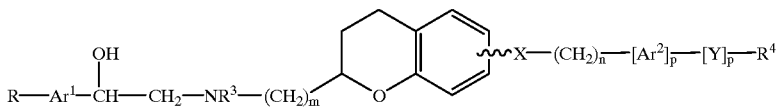

wherein
- R is hydrogen, hydroxy, oxo, halo, $C_1$–$C_{10}$ haloalkyl, $C_1$–$C_{10}$ alkyl, cyano, nitro, $NR^1R^1$, $SR^1$, $OR^1$, $SO_2R^2$, $OCOR^2$, $NR^1COR^2$, $COR^2$, $NR^1SO_2R^2$, $NR^1CO_2R^1$, pyrrole, or $Ar^2$, each moiety being optionally substituted with hydroxy, halogen, cyano, $NR^1R^1$, $SR^1$, trifluoromethyl, $OR^1$, $C_3$–$C_8$ cycloaklyl, phenyl, $NR^1COR^2$, $COR^2$, $SO_2R^2$, $OCOR^2$, $NR^1SO_2R^2$, or $NR^1CO_2R^1$;
- $R^1$ is hydrogen, $C_1$–$C_{10}$ alkyl optionally substituted with 1 to 4 substituents selected from hydroxy, halogen, $CO_2H$, $CO_2C_1$–$C_{10}$ alkyl, $SO_2C_1$–$C_{10}$ alkyl, $C_1$–$C_{10}$ alkoxy; or $C_3$–$C_8$ cycloalkyl, phenyl or naphthyl, each optionally substituted with 1 to 4 substituents selected from halogen, nitro, oxo, $C_1$–$C_{10}$ alkyl, $C_1$–$C_{10}$ alkoxy, and $C_1$–$C_{10}$ alkylthio;
- $R^2$ is $R^1$ or $NR^1R^1$;
- $R^3$ is hydrogen, $C_1$–$C_{10}$ alkyl or

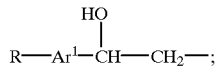

- $Ar^1$ is $Ar^1$—O—$CH_2$, phenyl, or a 5 or 6 membered heterocyclic ring with from 1 to 4 heteroatoms selected from O, S and N, each moiety being optionally fused to a 5 or 6 membered heterocyclic ring containing from 1 to 4 hetero atoms selected from O, S, and N, the fused heterocyclic ring being optionally fused to a phenyl ring or substituted with oxo;
- m is 1, 2 or 3;
- $(CH_2)_m$ may be optionally replaced with C(O)—$(CH_2)_m$;
- X is $SO_2$-piperizinyl, $NR^3$—$SO_2$, or $SO_2$—$NR^3$;
- n is 0, 1, 2, 3, or 4;
- $Ar^2$ is phenyl, or a 5 or 6 membered heterocyclic ring with from 1 to 4 heteroatoms selected from O, S and N, each moiety being optionally substituted with halogen, $C_1$–$C_{10}$ alkyl, $C_1$–$C_{10}$ alkoxy, and OR, or being fused to a 5 or 6 membered heterocyclic ring containing from 1 to 4 hetero atoms selected from O, S, and N, the fused heterocyclic ring being optionally fused to a phenyl ring or optionally substituted with oxo;
- Y is O—Y, $NR^1$, $NR^1CO$, $C_3$–$C_8$ cycloalkyl or a 5 or 6 membered heterocyclic ring with from 1 to 4 heteroatoms selected from O, S and N, each of which is optionally fused to phenyl or optionally substituted with oxo;
- p is 0 or 1;
- $R^4$ is hydrogen, $R^1$, $R^2$, oxo, $C_1$–$C_{10}$ heteroalkyl, $C_1$–$C_{10}$ alkyl, $C_1$–$C_{10}$ haloalkyl, each being optionally substituted with $C_3$–$C_8$ cycloalkyl, phenyl, naphthyl, benzofuran, carbazole, dibenzothiofuran, or a 5 or 6 membered heterocyclic ring with from 1 to 4 heteroatoms selected from O, S, and N, each ring structure being optionally substituted with halo and $C_1$–$C_{10}$ alkyl, and pharmaceutically acceptable salts and esters thereof.

11. A composition useful in research or diagnostics, comprising an effective amount of a compound of Formula I:

Formula I

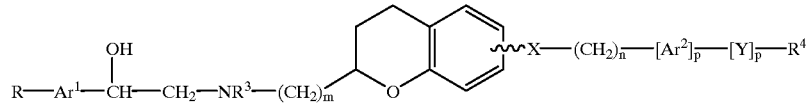

wherein
- R is hydrogen, hydroxy, oxo, halo, $C_1$–$C_{10}$ haloalkyl, $C_1$–$C_{10}$ alkyl, cyano, nitro, $NR^1R^1$, $SR^1$, $OR^1$, $SO_2R^2$, $OCOR^2$, $NR^1COR^2$, $COR^2$, $NR^1SO_2R^2$, $NR^1CO_2R^1$, pyrrole, or $Ar^2$, each moiety being optionally substituted with hydroxy, halogen, cyano, $NR^1R^1$, $SR^1$, trifluoromethyl, $OR^1$, $C_3$–$C_8$ cycloaklyl, phenyl, $NR^1COR^2$, $COR^2$, $SO_2R^2$, $OCOR^2$, $NR^1SO_2R^2$, or $NR^1CO_2R^1$;
- $R^1$ is hydrogen, $C_1$–$C_{10}$ alkyl optionally substituted with 1 to 4 substituents selected from hydroxy, halogen, $CO_2H$, $CO_2C_1$–$C_{10}$ alkyl, $SO_2C_1$–$C_{10}$ alkyl, $C_1$–$C_{10}$ alkoxy; or $C_3$–$C_8$ cycloalkyl, phenyl or naphthyl, each optionally substituted with 1 to 4 substituents selected from halogen, nitro, oxo, $C_1$–$C_{10}$ alkyl, $C_1$–$C_{10}$ alkoxy, and $C_1$–$C_{10}$ alkylthio;
- $R^2$ is $R^1$ or $NR^1R^1$;
- $R^3$ is hydrogen, $C_1$–$C_{10}$ alkyl or

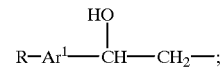

- $Ar^1$ is $Ar^1$—O—$CH_2$, phenyl, or a 5 or 6 membered heterocyclic ring with from 1 to 4 heteroatoms selected from O, S and N, each moiety being optionally fused to a 5 or 6 membered heterocyclic ring containing from 1 to 4 hetero atoms selected from O, S, and N, the fused heterocyclic ring being optionally fused to a phenyl ring or substituted with oxo;
- m is 1, 2 or 3;
- $(CH_2)_m$ may be optionally replaced with C(O)—$(CH_2)_m$;
- X is $SO_2$-piperizinyl, $NR^3$—$SO_2$, or $SO_2$—$NR^3$;
- n is 0, 1, 2, 3, or 4;

Ar$^2$ is phenyl, or a 5 or 6 membered heterocyclic ring with from 1 to 4 heteroatoms selected from O, S and N, each moiety being optionally substituted with halogen, C$_1$–C$_{10}$ alkyl, C$_1$–C$_{10}$ alkoxy, and OR, or being fused to a 5 or 6 membered heterocyclic ring containing from 1 to 4 hetero atoms selected from O, S, and N, the fused heterocyclic ring being optionally fused to a phenyl ring or optionally substituted with oxo;

Y is O—Y, NR$^1$, NR$^1$CO, C$_3$–C$_8$ cycloalkyl or a 5 or 6 membered heterocyclic ring with from 1 to 4 heteroatoms selected from O, S and N, each of which is optionally fused to phenyl or optionally substituted with oxo;

p is 0 or 1;

R$^4$ is hydrogen, R$^1$, R$^2$, oxo, C$_1$–C$_{10}$ heteroalkyl, C$_1$–C$_{10}$ alkyl, C$_1$–C$_{10}$ haloalkyl, each being optionally substituted with C$_3$–C$_8$ cycloalkyl, phenyl, naphthyl, benzofuran, carbazole, dibenzothiofuran, or a 5 or 6 membered heterocyclic ring with from 1 to 4 heteroatoms selected from O, S, and N, each ring structure being optionally substituted with halo and C$_1$–C$_{10}$ alkyl, in combination with an inert carrier.

* * * * *